United States Patent
Aoki et al.

(10) Patent No.: US 10,898,065 B2
(45) Date of Patent: Jan. 26, 2021

(54) IN-VIVO MONITORING CAMERA SYSTEM

(71) Applicant: Sharp Kabushiki Kaisha, Osaka (JP)

(72) Inventors: Hitoshi Aoki, Sakai (JP); Toshihisa Gotoh, Sakai (JP); Kei Urakawa, Sakai (JP); Kishoh Takamatsu, Sakai (JP); Tomohiro Konishi, Sakai (JP); Kazunori Morita, Sakai (JP); Tadahiko Sato, Sakai (JP)

(73) Assignee: Sharp Kabushiki Kaisha, Sakai (JP)

( * ) Notice: Subject to any disclaimer, the term of this patent is extended or adjusted under 35 U.S.C. 154(b) by 419 days.

(21) Appl. No.: 15/736,316

(22) PCT Filed: May 9, 2016

(86) PCT No.: PCT/JP2016/063723
§ 371 (c)(1),
(2) Date: Dec. 14, 2017

(87) PCT Pub. No.: WO2016/203864
PCT Pub. Date: Dec. 22, 2016

(65) Prior Publication Data
US 2018/0132707 A1     May 17, 2018

(30) Foreign Application Priority Data

Jun. 16, 2015 (JP) ................. 2015-121549
Dec. 21, 2015 (JP) ................. 2015-248819

(51) Int. Cl.
*A61B 1/00* (2006.01)
*A61B 1/05* (2006.01)
(Continued)

(52) U.S. Cl.
CPC ............ *A61B 1/05* (2013.01); *A61B 1/00045* (2013.01); *A61B 1/00119* (2013.01);
(Continued)

(58) Field of Classification Search
CPC ........................... A61B 1/00114; A61B 1/041
(Continued)

(56) References Cited

U.S. PATENT DOCUMENTS

2008/0309758 A1* 12/2008 Karasawa ............ A61B 1/3132
                                                                                     348/65
2011/0046440 A1    2/2011 Asada et al.
(Continued)

FOREIGN PATENT DOCUMENTS

JP        4472727 B2    6/2010
JP        4599474 B1   12/2010
(Continued)

OTHER PUBLICATIONS

Official Communication issued in International Patent Application No. PCT/JP2016/063723, dated Aug. 2, 2016.

*Primary Examiner* — Alexandra L Newton
*Assistant Examiner* — Rynae Boler
(74) *Attorney, Agent, or Firm* — Keating & Bennett, LLP

(57) ABSTRACT

An in-vivo monitoring camera system includes an image capturing portion (camera unit 11) that is capable of being introduced into a body, a support tube (13) that has a connection portion (trocar connection portion 13*x*) with a tubular tool (trocar 31) which is capable of being introduced into the body on one end side and has a joining portion (protrusion type joining portion 13*y*) to the image capturing portion on another end side, a cable (camera-side cable 12) that is connected with the image capturing portion and passes through the support tube, and a control system that is electrically connected with the cable and includes at least a display device (18).

9 Claims, 39 Drawing Sheets

(51) Int. Cl.
*H04N 5/225* (2006.01)
*A61B 1/313* (2006.01)
*A61B 1/04* (2006.01)
*A61B 1/045* (2006.01)
*A61B 17/34* (2006.01)
*A61B 90/30* (2016.01)
*A61B 90/00* (2016.01)
*G02B 23/24* (2006.01)

(52) U.S. Cl.
CPC ...... *A61B 1/00124* (2013.01); *A61B 1/00154* (2013.01); *A61B 1/041* (2013.01); *A61B 1/045* (2013.01); *A61B 1/3132* (2013.01); *H04N 5/2252* (2013.01); *A61B 1/00018* (2013.01); *A61B 1/00114* (2013.01); *A61B 1/00147* (2013.01); *A61B 17/3421* (2013.01); *A61B 90/361* (2016.02); *A61B 2090/309* (2016.02); *G02B 23/2484* (2013.01); *H04N 2005/2255* (2013.01)

(58) Field of Classification Search
USPC .......................................... 600/109; 348/65
See application file for complete search history.

(56) References Cited

U.S. PATENT DOCUMENTS

| | | | |
|---|---|---|---|
| 2012/0050511 A1* | 3/2012 | Takahashi | A61B 1/00114 348/65 |
| 2016/0143510 A1 | 5/2016 | Gotoh et al. | |
| 2016/0234408 A1 | 8/2016 | Urakawa et al. | |
| 2016/0263350 A1 | 9/2016 | Urakawa et al. | |

FOREIGN PATENT DOCUMENTS

| | | |
|---|---|---|
| WO | 2012/026156 A1 | 3/2012 |
| WO | 2015/020124 A1 | 2/2015 |
| WO | 2015/064743 A1 | 5/2015 |
| WO | 2015/080293 A1 | 6/2015 |

* cited by examiner (a)

(b)

(a)

(b)

(a)

(b)

(c)

(a)

(b)

(a)

(b)

(a)

(b)

(a)

(b)

(a)

(b)

IN-VIVO MONITORING CAMERA SYSTEM

TECHNICAL FIELD

The present invention relates to an in-vivo monitoring camera system that includes an image capturing portion which is capable of being introduced into a body.

BACKGROUND ART

Endoscopic surgery is a minimally invasive surgery that performs examinations and curative treatments without a laparotomy on a patient. In endoscopic surgery, treatment instruments such as forceps and an endoscope are separately introduced into a body cavity of the patient, and an operator has an image at a tip end portion of the treatment instrument inserted in the body cavity in an observation view field of the endoscope and performs treatment work while observing a treatment state of an affected site by the treatment instrument by the endoscope. In the endoscopic surgery, the treatment instruments and the endoscope are introduced into the body cavity through a pipe punctured through a body wall (for example, an abdominal wall) in an abdomen or the like of the patient. The pipe is a tubular member, which is commonly referred to as trocar.

The operator enlarges an image by making the endoscope approach an organ and thereby performs incision or suture of the organ. However, the view field of the operator becomes very narrow. Thus, a device is demanded by which a state of the outside of a working area (for example, motion of the treatment instrument on the outside of the working area, a state of bleeding, and a residual state of residues such as gauze) may be widely perceived.

In consideration of such a demand, PTL 1 discloses a device that directly places a connector electrode having a needle shape into the abdominal wall and joins the connector electrode to a camera in the body and a device that places the connector electrode having a needle shape into the abdominal wall reversely from the inside of the body and joins the connector electrode to the camera on the outside of the body.

Further, PTL 2 discloses a device that inserts a camera unit and a communication cable to be joined thereto through a trocar, draws out a catching needle and the communication cable to the outside of the body through a hole in the abdominal wall in a state where an end of the communication cable is caught by the catching needle inserted through the hole in the abdominal wall, and thereby fixes the communication cable.

CITATION LIST

Patent Literature

PTL 1: Japanese Patent No. 4472727 (issued on Jun. 2, 2010)
PTL 2: Japanese Patent No. 4599474 (issued on Dec. 15, 2010)
PTL 3: International Publication No. 2015/020124 (issued on Feb. 12, 2015)
PTL 4: International Publication No. 2015/064743 (issued on May 7, 2015)

SUMMARY OF INVENTION

Technical Problem

In PTL 1, because a connector electrode in a needle shape is directly placed into the abdominal wall and the connector electrode is joined to a camera in the body, a foreign object may enter a joining portion between the connector electrode and the camera, and electrical connection failure may occur.

In PTL 2, the communication cable is drawn out to the outside of the body and fixed. However, it is difficult to gain the joining strength between the communication cable and a camera unit due to the properties of the communication cable and also difficult to change the orientation of the camera unit from the outside of the body.

The present invention suggests an in-vivo monitoring camera system that is highly reliable and easy to use.

Solution to Problem

This in-vivo monitoring camera system includes an image capturing portion that is capable of being introduced into a body, a support tube that has a joining portion to the image capturing portion on one end side and has a connection portion with a tubular tool which is capable of being introduced into the body on another end side, a cable that is connected with the image capturing portion and passes through the support tube, and a control system that is electrically connected with the cable and includes at least a display device.

Advantageous Effects of Invention

This in-vivo monitoring camera system may enhance the supporting force for an image capturing portion, make connection failure of a cable be less likely to occur, and improve reliability. Further, an operator may change the orientation of the image capturing portion in the body by operating a tubular tool, and easiness of use is thereby improved.

DESCRIPTION OF EMBODIMENTS

Embodiments of the present invention will hereinafter be described based on FIG. 1 to FIG. 39. Note that an outer diameter described below means the maximum outer diameter.

First Embodiment (Configuration of In-Vivo Monitoring Camera System)

Figure 1:
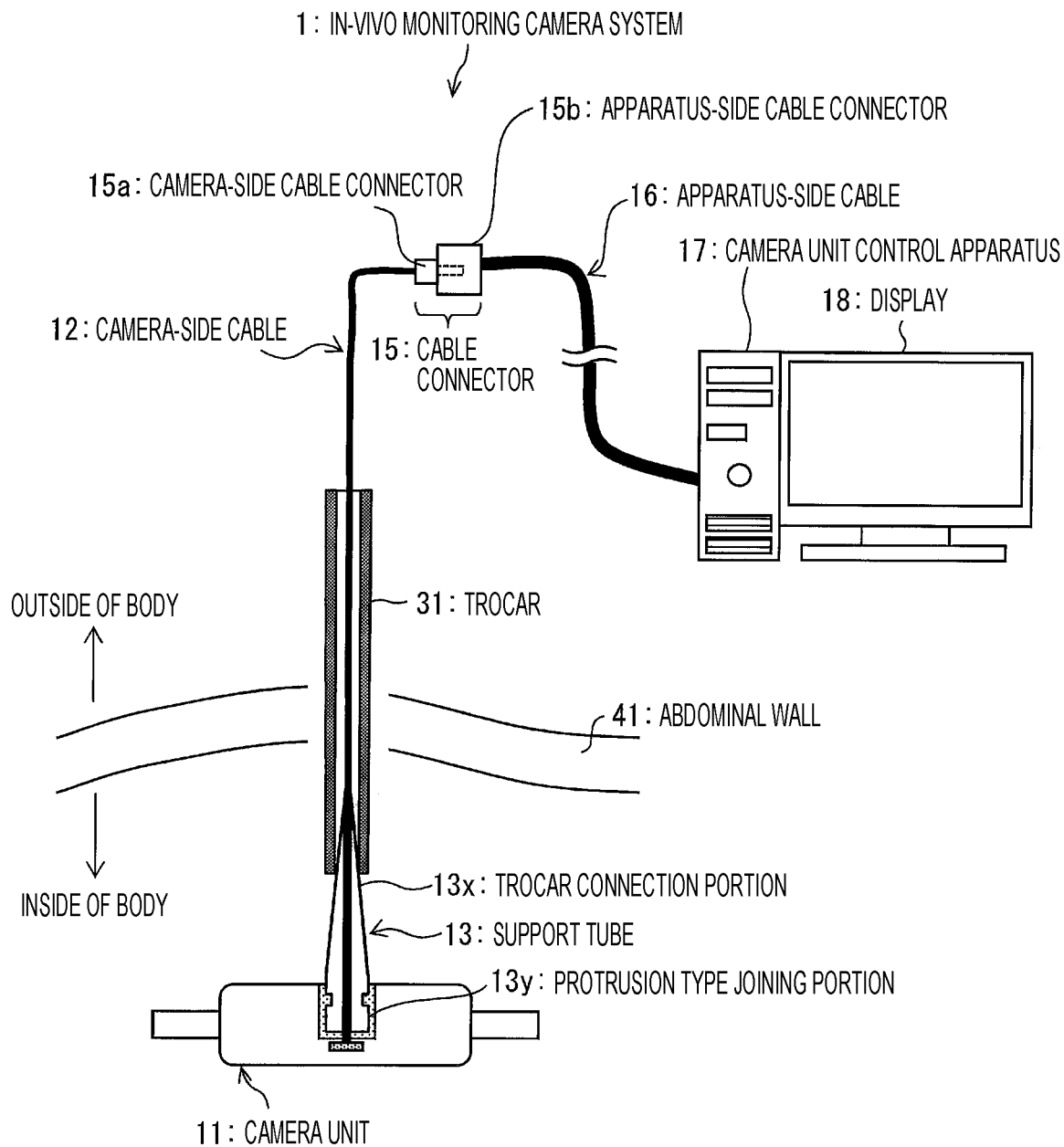
FIG. 1 is a schematic diagram that illustrates a configuration of an in-vivo monitoring camera system of a first embodiment.

FIG. 1 is a schematic diagram that illustrates a configuration of an in-vivo monitoring camera system of a first embodiment. As illustrated in FIG. 1, an in-vivo monitoring camera system 1 includes a camera unit 11 (image capturing portion) that is introduced into a body, a support tube (support instrument) 13 that has a trocar connection portion 13x (connection portion) which is used for connection with a trocar 31 (tubular tool) introduced into the body on one end side and has a protrusion type joining portion 13y (joining portion) which is used for joining to the camera unit 11 on the other end side, a camera-side cable 12 that is connected with the camera unit 11 and passes through an internal portion of the support tube 13, a control system that includes a camera unit control apparatus 17 and a display 18 (display device), and an apparatus-side cable 16 that is connected with the camera-side cable 12 and the camera unit control apparatus 17.

Note that the camera-side cable 12 has a protrusion type camera-side cable connector 15a on the opposite side to a connection end with the camera unit 11, and the apparatus-side cable 16 has a recess type apparatus-side cable connector 15b on the opposite side to a connection end with the camera unit control apparatus 17. Note that a configuration is possible in which a recess type camera-side cable connector and a protrusion type apparatus-side cable connector are fitted together. Further, although one pin of the camera-side cable connector 15a is illustrated in FIG. 1, the number of pins usually corresponds to the number of power lines used for the cable. In the description made below, a camera-side cable connector 15a and an apparatus-side cable connector 15b may be abbreviated to connector 15a and connector 15b, respectively.

In the in-vivo monitoring camera system 1, an end on the inside of the body of the trocar 31 punctured through an abdominal wall 41 is connected with the support tube 13 by the trocar connection portion 13x, the camera unit 11 introduced into the body is joined to the support tube 13 by the protrusion type joining portion 13y, and the connector 15a of the camera-side cable 12 is drawn out to the outside of the body through the support tube 13 and the trocar 31. Further, the camera-side cable connector 15a is fitted in the apparatus-side cable connector 15b, the camera unit 11 and the camera unit control apparatus 17 are thereby electrically connected together, and a picture photographed by the camera unit 11 is transmitted to the camera unit control apparatus 17. The camera unit control apparatus 17 causes the display 18 to display the picture transmitted from the camera unit 11 and transmits control signals to the camera unit 11. Note that the camera unit control apparatus 17 and the display 18 may be formed integrally or separately.

Here, a wired scheme is employed for transmission from the camera unit 11 to the camera unit control apparatus 17. Thus, the transmission rate may be made high, and high resolution images may be obtained because signals may stably be transmitted and received. Further, communication may be performed with low power compared to a wireless scheme, and size reduction of the camera unit 11 may be intended by supplying a power source from the outside. Accordingly, a wound for introduction of the camera unit 11 into the body may be made small by the size reduction, thus providing an effect of improving minimal invasiveness.
(Configuration of Camera Unit)

Figure 2:
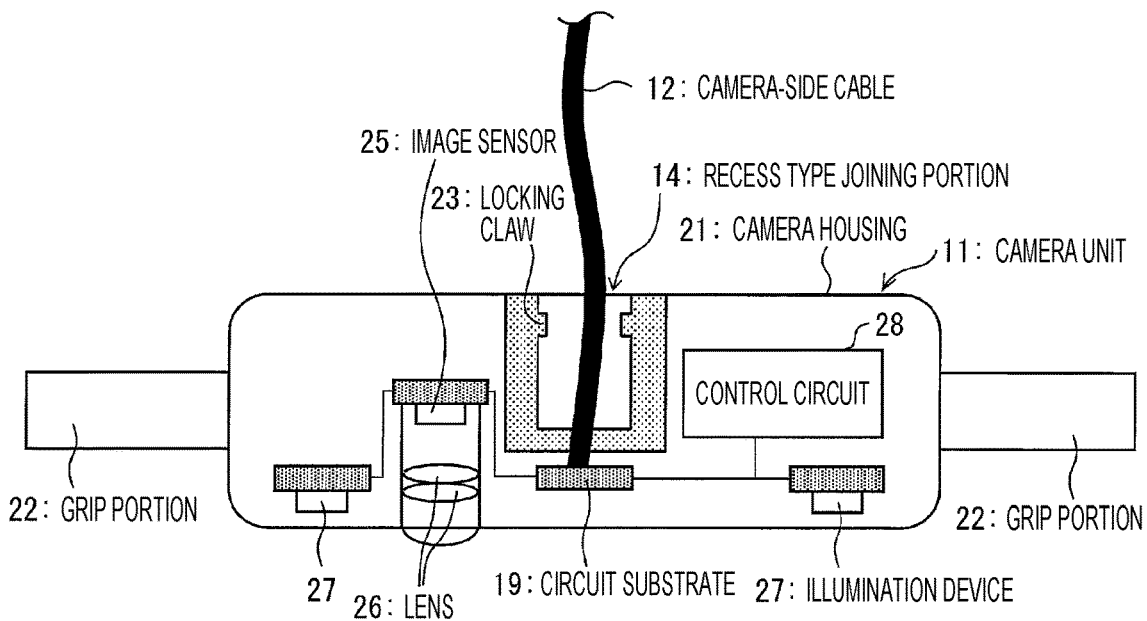
FIG. 2 is a cross-sectional diagram (a) and a top diagram (b) that illustrate a configuration of a camera unit of the first embodiment.
Figure 2:
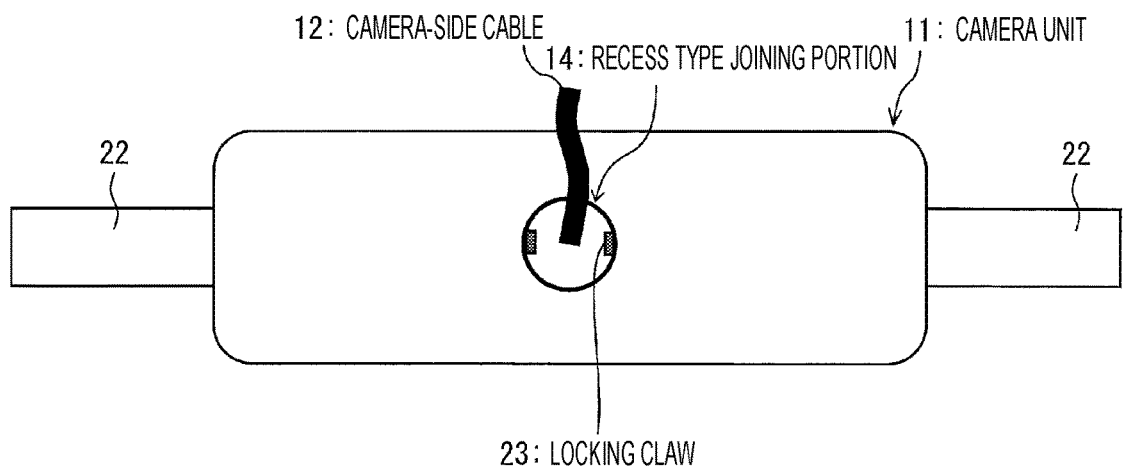

FIG. 2 is a cross-sectional diagram (a) and a top diagram (b) that illustrate a configuration of a camera unit of the first embodiment. As illustrated in (a) and (b) in FIG. 2, the camera unit 11 is provided with a circuit substrate 19, and an image sensor 25, a control circuit 28, and illumination devices 27 that are connected with the circuit substrate 19, and lenses 26, in a camera housing 21.

A recess type joining portion 14 is provided on an upper surface of the camera housing 21. The recess type joining portion 14 has a hole structure with a circular opening and is provided with a locking claw 23 on an inner wall. Grip portions 22 are provided on both side surfaces of the camera housing 21 that are opposed to each other. The grip portion 22 is grasped when the camera unit 11 is introduced into the body by using forceps or grasped such that an upper surface of the camera unit 11 faces the protrusion type joining portion 13y of the support tube 13 when the camera unit 11 and the support tube 13 are joined together.

The camera-side cable 12 is connected with the circuit substrate 19 and is guided to the outside of the camera unit 11 so as to pass through an internal portion of the recess type joining portion 14. A connection part between the circuit substrate 19 and the camera-side cable 12 is sealed by a resin or the like. In addition, in a portion (a bottom portion of the recess type joining portion 14) from which the camera-side cable 12 is drawn out in the internal portion of the recess type joining portion 14, the camera-side cable 12 is bonded and fixed to the bottom portion of the recess type joining portion 14. For example, sealed fixing by an adhesive or an O-ring is performed. A configuration is thereby made which avoids occurrence of flooding, entrance of a foreign object, or the like (into the camera unit 11) from this portion. The camera-side cable 12 is introduced into the body cavity through a trocar and is thus formed of a flexible material.

The image sensor 25 is a CCD, a CMOS image sensor, or the like, and the illumination device 27 illuminates the inside of the body and thereby makes pictures photographed by the camera unit 11 clear. The illumination device 27 is preferably of a small size, and an LED or the like is suitably used, for example. Note that as illustrated in FIG. 2, plural illumination devices 27 may be installed in the camera housing 21.

Further, in the camera housing 21 of the camera unit 11, portions in which the lenses 26 and the illumination devices 27 are arranged are formed to be transparent, but other portions are desirably configured with blue or green materials that are easy to recognize on the inside of the body. Further, a film on a surface of the camera-side cable 12 (including the connector 15a) is desirably formed to be blue or green. In such a manner, blue and green in the complementary color relationship with colors of the inside of the body such as red and yellow, specifically, colors that correspond to visible light at wavelengths of 420 to 570 nm (particularly preferably 450 to 530 nm) are used, and installation work and collection work in the body, which will be described later, may thereby be facilitated.
(Configuration and Function of Support Tube)

Figure 3:
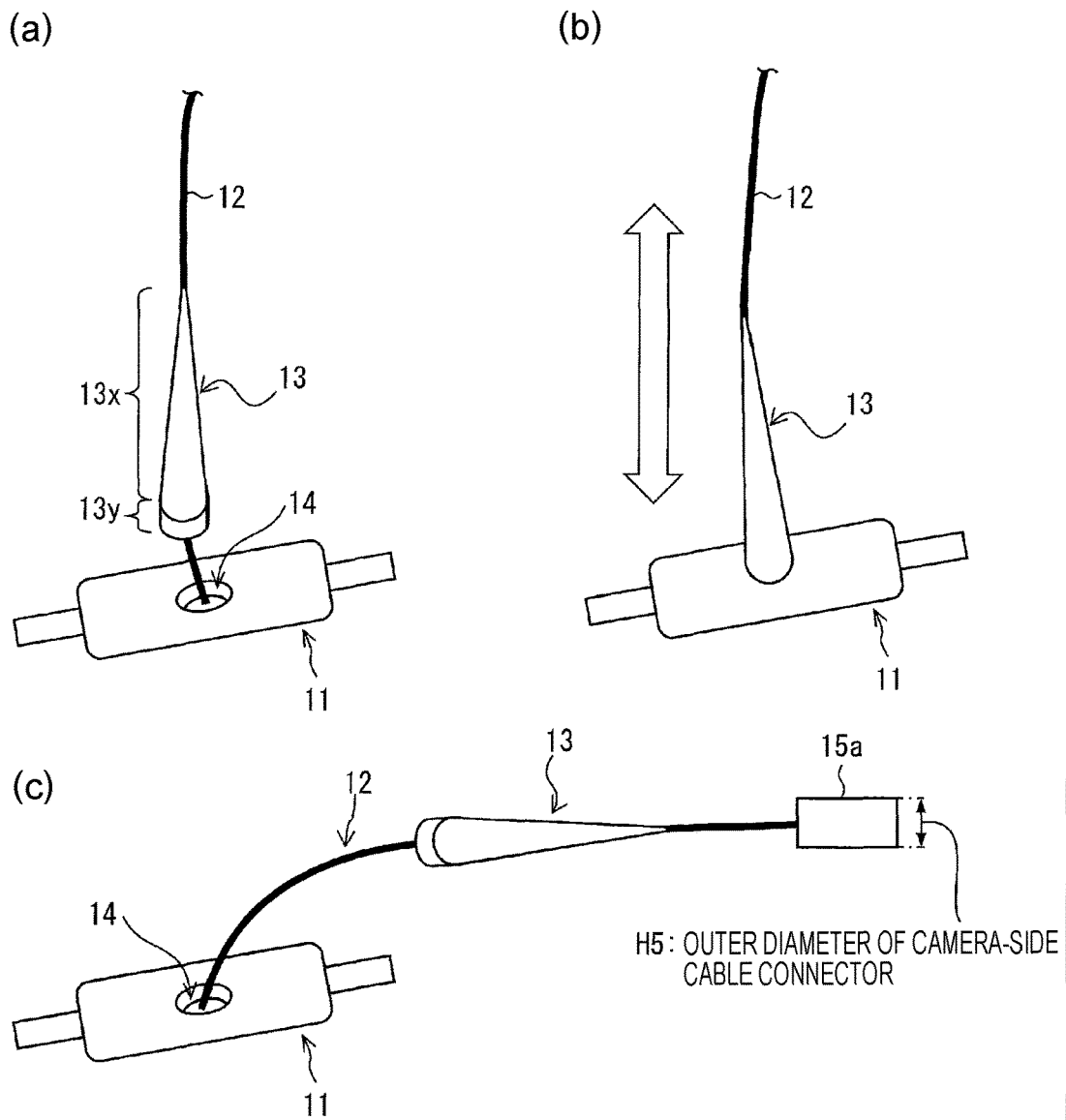
FIG. 3 is perspective diagrams (a) to (c) that illustrate the relationship between a support tube and the camera unit in the first embodiment.

FIG. 3 is perspective diagrams (a) to (c) that illustrate the relationship between a support tube and a camera unit in the first embodiment. As illustrated in (a) and (b) in FIG. 3, the support tube 13 has the trocar connection portion 13x used for connection with the trocar on one end side and has the protrusion type joining portion 13y on the other end side. The recess type joining portion 14 of the camera unit 11 is fitted in the protrusion type joining portion 13y of the support tube 13, and the support tube 13 and the camera unit 11 are thereby joined together. The protrusion type joining portion 13y is pulled out from the recess type joining portion 14 of the camera unit 11, and the support tube 13 is thereby separated from the camera unit 11.

As illustrated in (a) to (c) in FIG. 3, the trocar connection portion 13x of the support tube 13 is in a tapered shape that is tapered away from the protrusion type joining portion 13y, specifically, a conical shape. The protrusion type joining portion 13y of the support tube 13 is in a columnar shape, and the outer diameter thereof is the same as the outer diameter of an end surface on a thicker side of the trocar connection portion 13x. Note that the trocar connection portion 13x in FIG. 3 is in a linearly tapered shape (conical shape) whose taper ratio is constant but is not limited to this. For example, the trocar connection portion 13x may be in a tapered shape whose taper ratio becomes lower toward a tip end (trocar side) or whose taper ratio reversely becomes higher toward the tip end. The same applies to the embodiments described later.

The camera-side cable 12 drawn out from the recess type joining portion 14 of the camera unit 11 passes through a cable hole formed in an internal portion of the protrusion type joining portion 13y in the columnar shape and a cable hole formed in an internal portion of the trocar connection portion 13x in the conical shape and reaches the outside of the support tube 13. The inner diameter of the support tube 13 (the hole diameter of the cable holes) is the same from one end to the other end and is equal to or more than the outer diameter of the camera-side cable 12 to less than the outer diameter (H5) of the camera-side cable connector 15a.

That is, the support tube 13 through which the camera-side cable 12 passes and which is placed between the connection part with the camera unit 11 and the camera-side cable connector 15a is in a state where the support tube 13 is limitedly movable between those. In a case where the support tube 13, the camera unit 11, and the camera-side cable connector 15a are introduced from the inside of the tubular tool into the body, the support tube 13 may be in a state where the support tube 13 is separated from the camera unit 11 and is easily introduced into the body (see (c) in FIG. 3).

Note that an inside surface (wall surfaces of the cable holes) of the support tube 13 desirably contacts with the camera-side cable 12 such that the support tube 13 is moderately retained in an intermediate position of the camera-side cable 12 (the vicinity of the camera unit 11) (in a state where the support tube 13 is retained in the position by the cable unless a force is particularly added but is movable along the cable in a case where a light force is added). If the support tube 13 is in a state where no contact resistance is present, in a case where installation work is performed by pinching the camera unit 11 by forceps, the support tube 13 moves (dangles) toward the connector 15a side at each time when the camera unit 11 is moved, the position of a cable end (connector 15a) is thus not fixed, and the efficiency of the installation work lowers. This effect is not limited to this first embodiment, but the same applies to the other embodiments in the following.

Further, in general, gas sterilization is used for such an electronic apparatus. As described above, because the support tube 13 is in advance attached to the camera-side cable 12, the gas sterilization is performed in this state. Thus, the gas has to moderately infiltrate the contact surface between the support tube 13 and the camera-side cable 12, and sterilization has to be thereby performed. Accordingly, the support tube 13 and the camera-side cable 12 have to partially contact with each other but have to have gaps for entry of the gas in micro-scale. Because a comparatively flexible cable has distortions and fine protrusions and recesses, the cable itself allows the sterilization gas to sufficiently infiltrate the contact surface and is capable of being sterilized. However, in order to perform sterilization in shorter time, an active measure for making gaps in the contact surface may be performed. That is, in formation of the support tube 13, it is desirable to apply a surface roughening process for the inside surface by using sandblasting or the like or to make the shape of the inside surface be a shape with gaps which the gas easily enters. In other words, it is desirable that gaps which gas enters are provided between the inside surface of the support tube 13 and the camera-side cable 12.

Figure 4:
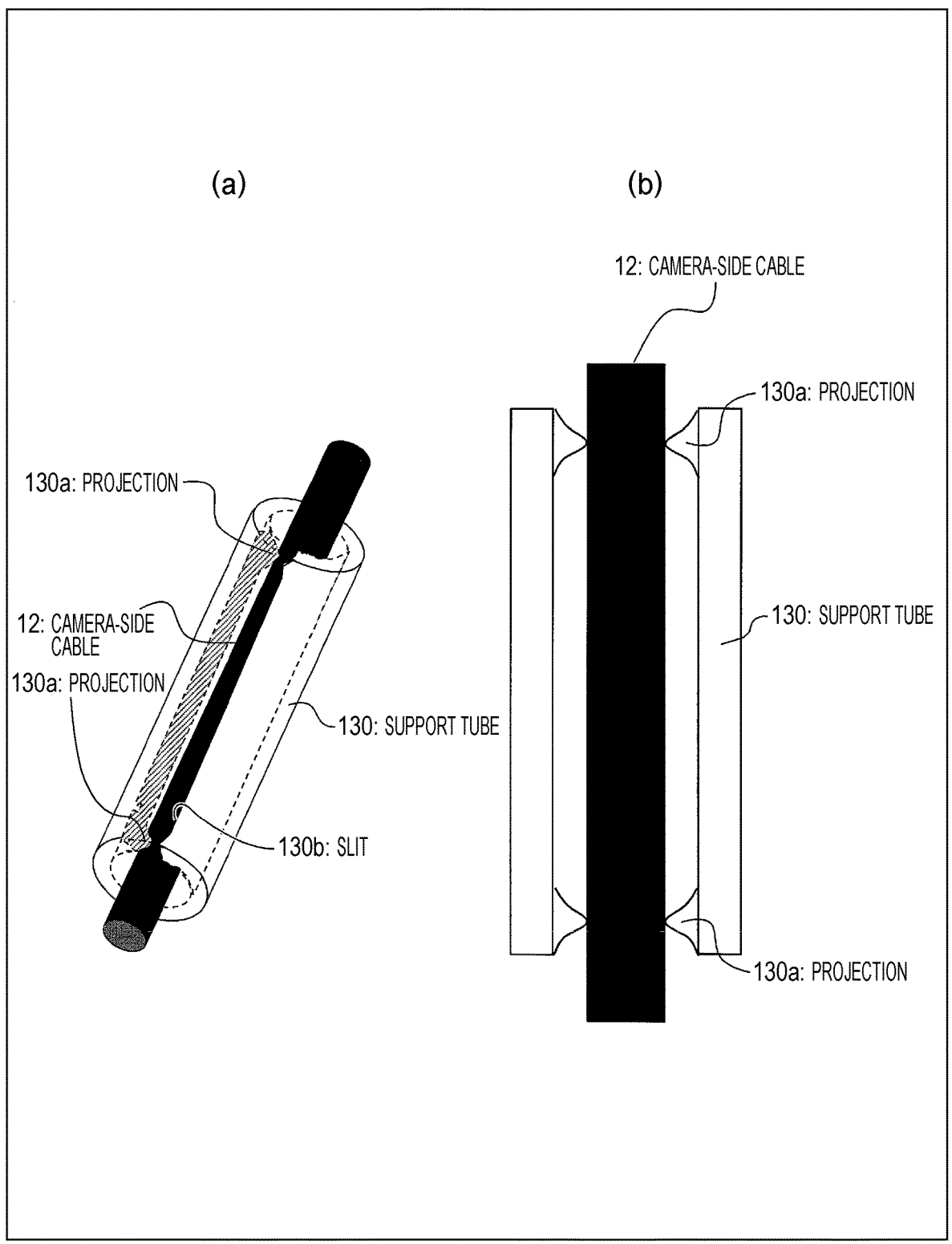
FIG. 4 is a perspective diagram (a) and an axial direction cross-sectional diagram (b) of a support tube and a camera-side cable in another configuration in the first embodiment.
Figure 5:
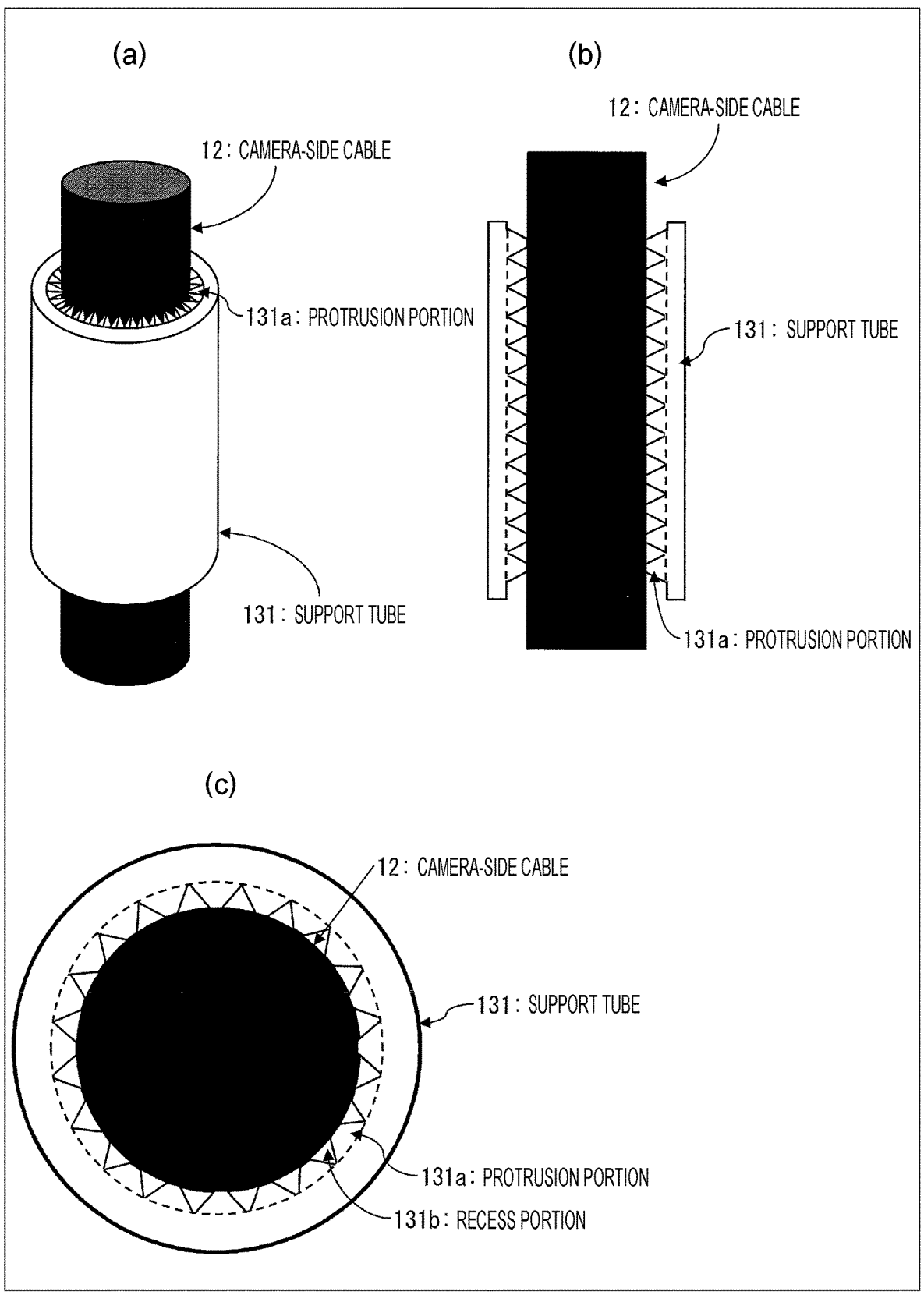
FIG. 5 is a perspective diagram (a), an axial direction cross-sectional diagram (b), and a circumferential direction cross-sectional diagram (c) of a support tube and the camera-side cable in another configuration in the first embodiment.

For example, as a support tube 130 illustrated in FIG. 4, a shape is possible in which a projection 130a is provided in one part or plural parts on the inside surface of the support tube 130 and only the portions of the projections 130a are brought into contact with the camera-side cable 12. The projection 130a may be formed in the position and shape that may secure a moderate retaining force and the gaps which gas goes into. For example, as illustrated in FIG. 4, in a case where a slit 130b is provided to the support tube 130, the projections 130a are provided at both ends of the slit 130b, the gaps which the gas infiltrates may thereby be made, and the camera-side cable 12 may thereby be prevented from being removed through the slit 130b.

Alternatively, it is possible that the support tube 13 is formed into a shape in which protrusions and recesses are provided on the inside surface to provide a shape in which only protrusion portions make contact. Specifically, as a support tube 131 illustrated in FIG. 5, many fine protrusions and recesses may be provided on the inside surface, and the moderate retaining force and the gaps which gas goes into may be provided. For example, a mesh-shaped recess portion 131b is provided on the inside surface, and a shape may thereby be formed in which protrusion portions 131a formed in meshed portions contact with the camera-side cable 12, or a shape may thereby be formed which includes corrugated recess and protrusion portions. In other words, the inside surface of the support tube 13 includes a retaining force to the extent that the support tube 13 is movable with respect to the camera-side cable 12 by an external force, does not make perfect contact, and allows gas to infiltrate the contact surface.

Further, in a case where the projection 130a or the protrusion portion 131a is provided on the inside surface in such a manner, it is desirable to flatten a surface that contacts with the camera-side cable 12 or round corners and thereby to form a shape that does not damage the camera-side cable 12.

It is desirable to consider the danger in a case where the support tube 13 is removed from the cable in a process in which the camera unit 11 is introduced into the body through the trocar 31. In a case where the support tube 13 is removed from the cable in the body and falls, it is difficult to find the support tube 13 because the support tube 13 is small in size and goes into a portion behind the organs or a gap in the body cavity. Remaining of the support tube 13 in the body possibly causes a functional disorder, infection, and so forth of a patient and causes a load. In order to avoid such risk, a configuration has to be employed in which the support tube 13 is less likely to be removed from the cable. In the first embodiment, the inside surface of the support tube 13 is brought into contact with the camera-side cable 12, and the support tube 13 is thereby caused to have a certain degree of retaining force. The inner diameter of the support tube 13 is set equal to or more than the outer diameter of the camera-side cable 12 to less than the outer diameter of the camera-side cable connector 15a, and the connector is thereby caused not to pass through but be stuck at the cable hole of the support tube 13. Accordingly, the support tube 13 is prevented from being pulled off from the camera-side cable 12.

Further, although just in case, it is desirable to consider a case where an unexpected load is exerted by an unexpected using method and the support tube 13, the camera-side cable 12, or the like is thereby damaged. In a case where the support tube 13 or the camera-side cable 12 is damaged, the support tube 13 is possibly removed from the camera-side cable 12, falls, and remains in the body even in a case where a configuration for fall prevention is employed. Accordingly, regardless of whether or not a fall prevention configuration is present, a measure has to be taken so that the position of the support tube 13 in the body may be identified. One example of position detection means of the support tube 13 in the body is X-rays. It is desirable that the support tube 13 is configured to be detectable by X-rays. In order to detect the support tube 13 by X-rays, for example, a configuration may be made which includes detection means such as embedding metal or the like which blocks or absorbs X-rays in the internal portion of the support tube 13, adding a contrast agent to a composition, and coating a contrast agent onto the support tube 13.

In the first embodiment, in formation of the support tube 13, barium sulfate that acts as an X-ray contrast agent is added as a composition, and identification of the position by using X-rays is thereby enabled. In order to perform position detection in the body by X-rays, the ratio of barium sulfate is desirably 3% to 15%. As a material for the position detection by X-rays, another material than barium sulfate, which does not have an adverse influence on a human body, may be used. Further, as the position detection means of the support tube 13, another method than X-rays may be used. For example, it is possible to use a fluorescent material, use magnetism such as MRI, use a sound wave, embed a sensor that sends out a radio signal, or the like.

Similarly, other components than the support tube 13 desirably include means for position identification in the body. Thus, similarly to the support tube 13, as a composition or a configuration material of components of the camera unit 11 or the like, a material that is detectable by X-rays may be added. Further, other position detection means than X-rays may be used. As for the above configuration, the same applies to the embodiments in the following.

Figure 6:
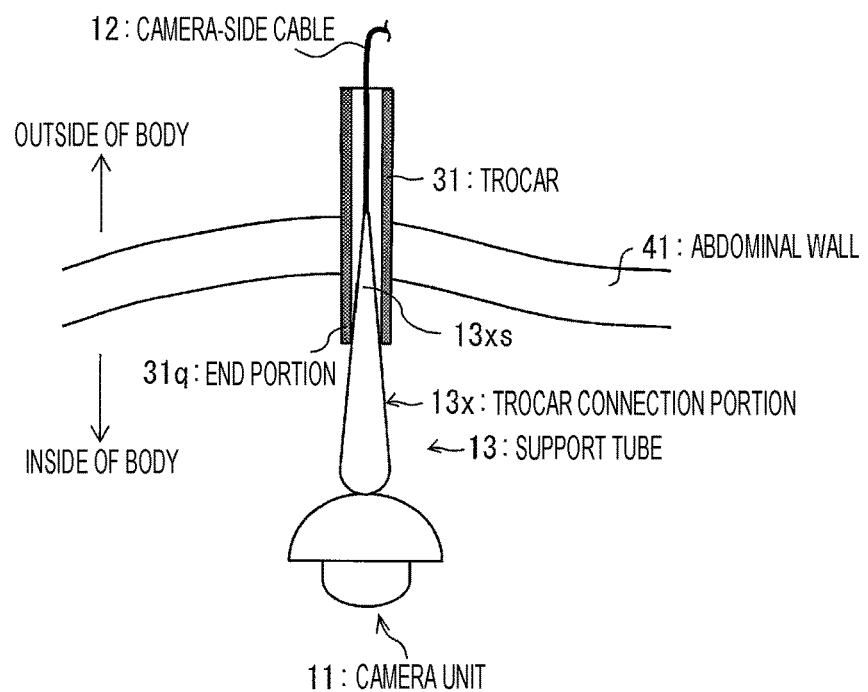
FIG. 6 is cross-sectional diagrams (a) and (b) that illustrate installation examples of the support tube, the camera unit, and a trocar in the first embodiment.
Figure 6:
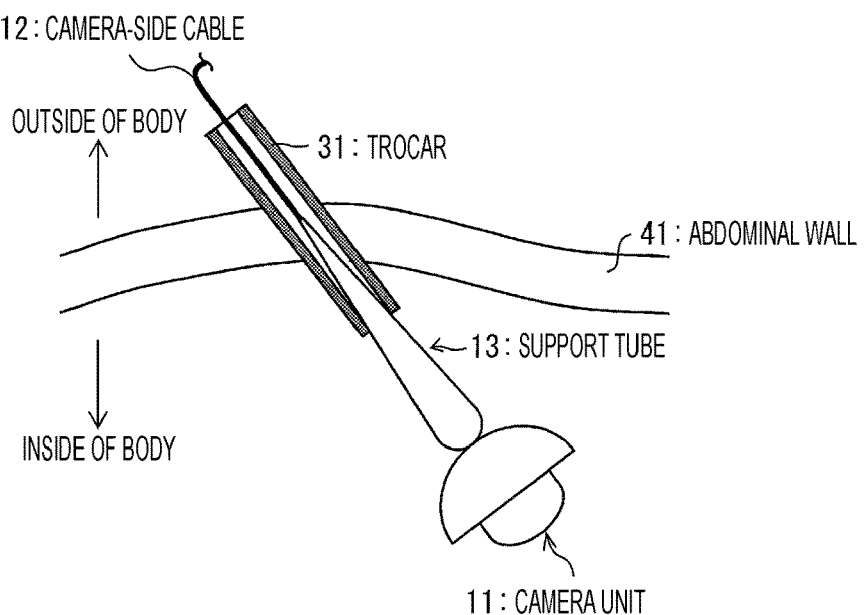
Figure 7:
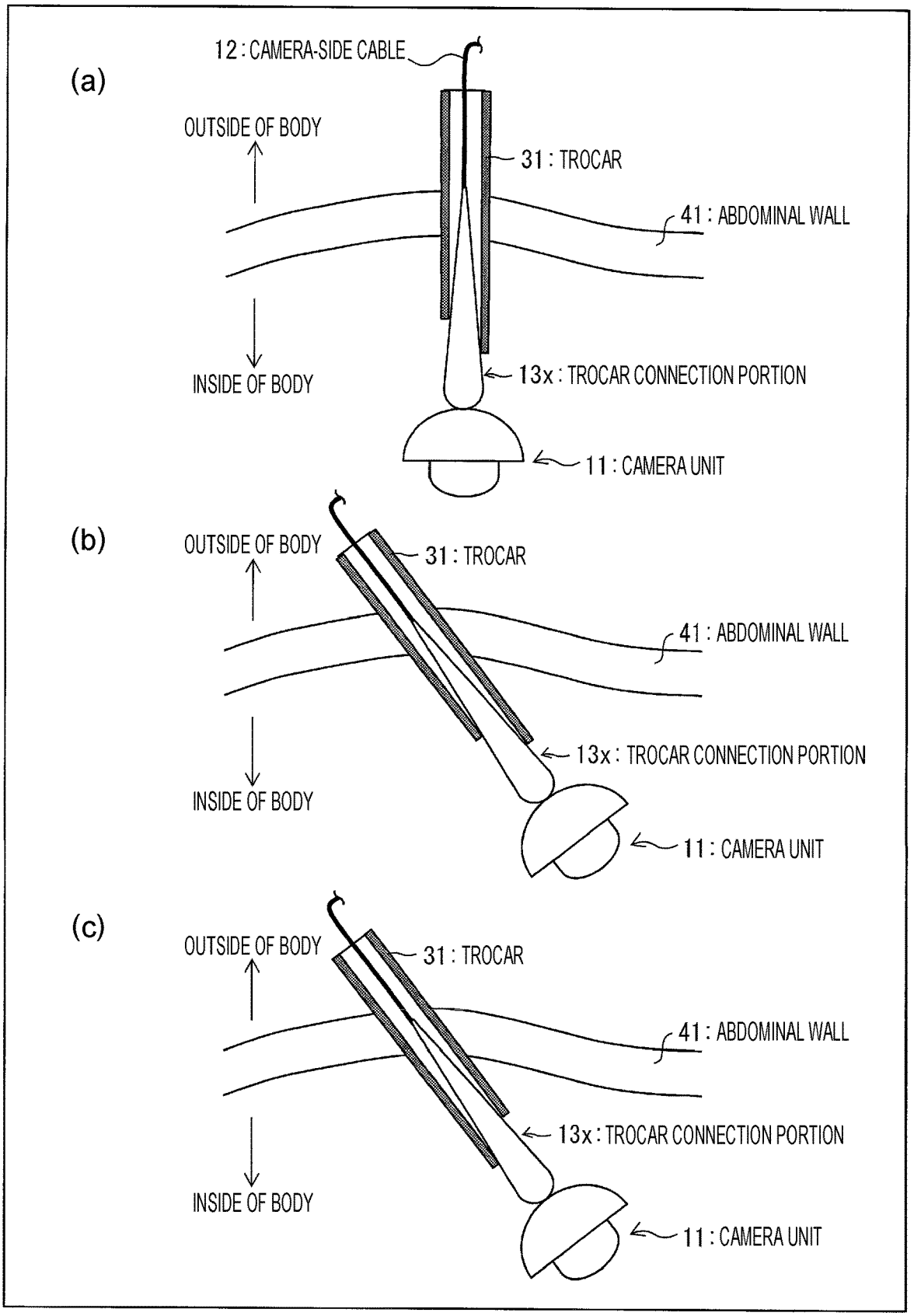
FIG. 7 is cross-sectional diagrams (a) to (c) that illustrate other installation examples of the support tube, the camera unit, and the trocar in the first embodiment.

FIG. 6 is cross-sectional diagrams (a) and (b) that illustrate installation examples of the support tube, the camera unit, and the trocar in the first embodiment. FIG. 7 is cross-sectional diagrams (a) to (c) that illustrate other installation examples of the support tube, the camera unit, and the trocar in the first embodiment. As illustrated in (a) in FIG. 6, the trocar connection portion 13x of the support tube 13 is in the conical shape that becomes thinner in the direction to approach the trocar 31, the outer diameter of an end portion on the thinner side is smaller than the inner diameter of an end portion of the trocar 31 on the inside of the body, and the outer diameter of an end portion on the thicker side is larger than the inner diameter of the end portion of the trocar 31 on the inside of the body. Accordingly, an operator draws up a portion of the camera-side cable 12 which is on the outside of the trocar 31, an end portion 13xs on the thinner side of the trocar connection portion 13x is thereby placed into an end portion 31q of the trocar 31 on the inside of the body, an outside surface of the trocar connection portion 13x abuts the inside surface of the trocar 31, and the support tube 13 is held by the trocar 31. The camera-side cable 12 is fixed to the abdominal wall 41 or the like to keep a tension of the camera-side cable 12.

Note that in a case where the orientation of the camera unit 11 has to be changed, as illustrated in (b) in FIG. 6, the operator may incline the trocar 31.

In such a manner, in a case where the support tube 13 is used, the camera-side cable 12 connected with the camera unit 11 is drawn out to the outside of the body through the support tube 13 and the trocar 31, and the camera unit 11 is drawn out together with the camera-side cable 12. Accordingly, in the body, the support tube 13 may be connected with the trocar 31, and the camera unit 11 may be joined to the support tube 13. That is, the support tube 13 joined to the camera unit 11 may be held by the trocar 31.

Consequently, the supporting force for the camera unit 11 is enhanced, connection failure between the camera unit 11 and the camera-side cable 12 is less likely to occur, and reliability is improved. Further, the operator may change the orientation of the camera unit 11 in the body by operating the trocar 31, and easiness of use is thereby improved.

Further, in the support tube 13, because the trocar connection portion 13x as a portion to be placed into the trocar is in the tapered shape, the support tube 13 may be applied to trocars with various opening sizes (sizes of end portions in the body).

Further, because the trocar connection portion 13x is in the conical shape which may be placed into an opening of the trocar, even in a case where a tip end of the trocar is an oblique cut end, as illustrated in (a) to (c) in FIG. 7, the camera unit 11 may be directed in a specific direction regardless of the angle of the cut end or the inclination of the trocar. Note that because the camera unit 11 may be separated from the trocar 31 by the support tube 13, an advantage of suppressing a temperature rise of the trocar 31 may be provided.

The trocar connection portion 13x (particularly, a surface portion) of the support tube 13 may be configured with a hard material or may be configured with a soft material with elasticity.

Note that the length (full length) of the support tube 13 is desirably 10 mm or more to 50 mm or less. It is possible that a length of less than 10 mm causes difficulty in connection with the trocar 31 or joining to the camera unit 11. It is possible that a length that exceeds 50 mm causes difficulty in handling in the body cavity or may narrow the viewing area because the position of the camera unit 11 is separated from a body wall.

Figure 8:
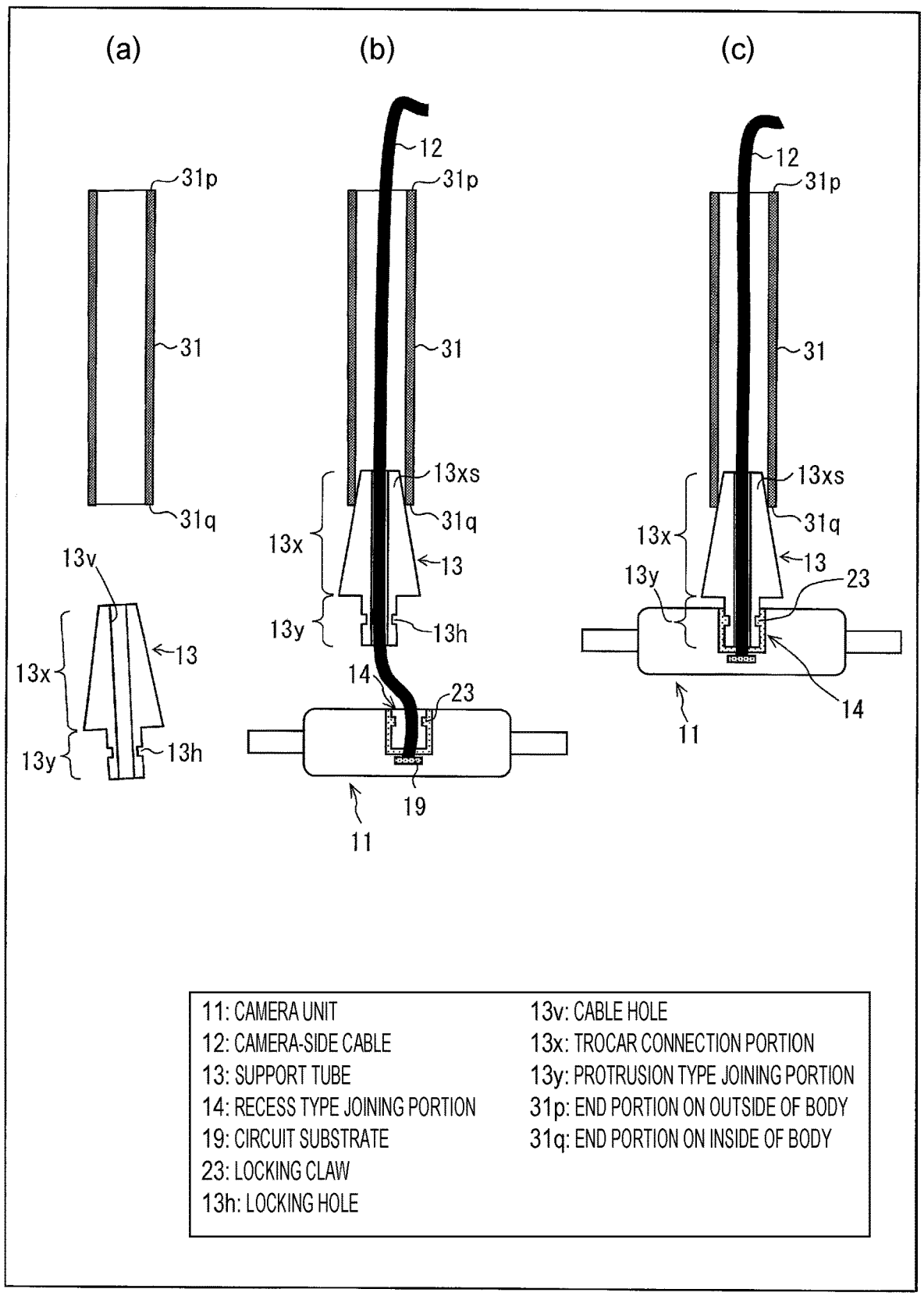
FIG. 8 is cross-sectional diagrams (a) to (c) that illustrate a connection state between the support tube and the trocar and a joining state between the support tube and the camera unit in another configuration in the first embodiment.

FIG. 8 is cross-sectional diagrams (a) to (c) that illustrate a connection state between the support tube and the trocar and a joining state between the support tube and the camera unit in another configuration in the first embodiment. The trocar connection portion 13x of the support tube 13, which is illustrated in (a) to (c) in FIG. 8, is in a truncated conical shape that becomes thinner in the direction to approach the trocar 31, the protrusion type joining portion 13y of the support tube 13 is in a columnar shape, and the outer diameter of the protrusion type joining portion 13y is smaller than the outer diameter of the end surface on the thicker side of the trocar connection portion 13x. Further, a cable hole 13v (circular opening), through which the camera-side cable 12 passes, penetrates the internal portions of the trocar connection portion 13x and the protrusion type joining portion 13y.

As illustrated in (b) and (c) in FIG. 8, the operator draws up the camera-side cable 12 (the portion that is on the outside of the trocar 31), the end portion 13xs on the thinner side of the trocar connection portion 13x is thereby inserted in the end portion 31q of the trocar 31 on the inside of the body, and the support tube 13 is thereby held by the trocar 31. Here, the recess type joining portion 14 of the camera unit 11 is fitted in the protrusion type joining portion 13y of the support tube 13, the locking claw 23 provided to the inner wall of the recess type joining portion 14 locks in a locking hole 13h provided to an outside surface of the protrusion type joining portion 13y, and the camera unit 11 is firmly held by the support tube 13. Note that a female thread or the like may be used instead of the locking claw 23.

In a state where the recess type joining portion 14 is fitted in the protrusion type joining portion 13y ((c) in FIG. 8), a gap is provided between the upper surface of the camera unit 11 and the end surface on the thicker side of the trocar connection portion 13x. In a case where the support tube 13 is separated from the camera unit 11, forceps are inserted in the gap, and the protrusion type joining portion 13y may thereby be pulled out from the recess type joining portion 14.

Figure 9:
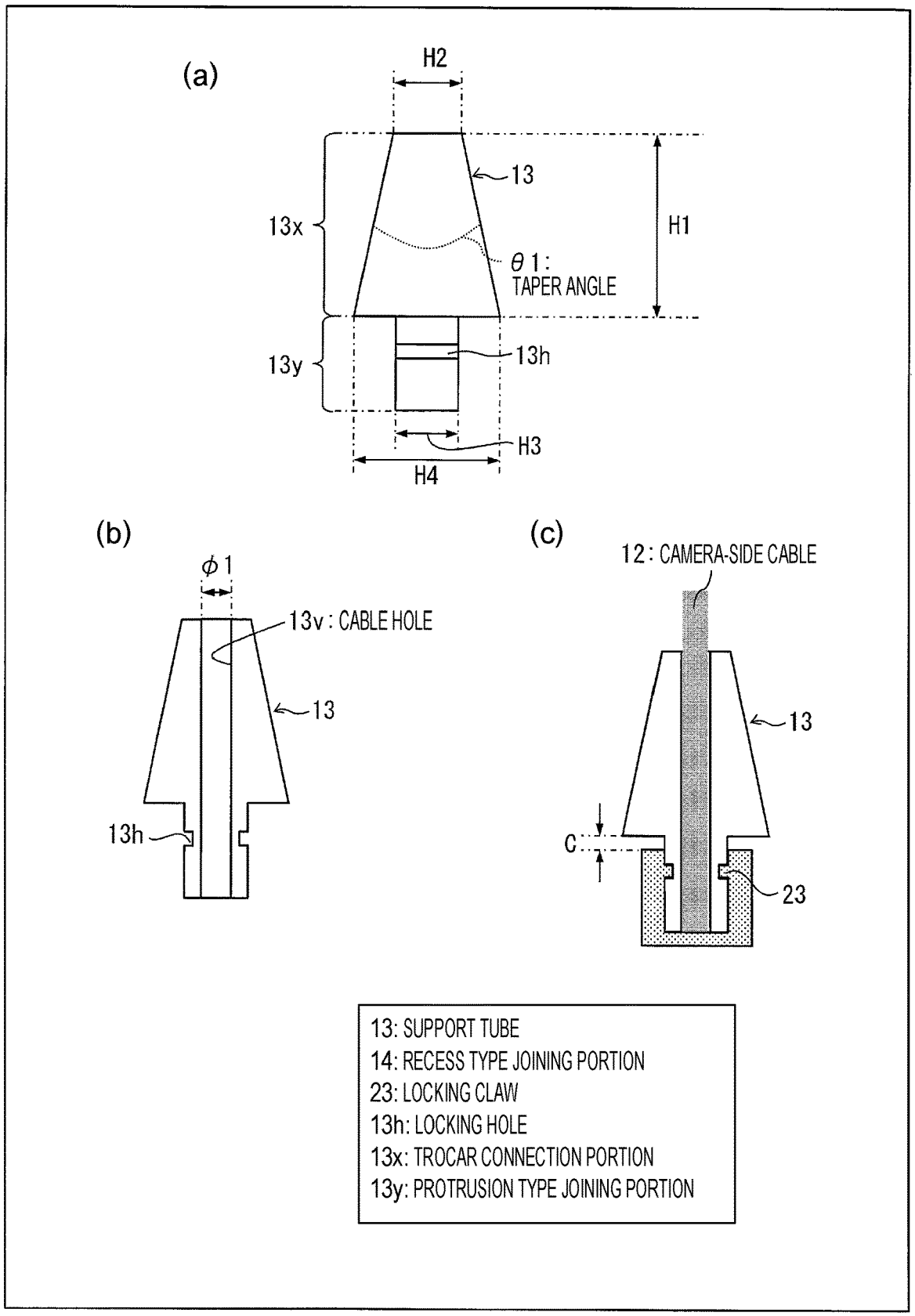
FIG. 9 is cross-sectional diagrams (a) to (c) that illustrate a size example of each portion of the support tube in the first embodiment.

FIG. 9 is cross-sectional diagrams (a) to (c) that illustrate a size example of each portion of the support tube in the first embodiment. In the first embodiment, for example, as illustrated in (a) to (c) in FIG. 9, a height H1 of the trocar connection portion 13x (truncated conical shape)=15 mm, the outer diameter H2 of the end surface on the thinner side of the trocar connection portion 13x=3 mm, the outer diameter H3 of the protrusion type joining portion 13y (columnar shape)=5.5 mm, the outer diameter H4 of the end surface on the thicker side of the trocar connection portion 13x=8 mm, and the inner diameter (the caliber of the cable hole) φ1 of the support tube 13=1.6 mm.

Further, a taper angle θ1 of the trocar connection portion 13x in the truncated conical shape is set to 5° or more to 30° or less, for example. Consequently, in a case where the tip end of the trocar 31 is an obliquely cut shape, the inclination of the camera unit 11 does not largely change even in a case where the trocar 31 is rotated, and the trocar 31 and the camera unit 11 are easy to use.

Further, a gap C between the upper surface of the camera unit 11 and the end surface on the thicker side of the trocar connection portion 13x may be set to an optimal value for separation of the camera unit 11 and the trocar connection portion 13x in accordance with the shape of tip ends of forceps, the upper surface shape of the camera unit 11, and so forth.

(Using Method of In-Vivo Monitoring Camera System)

Figure 10:
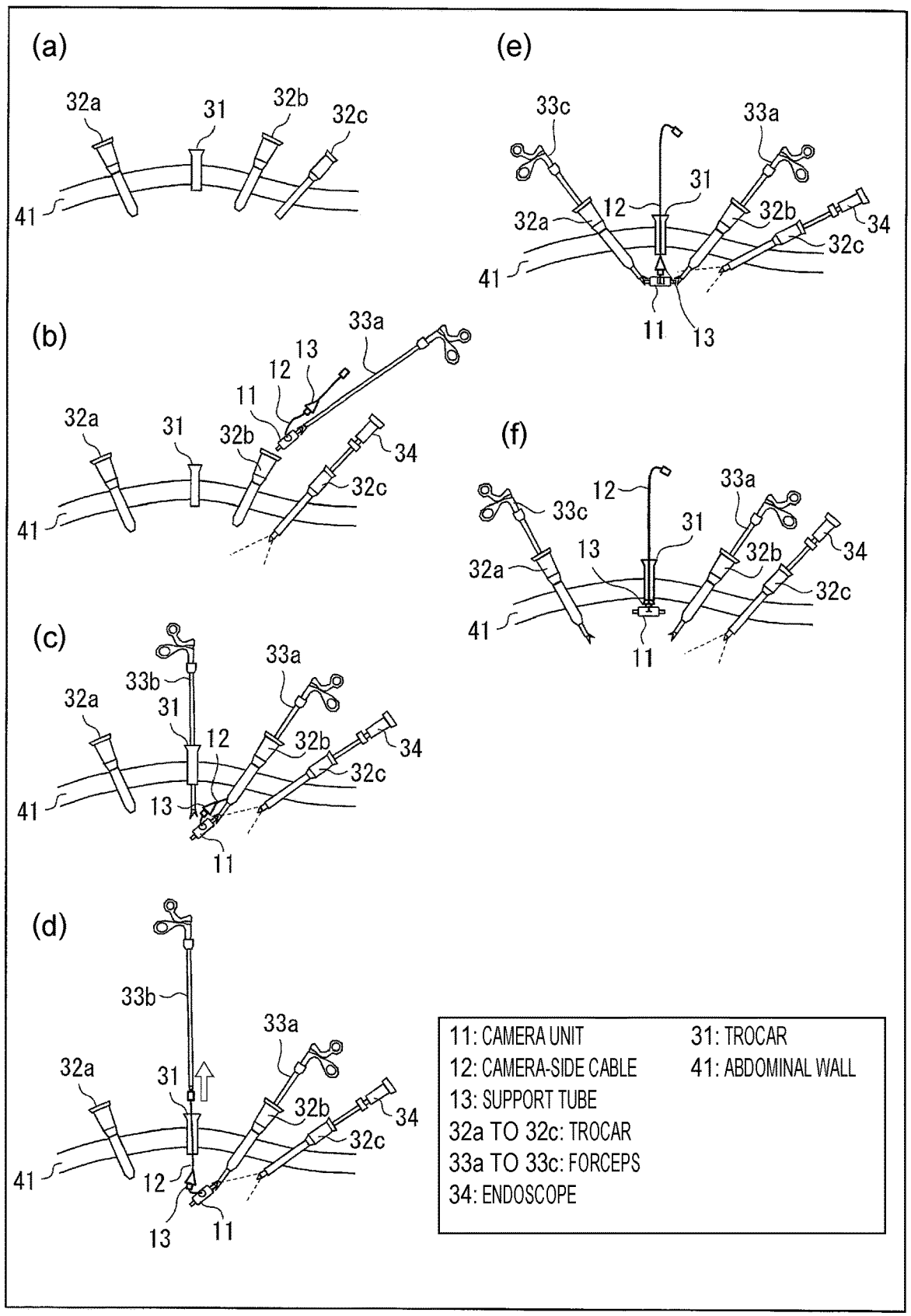
FIG. 10 is schematic diagrams (a) to (f) that illustrate use examples of the support tube, the camera unit, and trocars in the first embodiment.
Figure 11:
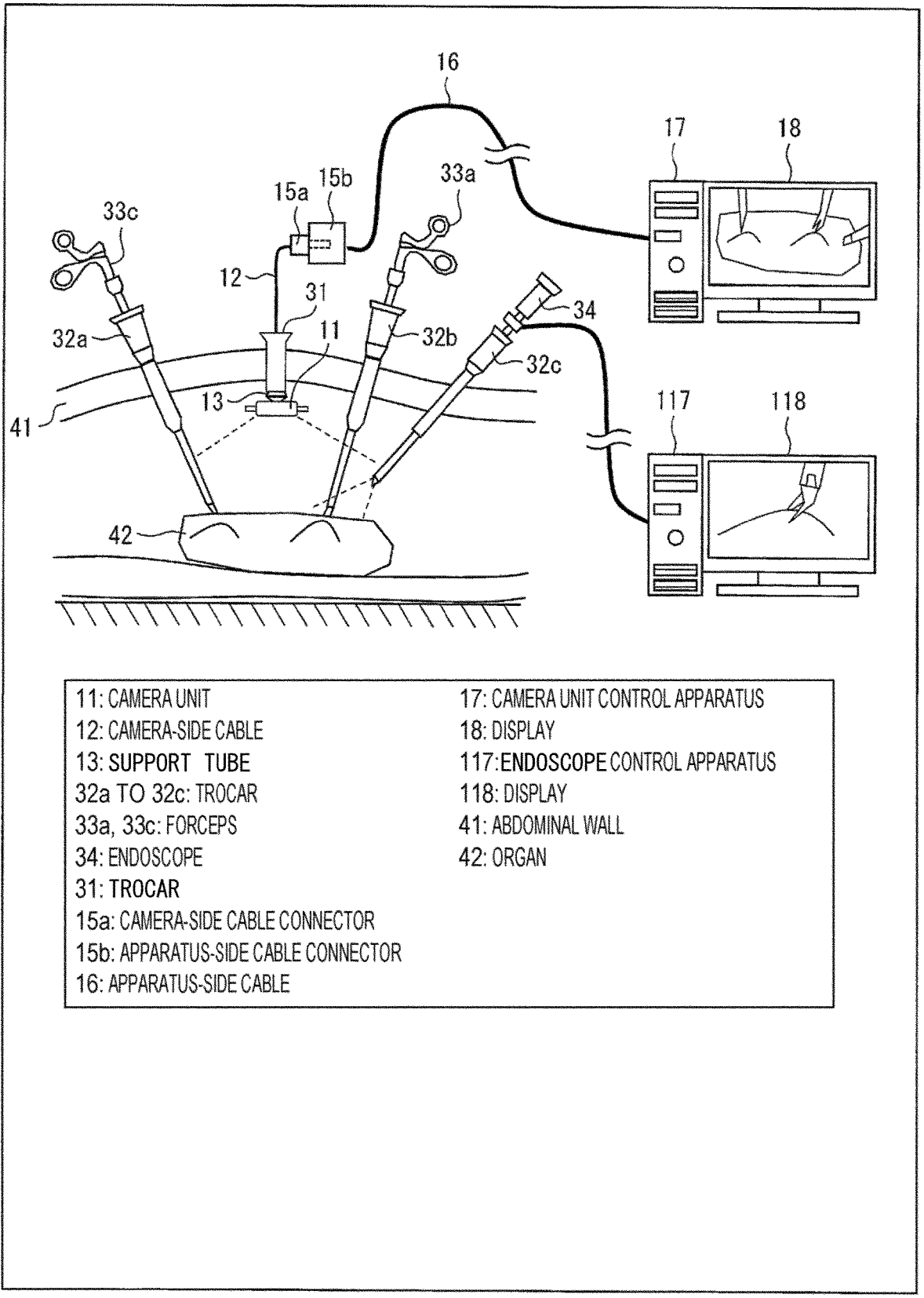
FIG. 11 is a schematic diagram that illustrates a use example of the in-vivo monitoring camera system of the first embodiment.

(a) to (f) in FIG. 10 are schematic diagrams that illustrate an installation method of the camera unit in the body in the first embodiment. FIG. 11 is a schematic diagram that illustrates a use situation of the in-vivo monitoring camera system of the first embodiment.

As illustrated in (a) in FIG. 10, the operator first opens holes (ports) for inserting forceps and an endoscope in the body cavity in the abdominal wall 41 and inserts trocars 32a to 32c in the ports. In addition, in order to install the camera unit 11 in the body cavity, the port is opened in a position in the abdominal wall 41 from which the whole organ including an affected site may be seen, and the trocar 31 is inserted therein. Specifically, in a state where a needle-shaped obturator is placed through the inside of the trocar 31, the obturator is punctured into a port position, and the trocar 31 is thereby inserted in the abdominal wall 41. Further, the trocar 31 preferably has a short diameter in order to realize minimal invasiveness. Specifically, the trocar 31 preferably has a diameter of 3 mm or less. Note that after at least one of the trocars 32a to 32c and the trocar 31 is inserted, the operator sends gas into the body through the trocar, in advance inflates the body cavity, and thereby secures a space to insert tools.

Next, as illustrated in (b) in FIG. 10, the operator inserts an endoscope 34 in the body cavity through the trocar 32c and inserts the camera unit 11 grasped by forceps 33a, the camera-side cable 12, and the support tube 13 placed around the camera-side cable 12 in the body cavity through the trocar 32b while observing the inside of the body by using the endoscope 34.

Next, as illustrated in (c) in FIG. 10, the operator moves the camera unit 11 to the vicinity of the trocar 31 by operating the forceps 33a and inserts forceps 33b in the body cavity through the trocar 31.

Next, as illustrated in (d) in FIG. 10, the operator pulls out the forceps 33b from the trocar 31 in a state where the camera-side cable 12 is pinched by the forceps 33b and thereby guides the camera-side cable 12 to the outside of the body. Here, the camera unit 11 (the grip portion thereof) is grasped by the forceps 33a.

Next, as illustrated in (e) in FIG. 10, the operator draws up the camera-side cable 12 guided to the outside of the body by forceps, a hand, or the like and thereby brings a tip end of the support tube 13 to proximity of the opening of the trocar 31.

Next, as illustrated in (f) in FIG. 10, the operator further draws up the camera-side cable 12 and the camera unit 11, thereby inserts one end (trocar connection portion) of the support tube 13 into the end portion of the trocar 31 on the inside of the body, fits the camera unit 11 in the other end (protrusion type joining portion), thereby connects the one end (trocar connection portion) of the support tube 13 with the end portion of the trocar 31 on the inside of the body, joins the other end (protrusion type joining portion) to the camera unit 11, and thereby fixes the camera-side cable 12 to the abdominal wall 41 or the like such that the tension of the camera-side cable 12 is maintained.

After the camera unit 11 is installed in the body, as illustrated in FIG. 11, connector 15a of the camera-side cable 12 is fitted in the apparatus-side cable connector 15b, and the camera-side cable 12 is thereby connected with the apparatus-side cable 16. Consequently, local pictures of a treatment site are displayed on a display 118 by an endoscope control apparatus 117, and a whole picture of the inside of an organ 42, which is photographed by the camera unit 11, is displayed on the display 18 by the camera unit control apparatus 17.

The following is performed after the use. First, the operator puts forceps 33c into the gap between the support tube 13 and the camera unit 11 in a state where the grip portion 22 of the camera unit 11 in the body is grasped by the forceps 33a and operates the forceps 33c to separate the support tube 13 from the camera unit 11. Next, the operator separates the support tube 13 from the camera unit 11 and thereafter guides the camera unit 11, the camera-side cable 12, and the support tube 13 to the outside of the body through the trocar 32b. Here, the camera-side cable connector 15a is temporarily returned into the body through the trocar 31 and is thereafter drawn out to the outside of the body through the trocar 32b.

Second Embodiment

Figure 12:
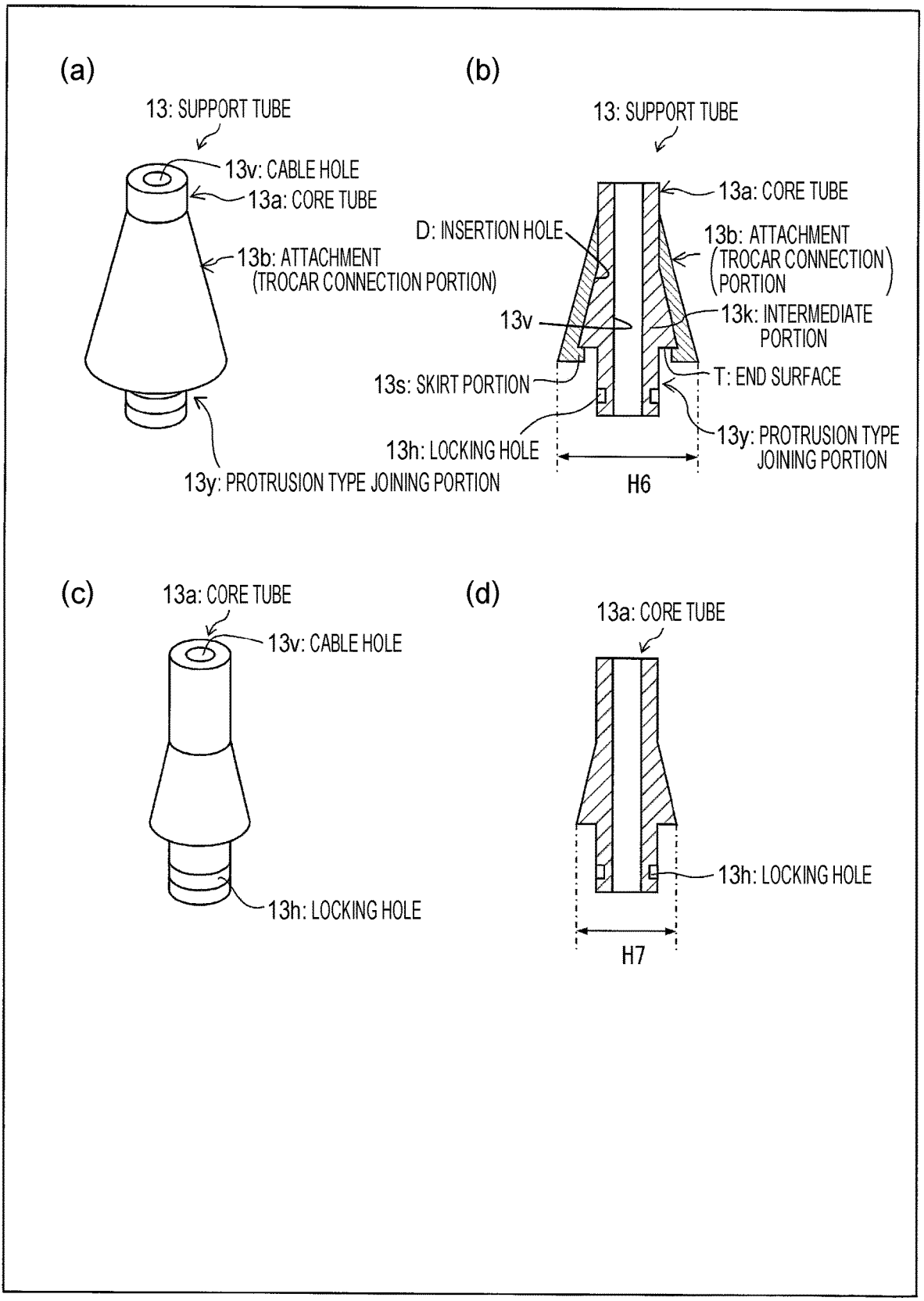
FIG. 12 is perspective diagrams (a) and (c) and cross-sectional diagrams (b) and (d) that illustrate a configuration of the support tube in a second embodiment.

FIG. 12 is perspective diagrams (a) and (c) and cross-sectional diagrams (b) and (d) that illustrate a configuration of the support tube in a second embodiment. As illustrated in (a) in FIG. 12, the support tube 13 is configured with a core tube 13a that has the cable hole 13v (circular opening) and an attachment 13b that is attached to an outside surface of the core tube 13a. A hole diameter (the inner diameter of the support tube 13) of the cable hole 13v is smaller than the outer diameter of the camera-side cable connector.

As illustrated in (b) in FIG. 12, the core tube 13a is configured with a cylinder type lower portion that functions as the protrusion type joining portion 13y, a cylinder type upper portion, and an intermediate portion 13k that is interposed between the lower portion and the upper portion. The intermediate portion 13k is a truncated conical shape in which an upper portion side is thinner than a lower portion side, and the outer diameter of an end surface T on the lower portion side of the intermediate portion 13k is larger than the outer diameter of the lower portion.

The attachment 13b is in a truncated conical shape that has an insertion hole D (circular opening). The insertion hole D has the shape that corresponds to the intermediate portion 13k of the core tube 13a, and the intermediate portion 13k is fitted in the insertion hole D from a lower side thereof. Further, a skirt portion 13s of the attachment 13b is folded inward along the end surface T on the lower portion side of an intermediate portion 13k, and the attachment 13b is thereby mounted on the core tube 13a. Here, an outer diameter H6 of an end surface on the thicker side of the attachment 13b is set to 8.0 mm, and an outer diameter H7 of the end surface T of the lower portion side of the intermediate portion 13k is set to 4.9 mm or less. Here, the attachment 13b is configured such that the camera-side cable connector 15a may be placed through the inside of the insertion hole D.

Note that in the core tube 13a, the lower portion on which the attachment 13b is not mounted serves as the protrusion type joining portion 13y, and the locking hole 13h that corresponds to the locking claw of the recess type joining portion of the camera unit is formed in the protrusion type joining portion 13y.

In the second embodiment, the support tube 13 is formed with two components that are the core tube 13a and the attachment 13b, and those are assembled. However, as for the components that form the support tube 13, a configuration is possible in which the core tube 13a and the attachment 13b are divided into much more components. The same applies to the embodiments in the following.

Figure 13:
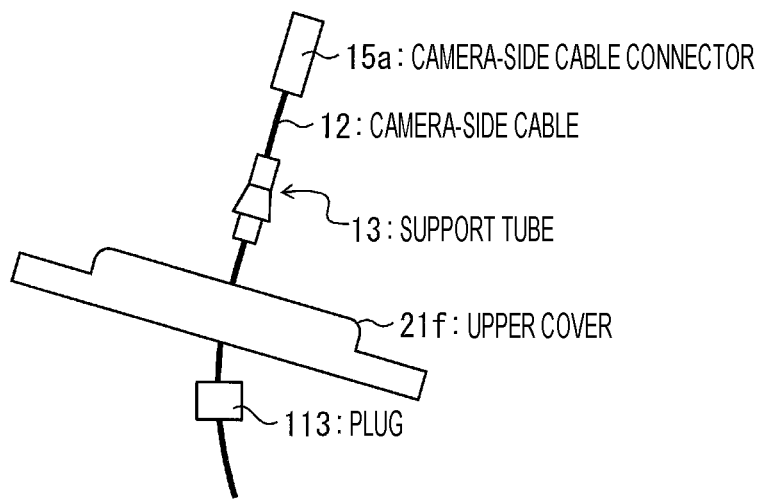
FIG. 13 is cross-sectional diagrams (a) to (c) that illustrate the relationship among the camera unit, the support tube, and the camera-side cable in manufacturing steps in the second embodiment.
Figure 13:
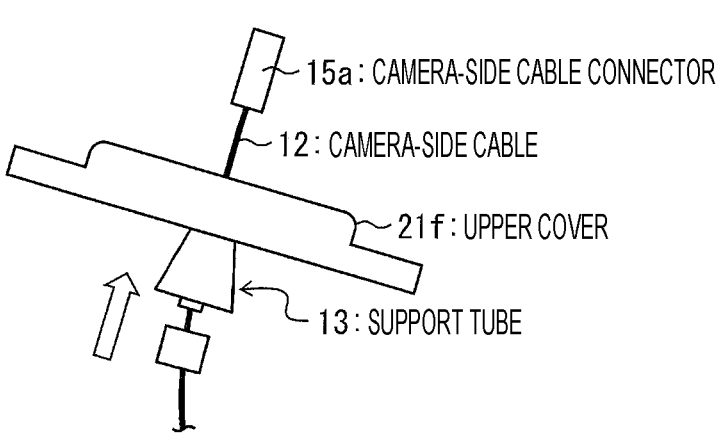
Figure 13:
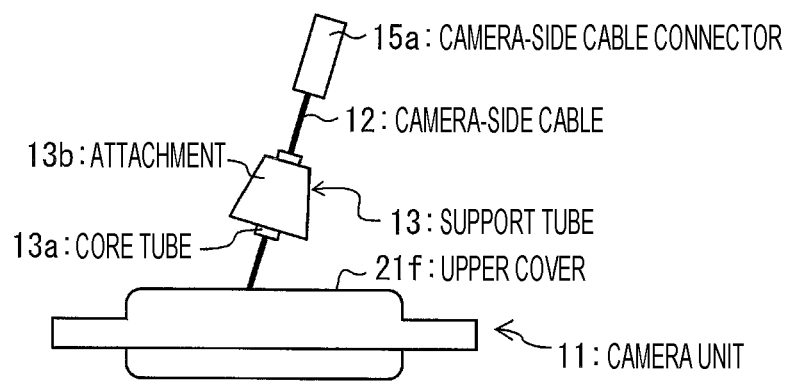

FIG. 13 is cross-sectional diagrams (a) to (c) that illustrate the relationship among the camera unit, the support tube, and the camera-side cable in manufacturing steps in the second embodiment. In a case where the outer diameter of the support tube 13 is smaller than an opening of an upper cover 21f of the camera unit 11, as illustrated in (a) in FIG. 13, the opening may be clogged by a plug 113 after the support tube 13 is placed through the opening of the upper cover 21f. However, in a case where the outer diameter of the support tube 13 is larger than the opening of the upper cover 21f of the camera unit 11, as illustrated in (b) in FIG. 13, the support tube 13 may not be placed through the opening of the upper cover 21f of the camera unit 11. In such a case, as illustrated in (c) in FIG. 13, the core tube 13a is placed through the opening of the upper cover 21f of the camera unit 11, the attachment 13b placed through from the camera-side cable connector 15a side is thereafter mounted on the core tube 13a, and the support tube 13 may thereby be configured.

Figure 14:
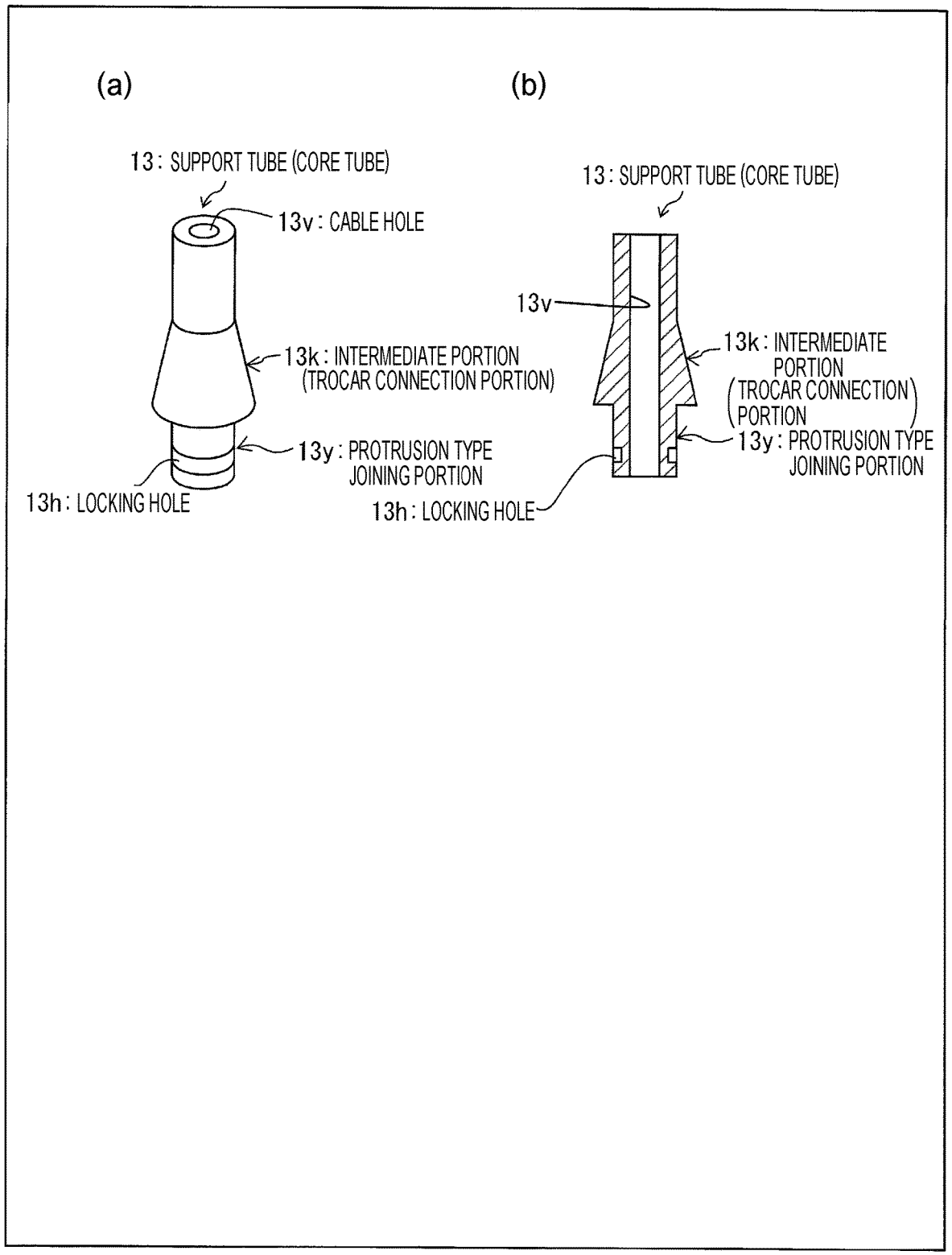
FIG. 14 is a perspective diagram (a) and a cross-sectional diagram (b) that illustrate another configuration of the support tube in the second embodiment.

FIG. 14 is a perspective diagram (a) and a cross-sectional diagram (b) that illustrate another configuration of the support tube in the second embodiment. As illustrated in (a) and (b) in FIG. 14, the single core tube 13a illustrated in FIG. 12 may be used as the support tube 13. In this case, the intermediate portion 13k in the truncated conical shape serves as the trocar connection portion, and the lower portion serves as the protrusion type joining portion 13y.

Figure 15:
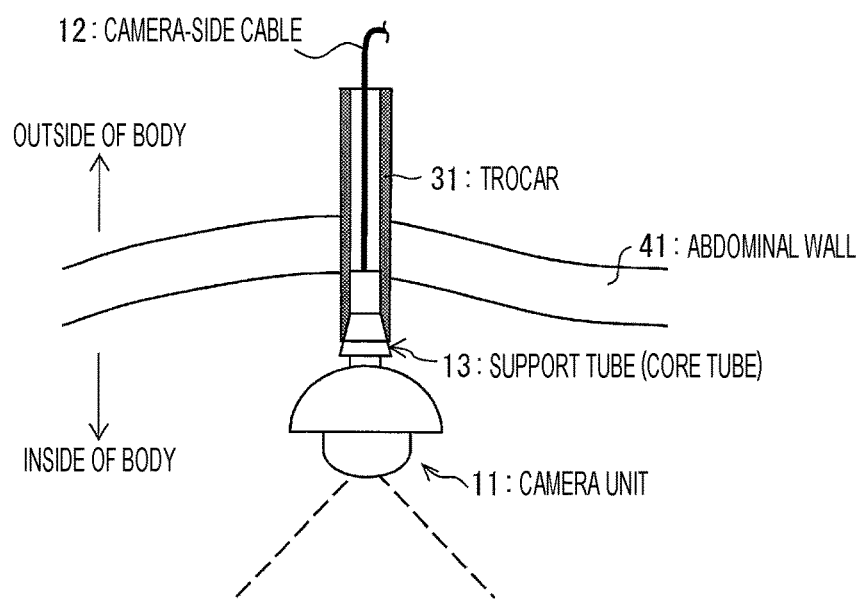
FIG. 15 is cross-sectional diagrams (a) and (b) that illustrate installation examples of the support tube, the camera unit, and the trocar in the second embodiment.
Figure 15:
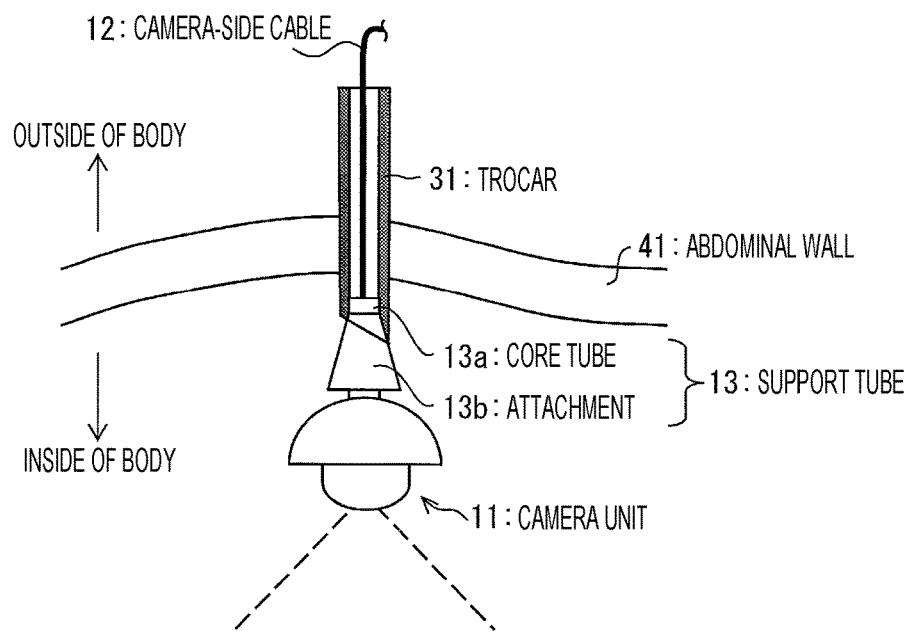

FIG. 15 is cross-sectional diagrams that illustrate installation examples of the support tube, the camera unit, and the trocar in the second embodiment. As illustrated in (a) in FIG. 15, for the trocar which is thin (a caliber of 3 mm or the like) and whose opening on the inside of the body is a horizontal cut end, the support tube 13 (configured only with the core tube) in FIG. 14 may be used. Further, as illustrated in (b) in FIG. 15, for the trocar which is thick (a caliber of 5 mm or the like) and whose opening on the inside of the body is an oblique cut end, the support tube 13 (configured with the core tube and the attachment) in FIG. 12 may be used.

Figure 16:
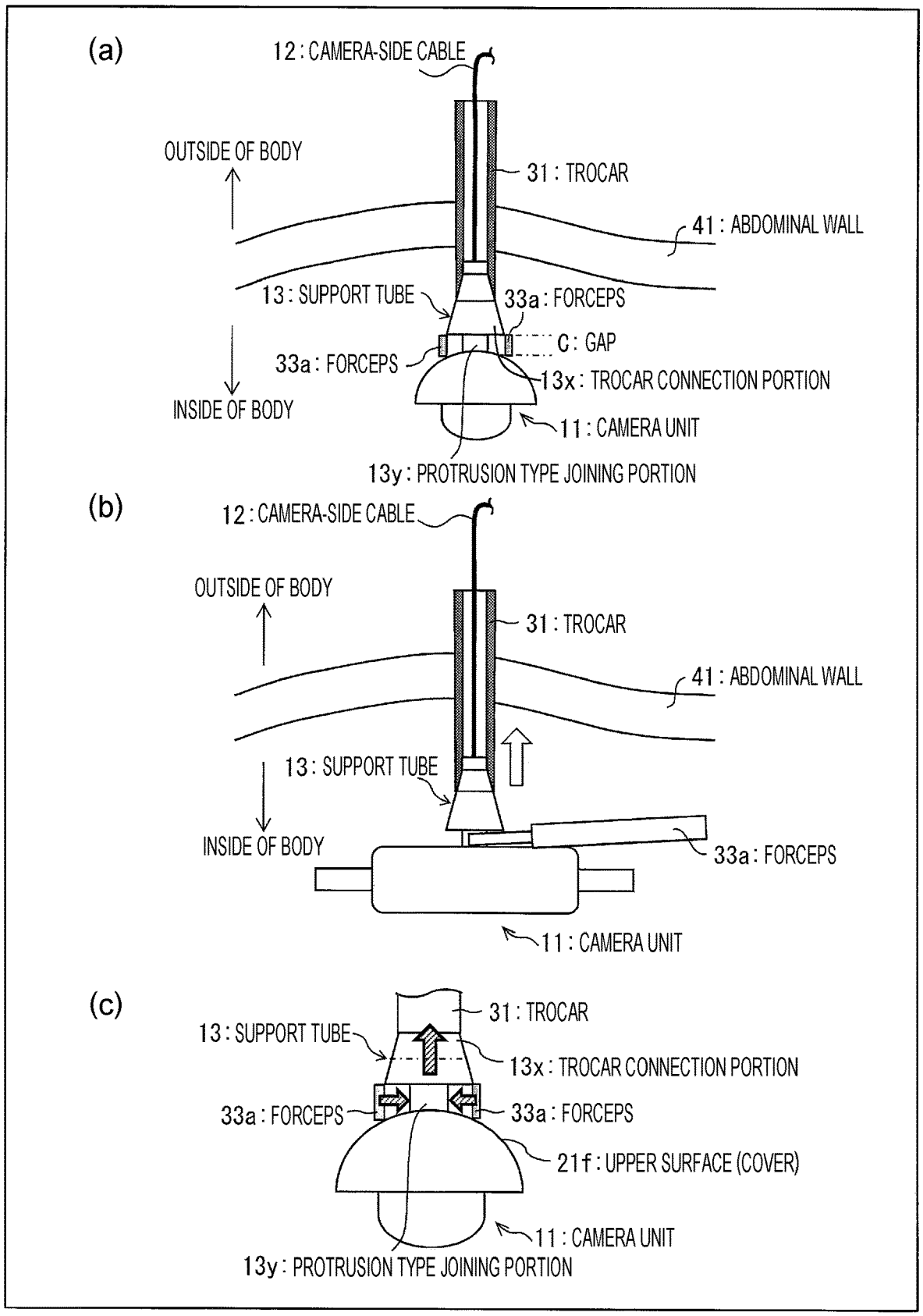
FIG. 16 is side cross-sectional diagrams (a) and (c) and a front cross-sectional diagram (b) that illustrate separation steps between the camera unit and the support tube and a configuration which facilitates the separation steps in the second embodiment.

FIG. 16 is side cross-sectional diagrams (a) and (c) and a front cross-sectional diagram (b) that illustrate separation steps between the camera unit and the support tube and a configuration which facilitates the separation steps in the second embodiment. After the support tube 13 (configured with the core tube and the attachment) in FIG. 12 is used, as illustrated in (a) to (c) in FIG. 16, two tip ends of the forceps 33a are placed into the gap between the upper surface (cover) of the camera unit 11 and the trocar connection portion 13x such that the tip ends are positioned on both sides of the protrusion type joining portion 13y of the support tube 13, the two tip ends of the forceps 33a are closed, the support tube 13 thereby moves upward, and the camera unit 11 may be separated from the support tube 13. As illustrated in (c) in FIG. 16, this is because the upper cover 21f of the camera unit 11 curves so as to be protruded toward the support tube 13 side and the gap C becomes smaller as the upper cover 21f approaches the protrusion type joining portion 13y.

Figure 17:
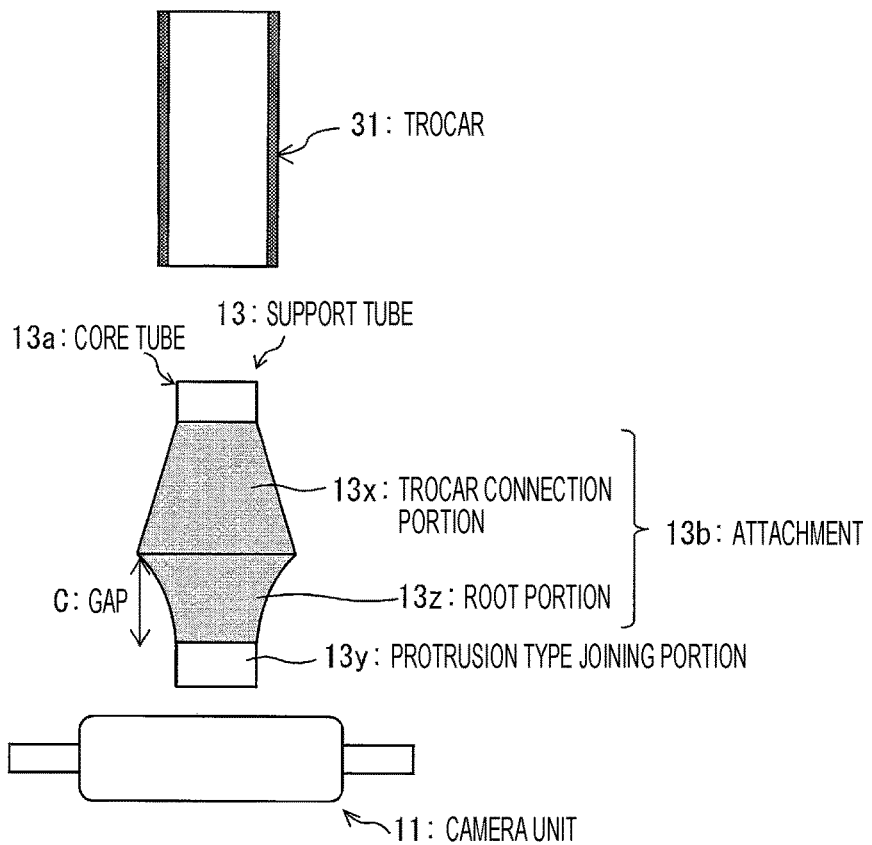
FIG. 17 is a front diagram (a) and a cross-sectional diagram (b) that illustrate still another configuration of the support tube in the second embodiment.
Figure 17:
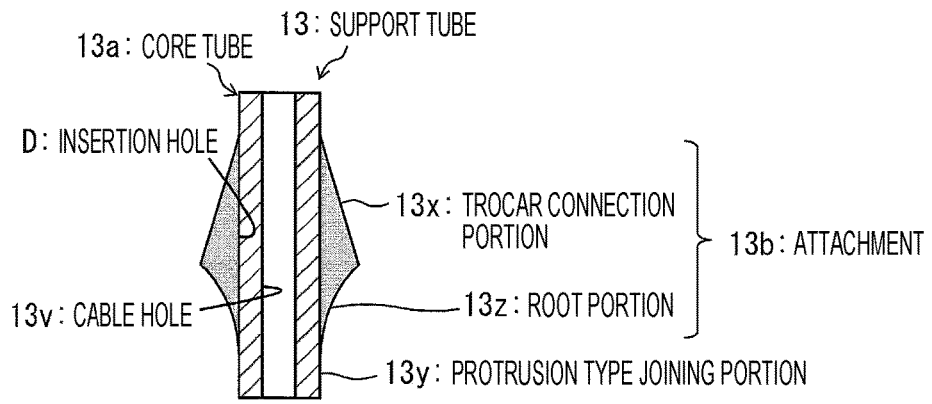

FIG. 17 is a front diagram (a) and a cross-sectional diagram (b) that illustrate still another configuration of the support tube in the second embodiment. As illustrated in (a) and (b) in FIG. 17, the support tube 13 is configured with the pipe-shaped core tube 13a that has the cable hole 13v and the attachment 13b that is attached to the outside surface of the core tube 13a.

The attachment 13b is in a spindle shape that has the insertion hole D and is formed with the trocar connection portion 13x in a truncated conical shape that becomes thinner in the direction to approach the trocar 31 and a root portion 13z in a tapered shape that becomes thinner in the direction to approach the camera unit 11. Further, the support tube 13 is configured by fitting the core tube 13a in the insertion hole D of the attachment 13b and thereby mounting the attachment 13b on the core tube 13a.

Note that in the core tube 13a, the lower portion (an end portion on the camera unit 11 side) on which the attachment 13b is not mounted serves as the protrusion type joining portion 13y.

In the support tube 13 in FIG. 17, because the root portion 13z is in a shape in which a side surface of a truncated cone is curved inward, in a case where the support tube 13 is joined to the camera unit 11, the gap C between the upper surface of the camera unit 11 and an outside surface of the root portion 13z becomes smaller as the gap C approaches the protrusion type joining portion 13y. Thus, two tip ends of forceps are placed into this gap C, those are closed, the support tube 13 thereby moves upward, and the camera unit 11 may easily be separated from the support tube 13.

In the second embodiment, the fitting force between the core tube 13a and the attachment 13b is set larger than the joining force between the camera unit 11 and the support tube 13, and the possibility that the core tube 13a is split from the attachment 13b in the body may thereby be reduced.

In the second embodiment, the support tube 13 is formed with the combination of the core tube 13a and the attachment 13b, and fall of the support tube 13 to the inside of the body is thereby prevented. However, although just in case, even in a case such a measure is taken, it is desirable to consider a case where an unexpected load is exerted on the camera-side cable 12 or the support tube 13, which is illustrated in FIG. 1, by an unexpected using method, and the camera-side cable 12 is thereby cut, or configuration components of the support tube 13 are thereby damaged. In such a case, the support tube 13 falls to the inside of the body, and remaining of the support tube 13 possibly occurs. Accordingly, the support tube 13 has to include a method for detecting the position in the body in addition to fall prevention.

Further, in the second embodiment, the support tube 13 is configured with two configuration components. In a case where the support tube 13 is disassembled and falls to the inside of the body due to an unexpected reason, both of the configuration components have to be capable of being detected. Accordingly, the position detection means has to be included in both of the core tube 13a and the attachment 13b. Further, in a case where the configuration is made in which the configuration components of the support tube are divided into much more kinds, each of all the configuration components also has to include detection means. Similarly to the first embodiment, possible position detection means is a method that uses X-rays.

In the second embodiment, both of the core tube 13a and the attachment 13b are formed by adding barium sulfate that acts as the X-ray contrast agent to compositions. The shapes, thicknesses, and so forth are different between the core tube 13a and the attachment 13b. Accordingly, in a case where the content rate of barium sulfate is set to a similar degree for the core tube 13a and the attachment 13b, how those are seen by X-rays becomes different. In the second embodiment, the core tube 13a is in a thin cylindrical shape, but the attachment 13b is in a tapered shape and a thick shape. In this case, in a case where the content rate of the contrast agent is set to a similar degree, the blocking amount of X-rays of the core tube 13a in the thin cylindrical shape is small and comparatively difficult to detect compared to the thick attachment 13b. The content rate of barium sulfate included in the core tube 13a is set higher than the attachment 13b, and thereby detection of the both components in the body is similarly made easy. If the core tube 13a is in a thick shape and the attachment 13b is thin or small, much more barium sulfate may be added to the attachment 13b.

In such a manner, in a case where the support tube 13 is configured with plural components, a different ratio may be set for the contrast agent included in each of the components in accordance with the shape or size. Further, as the position detection means of the support tube 13, the core tube 13a, and the attachment 13b, another method than X-rays may be used. The position detection means is desirably a common method in consideration of complexity or trouble in actual position detection work. However, each of the configuration components may include different position detection means. For example, a configuration is possible in which the core tube 13a may be detected by magnetism and the attachment 13b may be detected by X-rays.

Further, in a case where the camera unit 11 or the camera-side cable connector 15a is damaged, it is possible that a component or a fragment thereof falls to the inside of the body and remains there. Thus, other components than the support tube 13 desirably include the detection means by X-rays. Further, those components may include other position detection means than X-rays.

Further, in the second embodiment, a material with high thermal conductivity (for example, metal) is used for the core tube 13a that is an inside part of the support tube 13, an insulating material (for example, resin) is used for the attachment 13b that is an outside part, heat dissipation of the camera unit 11 may thereby be enhanced, the attachment 13b that possibly touches the body may thereby be insulated, and safety may be enhanced.

Further, a slit is provided to the attachment 13b, gas that pressurizes the inside of the body cavity is released from the slit, and an improvement in the heat dissipation by air flow may thereby be intended. Note that the slit provided to the attachment 13b may be a full slit that longitudinally crosses the attachment 13b from one opening to the other opening of the attachment 13b or may be a partial slit that does not reach the other opening.

Third Embodiment

Figure 18:
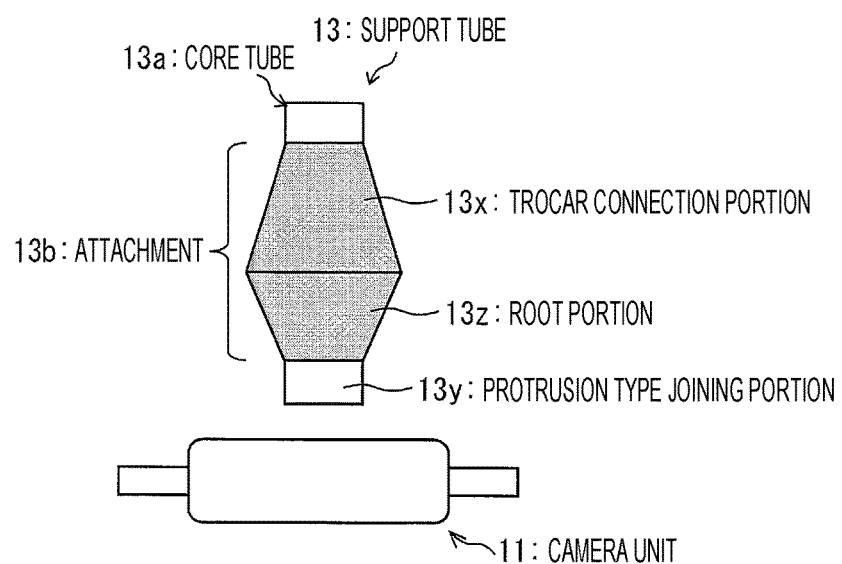
FIG. 18 is a front diagram (a) and a cross-sectional diagram (b) that illustrate a configuration of the support tube in a third embodiment.
Figure 18:
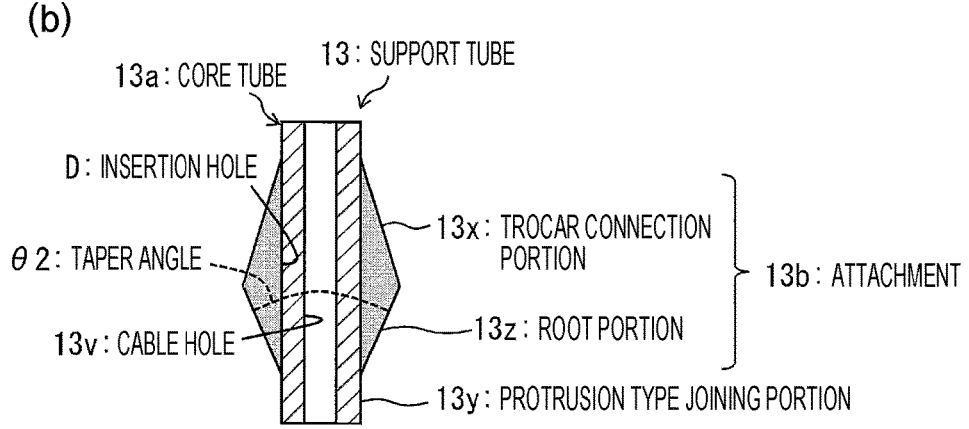

FIG. 18 is a front diagram (a) and a cross-sectional diagram (b) that illustrate a configuration of the support tube in a third embodiment. As illustrated in (a) and (b) in FIG. 18, the support tube 13 is configured with the pipe-shaped core tube 13a that has the cable hole 13v (circular opening) and the attachment 13b that is attached to the outside surface of the core tube 13a. The hole diameter (the inner diameter of the support tube 13) of the cable hole 13v is smaller than the outer diameter of the camera-side cable connector.

The attachment 13b is in a spindle shape that has the insertion hole D (circular opening) and is formed with the trocar connection portion 13x in a truncated conical shape that becomes thinner in the direction to approach the trocar 31 and the root portion 13z in a truncated conical shape that becomes thinner in the direction to approach the camera unit 11. Further, the support tube 13 is configured by fitting the core tube 13a in the insertion hole D of the attachment 13b and thereby mounting the attachment 13b on the core tube 13a. Here, the attachment 13b is configured such that the camera-side cable connector 15a may be placed through the inside of the insertion hole D.

Note that in the core tube 13a, the lower portion (an end portion on the camera unit 11 side) on which the attachment 13b is not mounted serves as the protrusion type joining portion 13y.

Figure 19:
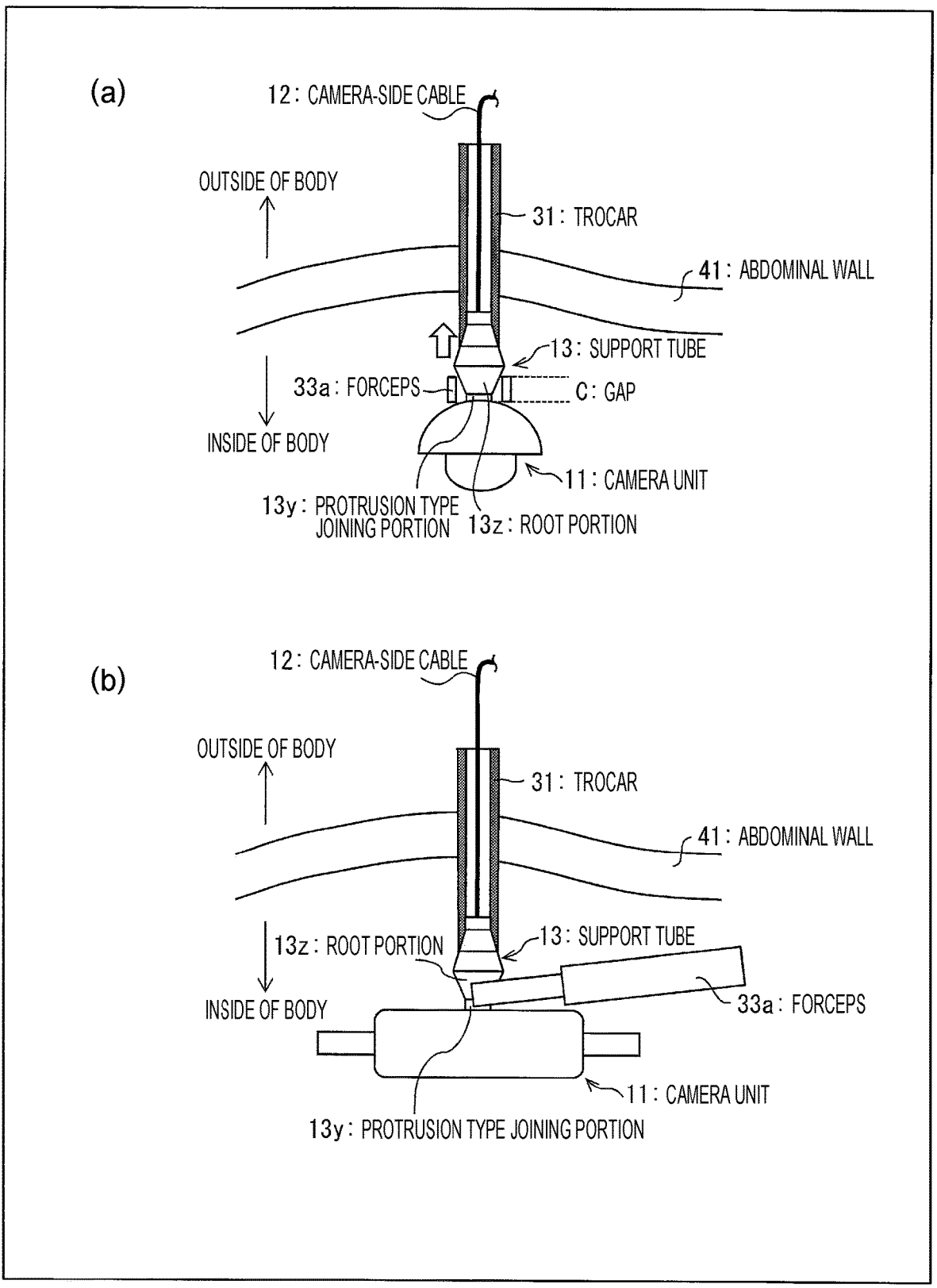
FIG. 19 is a side cross-sectional diagram (a) and a front cross-sectional diagram (b) that illustrate separation steps between the camera unit and the support tube in the third embodiment.

FIG. 19 is a side cross-sectional diagram (a) and a front cross-sectional diagram (b) that illustrate separation steps between the camera unit and the support tube in the third embodiment. In the support tube 13 in FIG. 18, because the root portion 13z is in a truncated conical shape, in a case where the support tube 13 is joined to the camera unit 11 as illustrated in (a) and (b) in FIG. 19, the gap C between the upper surface of the camera unit 11 and the outside surface of the root portion 13z becomes smaller as the gap C approaches the protrusion type joining portion 13y. Thus, the two tip ends of the forceps 33a are placed into the gap C, those are closed, the support tube 13 thereby moves upward, and the camera unit 11 may easily be separated from the support tube 13.

Figure 20:
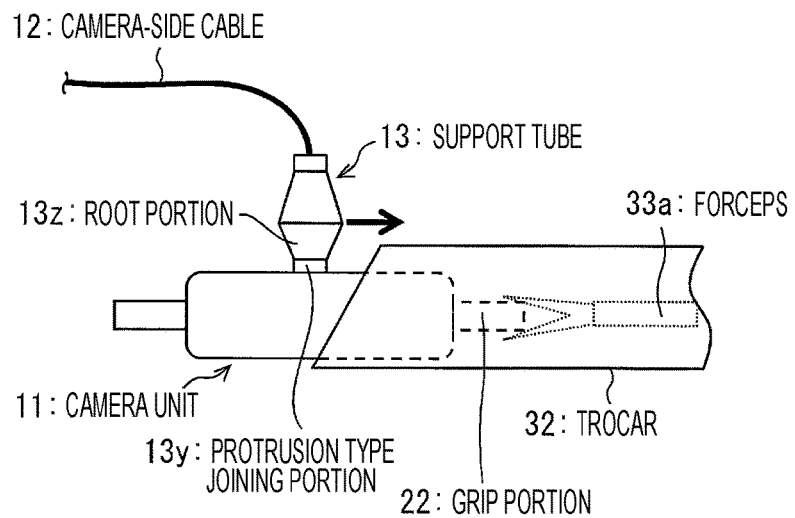
FIG. 20 is cross-sectional diagrams (a) and (b) that illustrate other separation steps between the camera unit and the support tube in the third embodiment.
Figure 20:
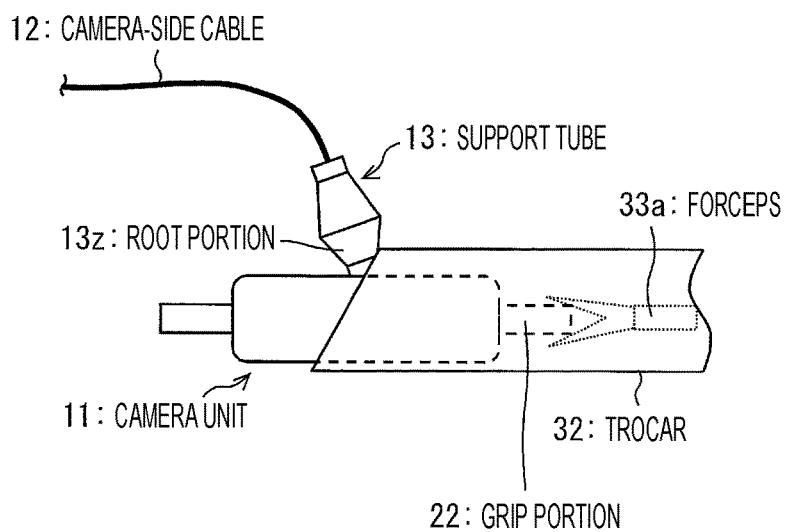

FIG. 20 is cross-sectional diagrams (a) and (b) that illustrate other separation steps between the camera unit and the support tube in the third embodiment (a case where the support tube is removed from the trocar before the support tube is removed from the camera unit). First, as illustrated in (a) in FIG. 20, a trocar 32 (the trocar 32b or the trocar 32c in FIGS. 10 and 11) used for inserting the forceps and the endoscope into the body is used for collection, the grip portion 22 of the camera unit 11 is pinched by the forceps 33a, and the camera unit 11 is drawn into an internal portion of the trocar 32. Accordingly, simultaneously with a draw-out operation, the outside surface of the root portion 13z abuts (is caught) an opening of the collection trocar 32, an upward (the direction perpendicular to the upper surface of the camera unit 11) force is added to the support tube 13, and the support tube 13 may thereby be removed from the camera unit 11.

Here, it has been known that setting a taper angle θ2 of the root portion 13z (truncated conical shape) illustrated in (b) in FIG. 18 to 15° or more to 45° or less is preferable for various trocars.

Figure 21:
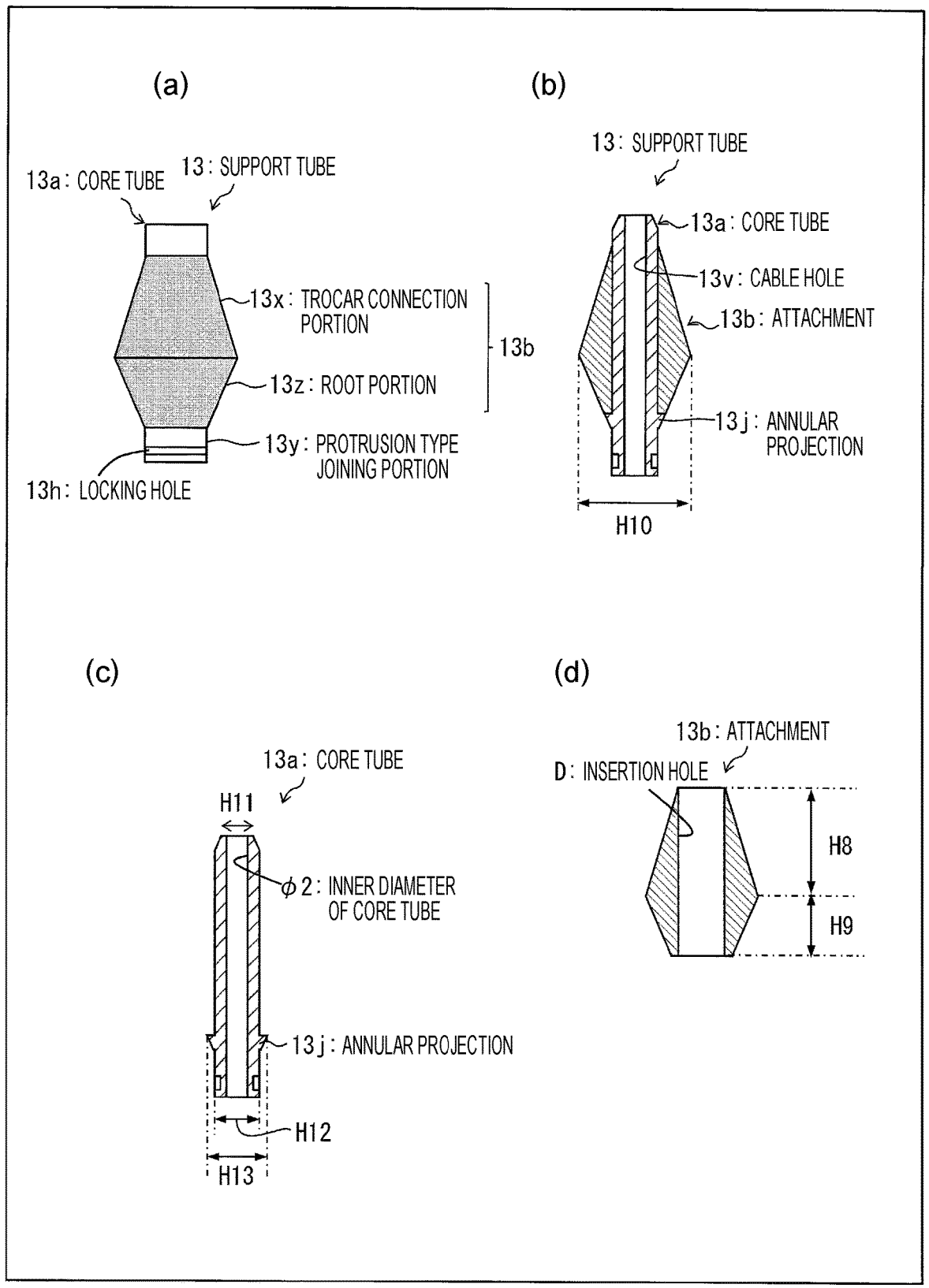
FIG. 21 is a front diagram (a) and cross-sectional diagrams (b) to (d) that illustrate a specific example of the support tube of FIG. 18.

FIG. 21 is a front diagram (a) and cross-sectional diagrams (b) to (d) that illustrate a specific example of the support tube of FIG. 18. As illustrated in (a) in FIG. 21, the support tube 13 of the third embodiment is configured with the pipe-shaped core tube 13a and the attachment 13b that is attached to the outside surface of the core tube 13a. The attachment 13b in a spindle shape is formed with the trocar connection portion 13x in a truncated conical shape that becomes thinner in the direction to approach the trocar 31 and the root portion 13z in a truncated conical shape that becomes thinner in the direction to approach the camera unit 11. An annular projection 13j around the whole outer circumference is formed on the outside surface of the core tube 13a, and a lower edge of the attachment 13b fitted on the outside of the core tube 13a is supported by the annular projection 13j and fixed by an adhesive in this state.

Here, as illustrated in (b) to (d) in FIG. 21, a height H8 of the trocar connection portion 13x is set to 10 mm, a height H9 of the root portion 13z is set to 5 mm, an outer diameter (the outer diameter of the attachment 13b) H10 of each of the trocar connection portion 13x and the root portion 13z is set to 8.5 mm, an outer diameter H11 of an upper end of the core tube 13a is set to 2.8 mm, an outer diameter H12 of a lower end of the core tube 13a is set to 3.5 mm, and an outer diameter H13 of a portion of the core tube 13a in which the annular projection 13j is formed is set to 4.5 mm.

Figure 22:
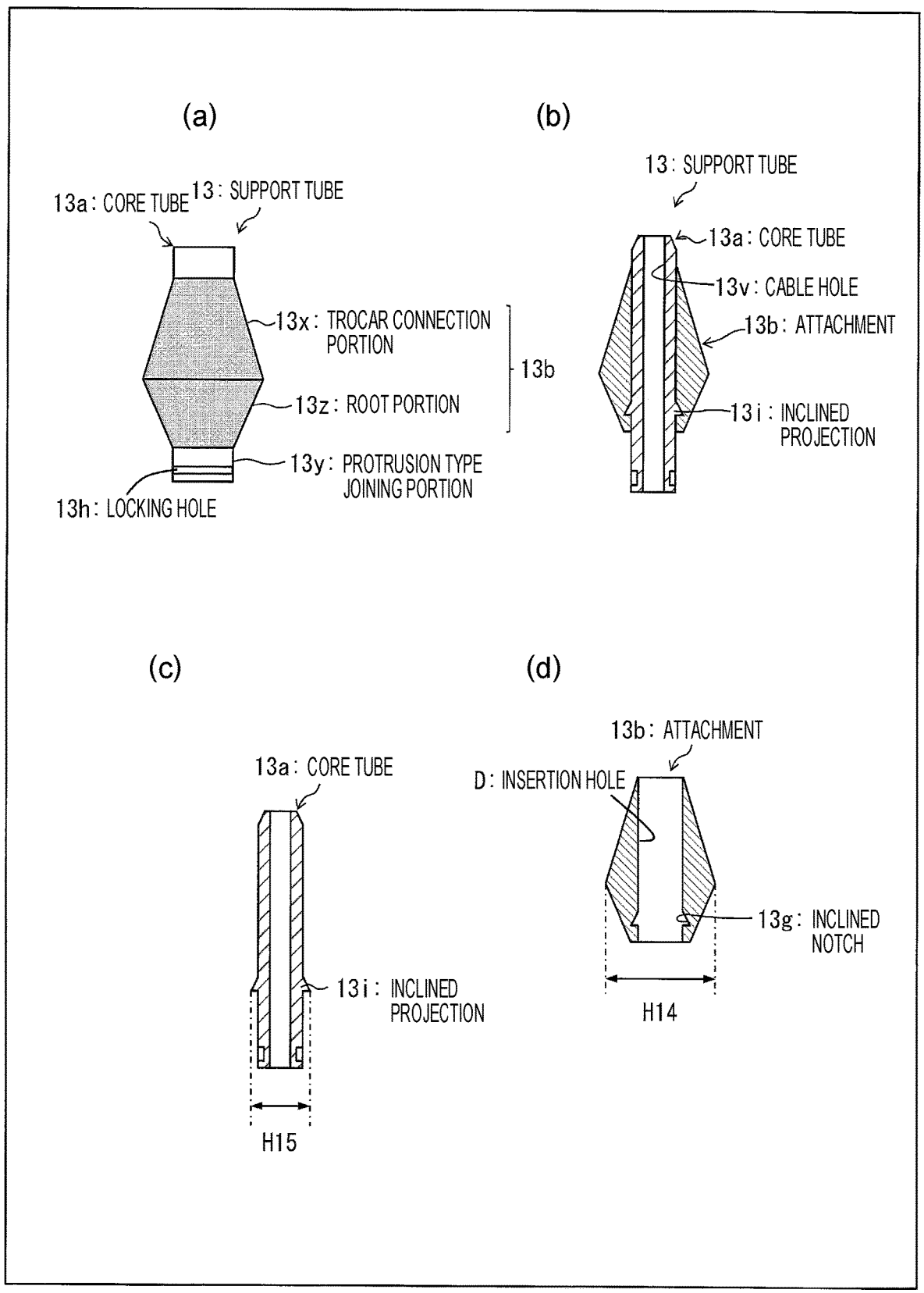
FIG. 22 is a front diagram (a) and cross-sectional diagrams (b) to (d) that illustrate another specific example of the support tube of FIG. 18.

FIG. 22 is a front diagram (a) and cross-sectional diagrams (b) to (d) that illustrate another specific example of the support tube of FIG. 18. In the configuration in FIG. 22, two inclined projections 13i (projections which have inclined surfaces and thereby have bumps which become larger in the downward direction of the core tube 13a) that are opposed to each other are provided on the outside surface of the core tube 13a, two inclined notches 13g (notches which have inclined surfaces and thereby have recesses which become larger in the downward direction of the core tube 13a) that are opposed to each other are formed in the vicinity of the lower edge of the attachment 13b, the attachment 13b is fitted on the outside of the core tube 13a from up to down, and the inclined notches 13g are thereby locked in the inclined projections 13i. Note that fixing by an adhesive may be performed in this locked state.

In the support tube 13 in FIG. 22, an outer diameter (the outer diameter of the attachment 13b) H14 of each of the trocar connection portion 13x and the root portion 13z is set to 8.5 mm, and an outer diameter H15 of a portion in which the inclined projections 13i of the core tube 13a are formed is set to 4.0 to 4.5 mm.

Figure 23:
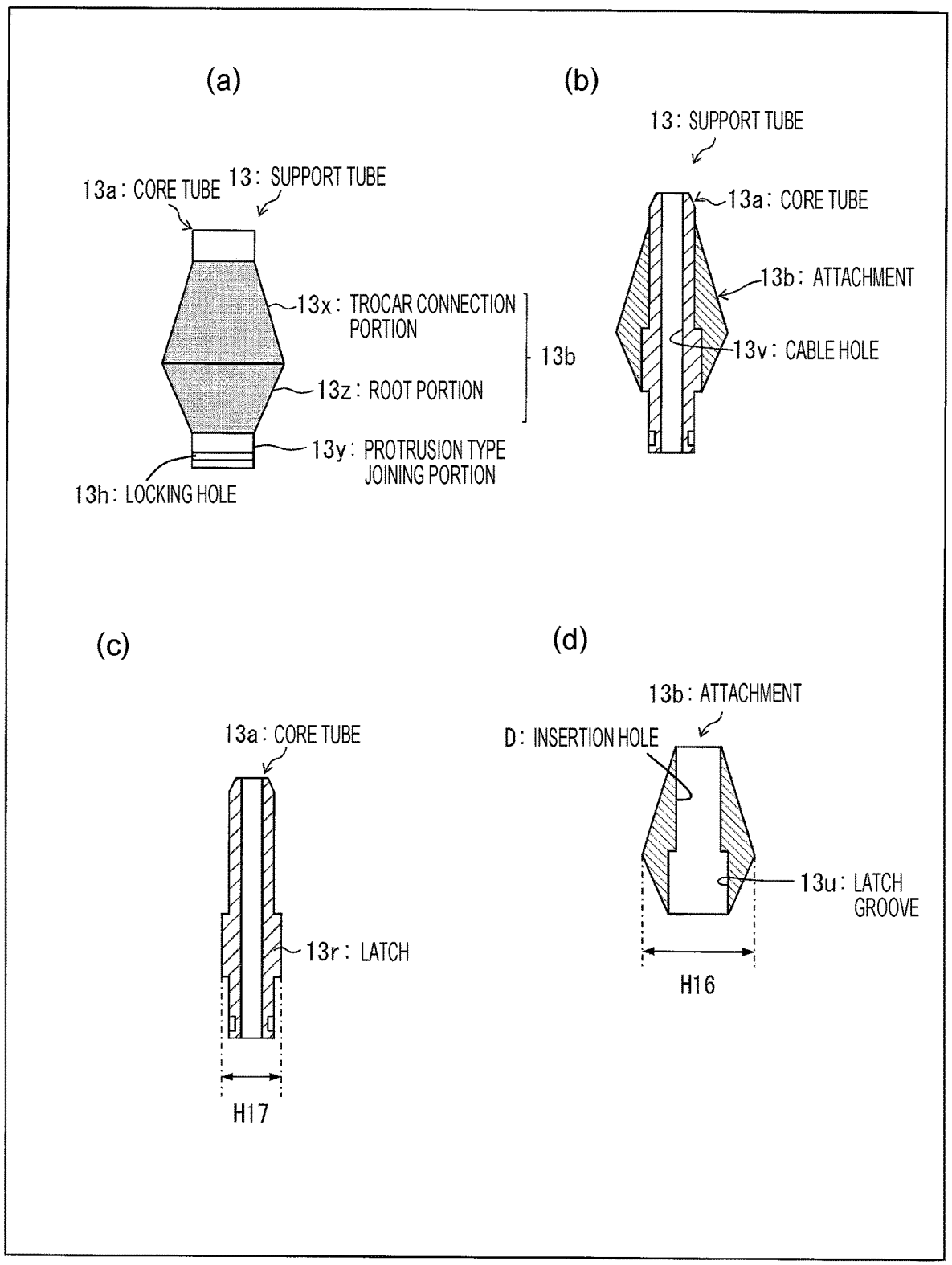
FIG. 23 is a front diagram (a) and cross-sectional diagrams (b) to (d) that illustrate still another specific example of the support tube of FIG. 18.

FIG. 23 is a front diagram (a) and cross-sectional diagrams (b) to (d) that illustrate still another specific example of the support tube of FIG. 18. In the configuration in FIG. 23, two (protruded) latches 13r that are opposed to each other are formed on the outside surface of the core tube 13a, two latch grooves 13u that are opposed to each other are formed in the vicinity of the lower edge of the attachment 13b, the attachment 13b is fitted on the outside of the core tube 13a from up to down, and the latches 13r are thereby locked in the latch grooves 13u and fixed by an adhesive in this locked state.

In the support tube 13 in FIG. 23, an outer diameter (the outer diameter of the attachment 13b) H16 of each of the trocar connection portion 13x and the root portion 13z is set to 8.5 mm, and an outer diameter H17 of a portion in which the latches 13r of the core tube 13a are formed is set to 4.5 mm.

In the support tube 13 in FIG. 23, the above latch structure is provided, and the durability against the stress in a case where the camera unit is fixed is thereby enhanced.

In the third embodiment, a material with high thermal conductivity (for example, metal) is used for the core tube 13a that is the inside part of the support tube 13, an insulating material (for example, resin) is used for the attachment 13b that is the outside part, the heat dissipation of the camera unit 11 may thereby be enhanced, the attachment 13b that possibly touches the body may thereby be insulated, and safety may be enhanced.

Further, a slit is provided to the attachment 13b, the gas that pressurizes the inside of the body cavity is released from the slit, and an improvement in the heat dissipation by air flow may thereby be intended. Note that the slit provided to the attachment 13b may be a full slit that longitudinally crosses the attachment 13b from one opening to the other opening of the attachment 13b or may be a partial slit that does not reach the other opening.

Fourth Embodiment

Figure 24:
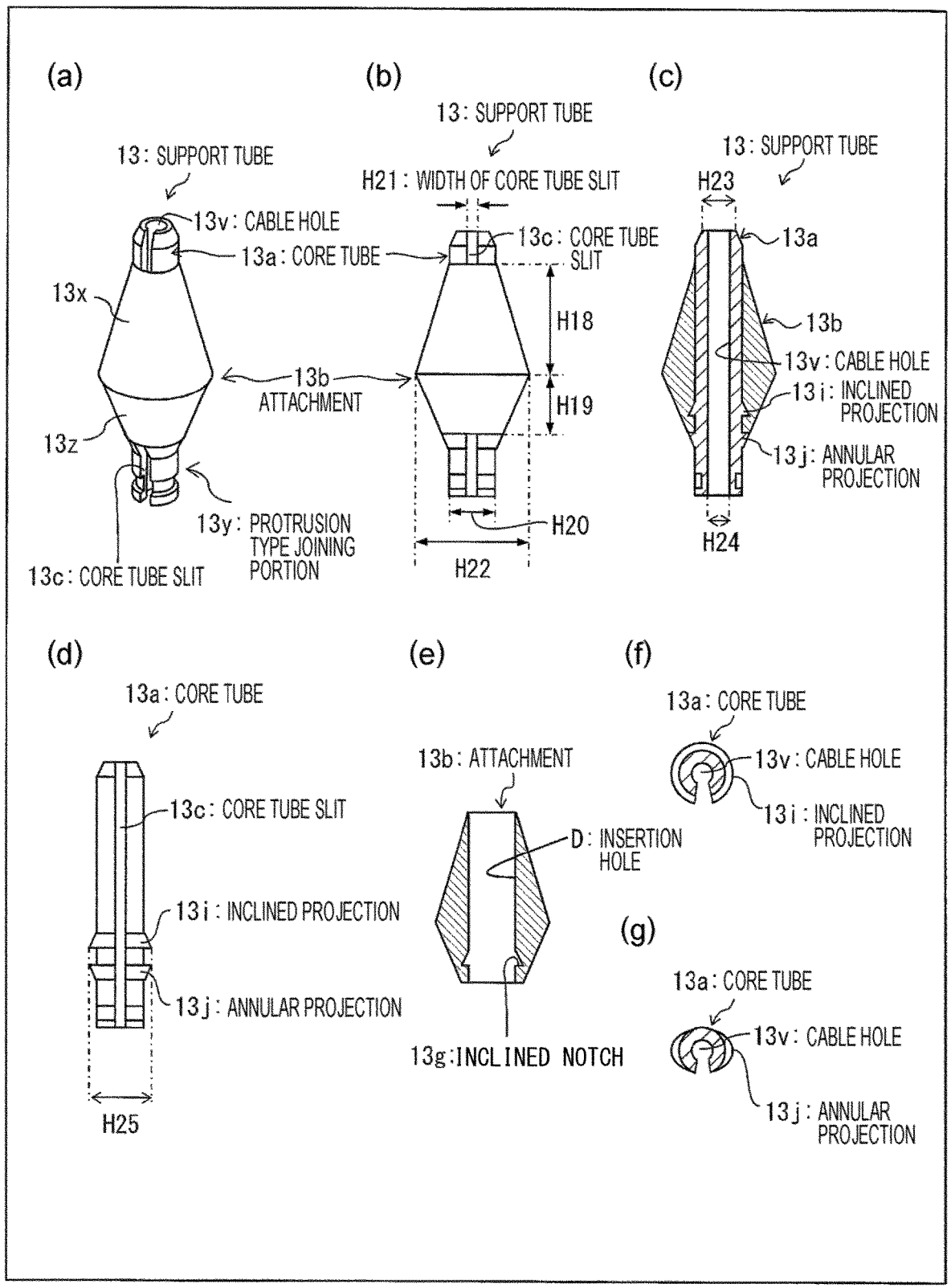
FIG. 24 is a perspective diagram (a), front diagrams (b) and (d), and cross-sectional diagrams (c), (e), (f), and (g) that illustrate a configuration of the support tube in a fourth embodiment.

FIG. 24 is a perspective diagram (a), front diagrams (b) and (d), and cross-sectional diagrams (c), (e), (f), and (g) that illustrate a configuration of the support tube in a fourth embodiment. As illustrated in (a) in FIG. 24, the support tube 13 is configured with the core tube 13a that has the cable hole 13v (circular opening) and the attachment 13b that is attached to the outside surface of the core tube 13a. A core tube slit 13c that longitudinally crosses the core tube 13a from one opening to the other opening of the core tube 13a is formed in the core tube 13a. The hole diameter (the inner diameter of the support tube 13) of the cable hole 13v is smaller than the outer diameter of the camera-side cable connector.

As illustrated in (a) and (b) in FIG. 24, the attachment 13b is in a spindle shape that has the insertion hole D (circular opening) and is formed with the trocar connection portion 13x in a truncated conical shape that becomes thinner in the direction to approach the trocar 31 and the root portion 13z in a truncated conical shape that becomes thinner in the direction to approach the camera unit 11. Further, the support tube 13 is configured by fitting the core tube 13a in the insertion hole D of the attachment 13b and thereby mounting the attachment 13b on the core tube 13a. Here, the attachment 13b is configured such that the camera-side cable connector 15a may be placed through the inside of the insertion hole D.

Note that in the core tube 13a, the lower portion (an end portion on the camera unit 11 side) on which the attachment 13b is not mounted serves as the protrusion type joining portion 13y.

As illustrated in (c) to (g) in FIG. 24, the two inclined projection 13i that are opposed to each other are formed on the outside surface of the core tube 13a, and the annular projection 13j around the whole outer circumference is formed on a lower side (camera unit side) of the inclined projections 13i. Further, the two inclined notches 13g that are opposed to each other are formed in the vicinity of the lower edge of the attachment 13b. Further, the attachment 13b is fitted on the outside of the core tube 13a from up to down, the inclined notches 13g are thereby locked in the inclined projections 13i, and the lower edge of the attachment 13b is supported by the annular projection 13j. Note that fixing by an adhesive may be performed in this state. Note that the inclined projection 13i on the upper side is made smaller than the annular projection 13j on the lower side, two inclined projections 13i on the upper side are provided as illustrated in (g) in FIG. 24, and the attachment 13b thereby warps and facilitates fitting. Further, the annular projection 13j is provided on the lower side, and the durability against the downward stress may thereby be enhanced.

Further, in order to avoid the possibility that the fitting between the core tube 13a and the attachment 13b is accidentally removed and falls to the inside of the body, a structure may be made in which the inclined projection 13i or the annular projection 13j may not be removed after the inclined projection 13i or the annular projection 13j is once fitted. In such a case, it is desirable that the core tube 13a and the attachment 13b of the support tube 13 are not fitted together in the reverse direction in order to prevent the connection in the reverse direction. For example, as the inclined projection 13*i* and the inclined notch 13*g* that are illustrated in (d) and (e) in FIG. 24, a shape that is asymmetric with respect to the up-down direction is formed, and the fitting in the reverse direction may thereby be prevented. This is particularly important because mistakes in manufacturing steps may not easily be fixed.

The core tube slit 13*c* is used in a case where the camera-side cable is placed through the core tube 13*a* from a side surface. Thus, as illustrated in (f) and (g) in FIG. 24, it is desirable that the slit width is configured to become smaller from an outside surface toward an inside surface and that it is difficult for the camera-side cable that is once placed through the core tube slit 13*c* to be removed.

Here, as illustrated in (b) in FIG. 24, a height H18 of the trocar connection portion 13*x* is set to 10 mm, a height H19 of the root portion 13*z* is set to 5 mm, an outer diameter H20 of the lower end of the core tube 13*a* is set to 3.5 mm, a width H21 of the core tube slit 13*c* is set to 1.2 mm, an outer diameter (the outer diameter of the attachment 13*b*) H22 of each of the trocar connection portion 13*x* and the root portion 13*z* is set to 8.5 mm, an outer diameter H23 of the upper end of the core tube 13*a* is set to 2.8 mm, an inner diameter H24 of the core tube 13*a* is set to 1.6 mm, and an outer diameter H25 of a portion of the core tube 13*a* in which the inclined projection 13*i* is formed is set to 4.5 mm.

Figure 25:
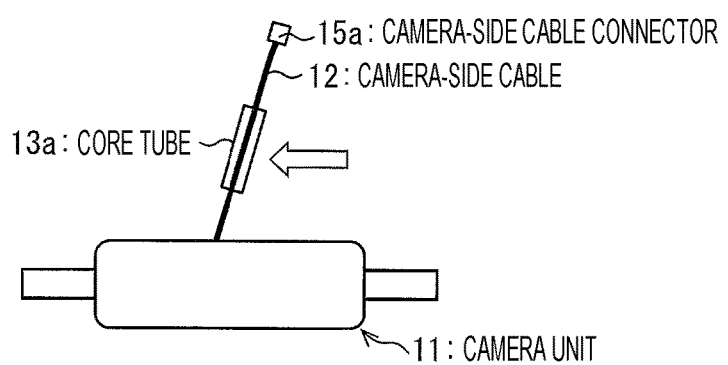
FIG. 25 is cross-sectional diagrams (a) and (b) that illustrate a method for placing the support tube of the fourth embodiment around the camera-side cable.
Figure 25:
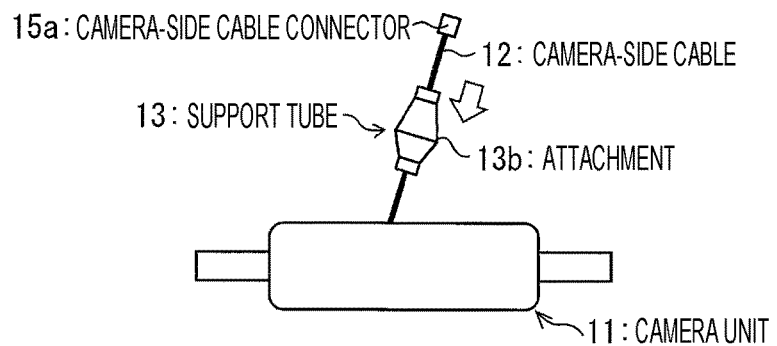

FIG. 25 is cross-sectional diagrams (a) and (b) that illustrate a method for placing the support tube of the fourth embodiment around the camera-side cable. In a case where the support tube 13 of FIG. 24 is used, the camera-side cable 12 is placed through an internal portion of the core tube 13*a* from the core tube slit 13*c* (from the side surface of the core tube 13*a*) as illustrated in (a) in FIG. 25, the attachment 13*b* is next placed around the camera-side cable 12 from the side of the camera-side cable connector 15*a* as illustrated in (b) in FIG. 25, and the attachment 13*b* may thereby be fitted on the outside of the core tube 13*a*.

Fifth Embodiment

Figure 26:
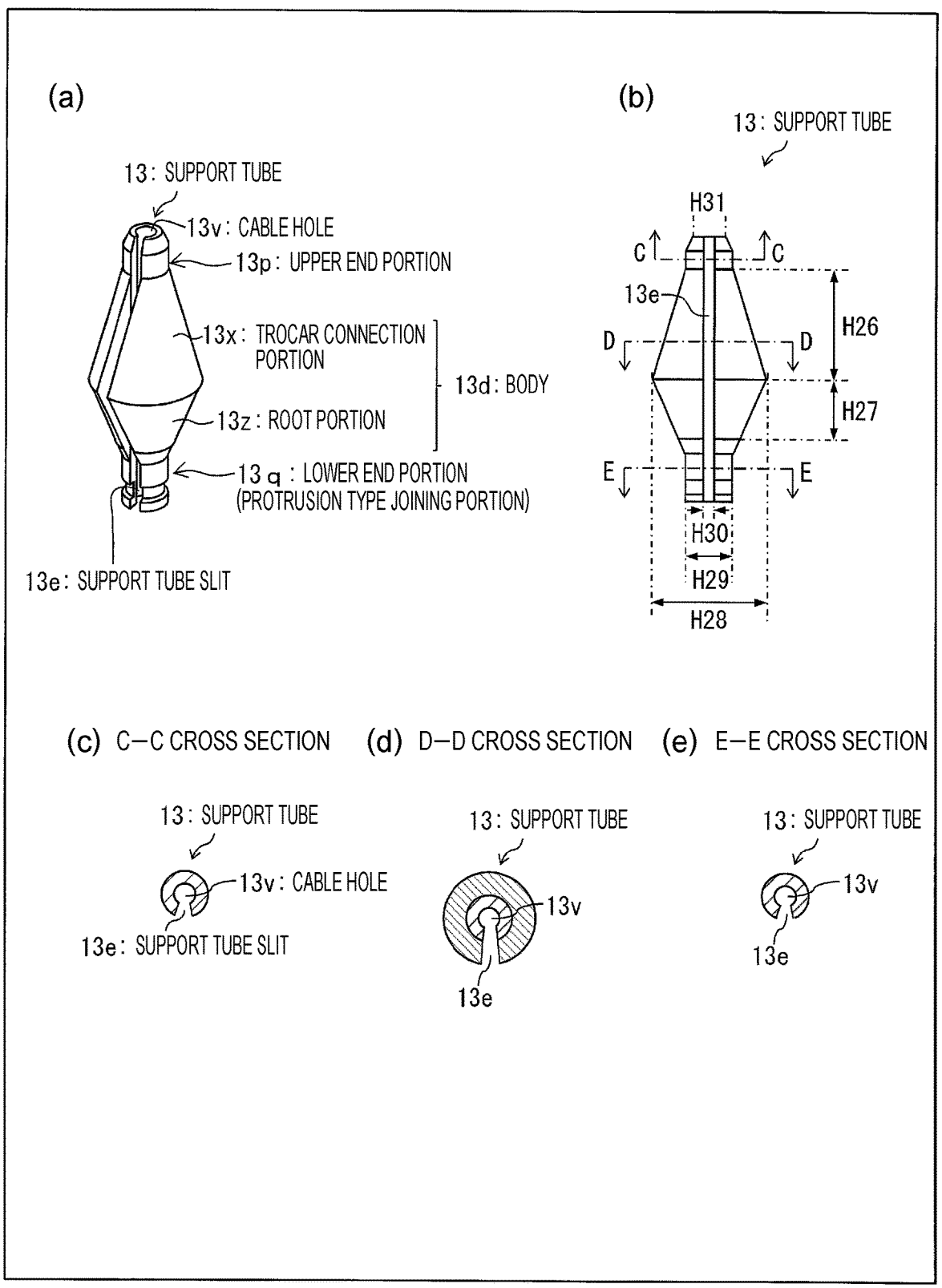
FIG. 26 is a perspective diagram (a), a front diagram (b), and cross-sectional diagrams (c) to (e) that illustrate a configuration of the support tube in a fifth embodiment.

FIG. 26 is a perspective diagram (a), a front diagram (b), and cross-sectional diagrams (c) to (e) that illustrate a configuration of the support tube in a fifth embodiment. As illustrated in (a) to (e) in FIG. 26, the support tube 13 is configured with a pipe-shaped upper end portion 13*p* that has the cable hole 13*v* (circular opening), a pipe-shaped lower end portion 13*q* that has the cable hole 13*v*, and a body portion 13*d* that is integrally formed with the upper end portion 13*p* and the lower end portion 13*q*. Further, the lower end portion 13*q* functions as the protrusion type joining portion. The hole diameter (the inner diameter of the support tube 13) of the cable hole 13*v* is smaller than the outer diameter of the camera-side cable connector.

As illustrated in (a) and (b) in FIG. 26, the body portion 13*d* is in a spindle shape that has the cable hole 13*v* and is formed with the trocar connection portion 13*x* in a truncated conical shape that becomes thinner in the direction to approach the trocar and the root portion 13*z* in a truncated conical shape that becomes thinner in the direction to approach the camera unit.

Here, a support tube slit 13*e* that longitudinally crosses the support tube 13 from an opening on the upper end portion 13*p* side to an opening on the lower end portion 13*q* side is formed in the outside surface of the support tube 13. The support tube slit 13*e* is used in a case where the camera-side cable is placed through the internal portion of the support tube 13 from a side surface. Thus, as illustrated in (c) to (e) in FIG. 26, it is desirable that the slit width is configured to become smaller from the outside surface toward the inside surface and that it is difficult for the camera-side cable that is once placed through the support tube slit 13*e* to be removed.

Here, as illustrated in (b) in FIG. 26, a height H26 of the trocar connection portion 13*x* is set to 10 mm, a height H27 of the root portion 13*z* is set to 5 mm, an outer diameter (the outer diameter of the body portion 13*d*) H28 of each of the trocar connection portion 13*x* and the root portion 13*z* is set to 8.5 mm, an outer diameter H29 of the lower end portion 13*q* is set to 3.5 mm, a width H30 of the support tube slit 13*e* is 1.2 mm, and an outer diameter H31 of the upper end portion 13*p* is set to 2.8 mm.

Figure 27:
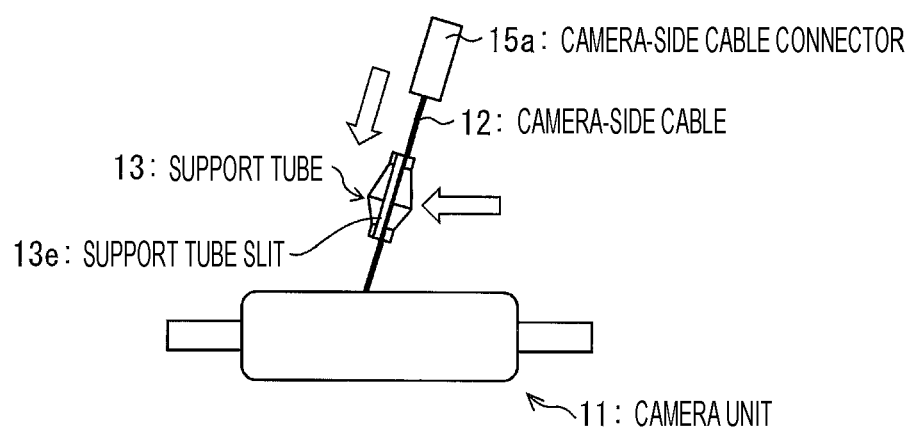
FIG. 27 is a cross-sectional diagram that illustrates a method for placing the support tube of the fifth embodiment around the camera-side cable.

FIG. 27 is a cross-sectional diagram that illustrates a method for placing the support tube of the fifth embodiment around the camera-side cable. In a case where the support tube 13 of FIG. 26 is used, after the camera-side cable connector 15*a* is provided as illustrated in FIG. 27, the camera-side cable 12 may be placed through the internal portion of the support tube 13 from the support tube slit 13*e* (from the side surface of the support tube 13).

Figure 28:
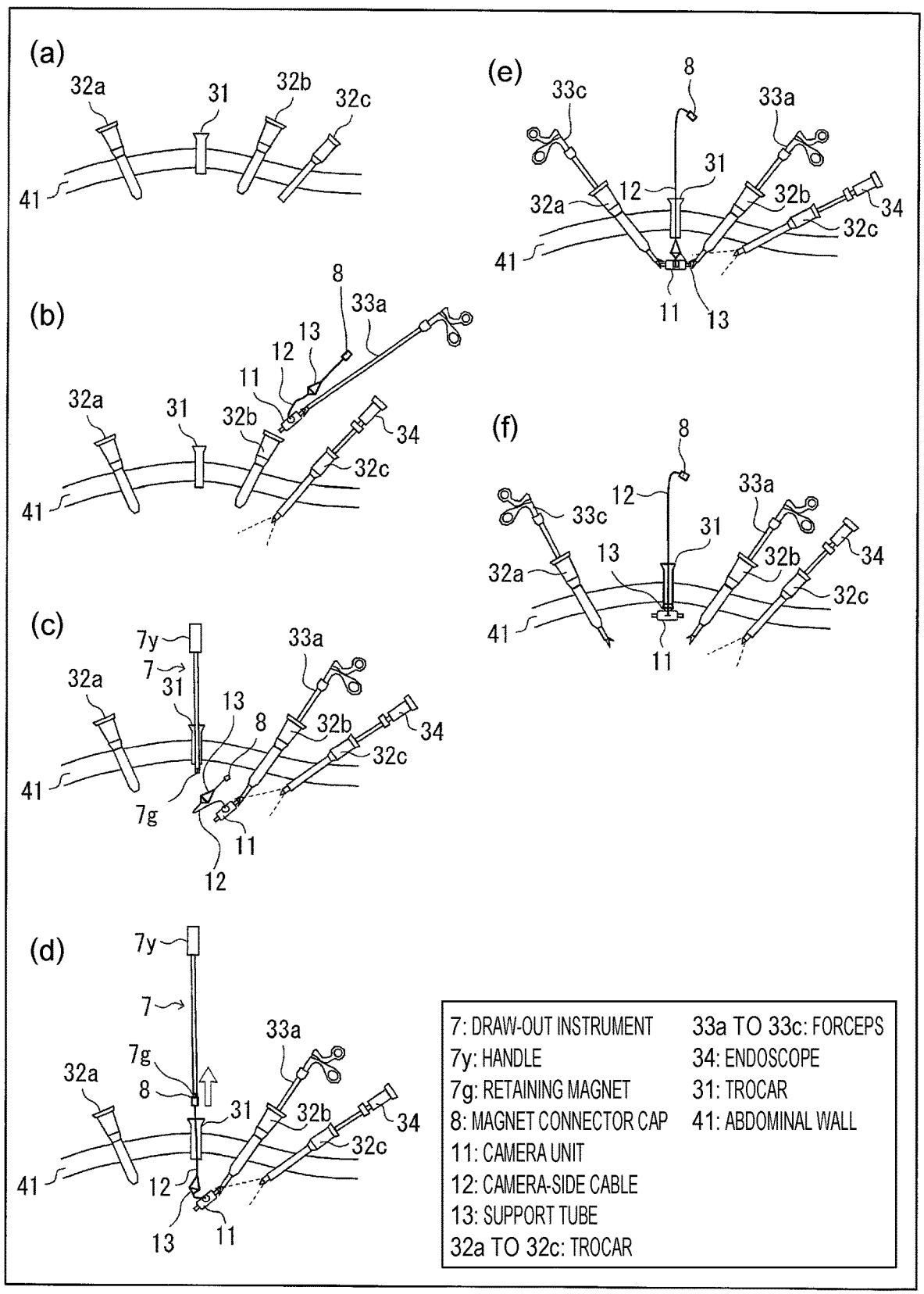
FIG. 28 is schematic diagrams (a) to (f) that illustrate use examples of the support tube, the camera unit, and the trocars in a sixth embodiment.

Sixth Embodiment (a) to (f) in FIG. 28 are schematic diagrams that illustrate an installation method of the camera unit in the body in a sixth embodiment. In the sixth embodiment, the camera-side cable connector 15*a* in FIG. 1 or the like is covered by a magnet connector cap 8, and a draw-out instrument 7 that has a handle 7*y* at one end and has a retaining magnet 7*g* on the other end is used. Note that instead of the magnet connector cap 8, a magnetic body connector cap (a protection cap provided with a magnetic body at a tip end) may be used. As the magnetic body of the magnetic body connector cap, a magnetic body that is not a magnet is used. This prevents the magnetic body connector cap from being unintentionally stuck to another metal treatment instrument, and the work efficiency may thereby be enhanced.

As illustrated in (a) in FIG. 28, the operator first opens holes (ports) for inserting forceps and an endoscope in the body cavity in the abdominal wall 41 and inserts the trocars 32*a* to 32*c* in the ports. In addition, in order to install the camera unit 11 in the body cavity, the port is opened in a position in the abdominal wall 41 from which the whole organ including an affected site may be seen, and the trocar 31 is inserted therein.

Next, as illustrated in (b) in FIG. 28, the operator inserts the endoscope 34 in the body cavity through the trocar 32*c* and inserts the camera unit 11 grasped by the forceps 33*a*, the camera-side cable 12 that includes the connector covered by the magnet connector cap 8, and the support tube 13 placed around the camera-side cable 12 in the body cavity through the trocar 32*b* while observing the inside of the body by using the endoscope 34.

Next, as illustrated in (c) in FIG. 28, the operator moves the camera unit 11 to the vicinity of the trocar 31 by operating the forceps 33*a* and inserts the draw-out instrument 7 in the body cavity through the trocar 31.

Next, as illustrated in (d) in FIG. 28, the draw-out instrument 7 is pulled out from the trocar 31 in a state where the magnet connector cap 8 is adhered to the retaining magnet 7*g* provided to a tip end of the draw-out instrument 7, and the camera-side cable connector that is covered by the magnet connector cap 8 is thereby guided to the outside of the body. Here, the camera unit 11 (the grip portion thereof) is grasped by the forceps 33*a*.

Next, as illustrated in (e) in FIG. 28, the operator draws up the camera-side cable 12 guided to the outside of the body by forceps, the hand, or the like and thereby brings the tip end of the support tube 13 to proximity of the opening of the trocar 31.

Next, as illustrated in (f) in FIG. 28, the operator further draws up the camera-side cable 12 and the camera unit 11, thereby inserts one end (trocar connection portion) of the support tube 13 into the end portion of the trocar 31 on the inside of the body, fits the camera unit 11 in the other end (protrusion type joining portion), thereby connects the one end (trocar connection portion) of the support tube 13 with the end portion of the trocar 31 on the inside of the body, joins the other end (protrusion type joining portion) to the camera unit 11, and thereby fixes the camera-side cable 12 to the abdominal wall 41 or the like such that the tension of the camera-side cable 12 is maintained.

Figure 29:
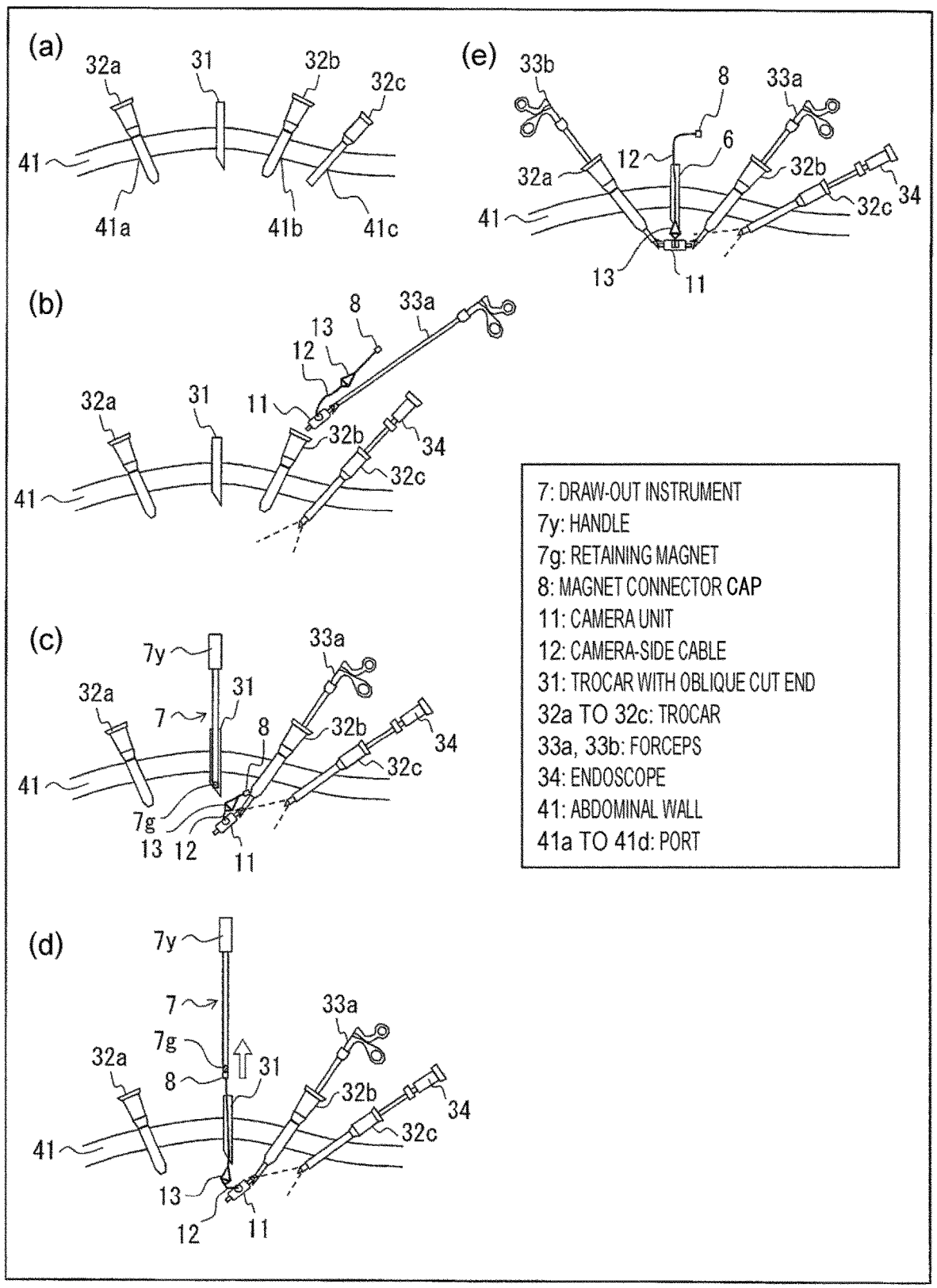
FIG. 29 is cross-sectional diagrams (a) to (e) that illustrate other use examples of the support tube, the camera unit, and the trocars in the sixth embodiment.

(a) in FIG. 29 illustrates a case where the tip end of the trocar 31 is obliquely cut, and similar steps to FIG. 28 may be performed in this case.

Figure 30:
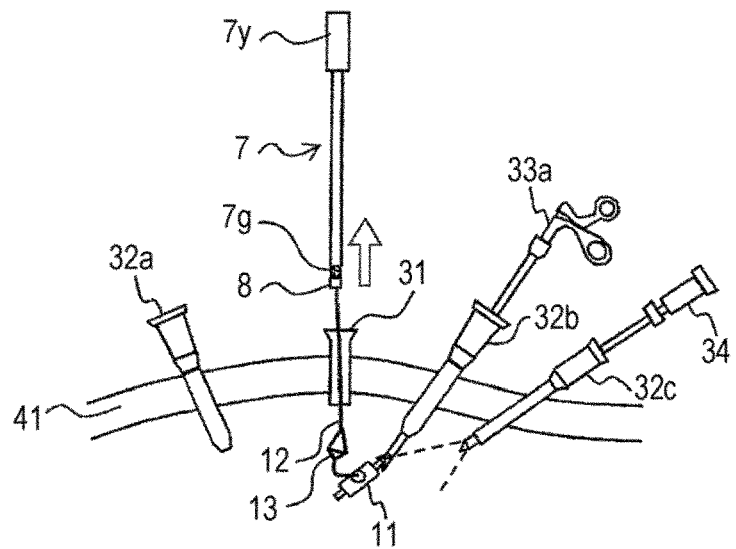
FIG. 30 is cross-sectional diagrams (a) and (b) that illustrate states in installing the camera unit (in drawing up a connector) in the sixth embodiment.
Figure 30:
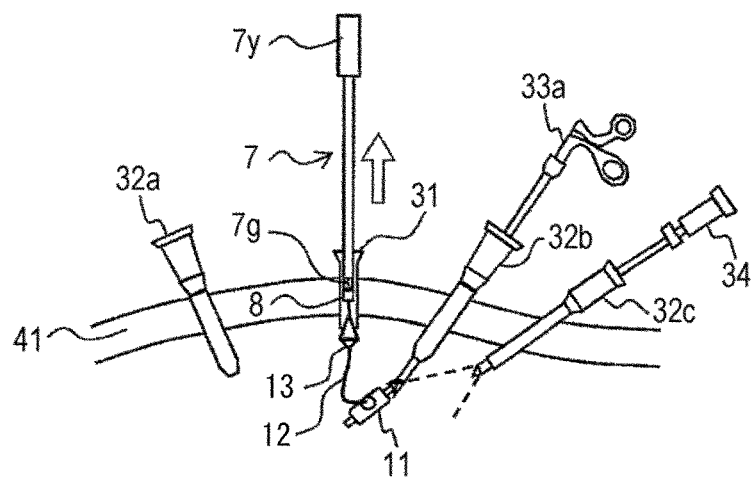

In the modes in FIGS. 28 and 29, in a case where the camera-side cable connector covered by the magnet connector cap 8 is drawn out to the outside of the body by using the draw-out instrument 7, there is not a problem in a case where the support tube 13 is present in the vicinity of the camera unit 11 as in (a) in FIG. 30. However, in a case where the support tube 13 is in the vicinity of the trocar 31 as in (b) in FIG. 30, because the support tube 13 enters the opening of the trocar 31 before the magnet connector cap 8 passes through the inside of the trocar 31 (before the operator pinches the magnet connector cap 8), it is possible that the magnet connector cap 8 is separated from the retaining magnet 7g due to the friction.

Figure 31:
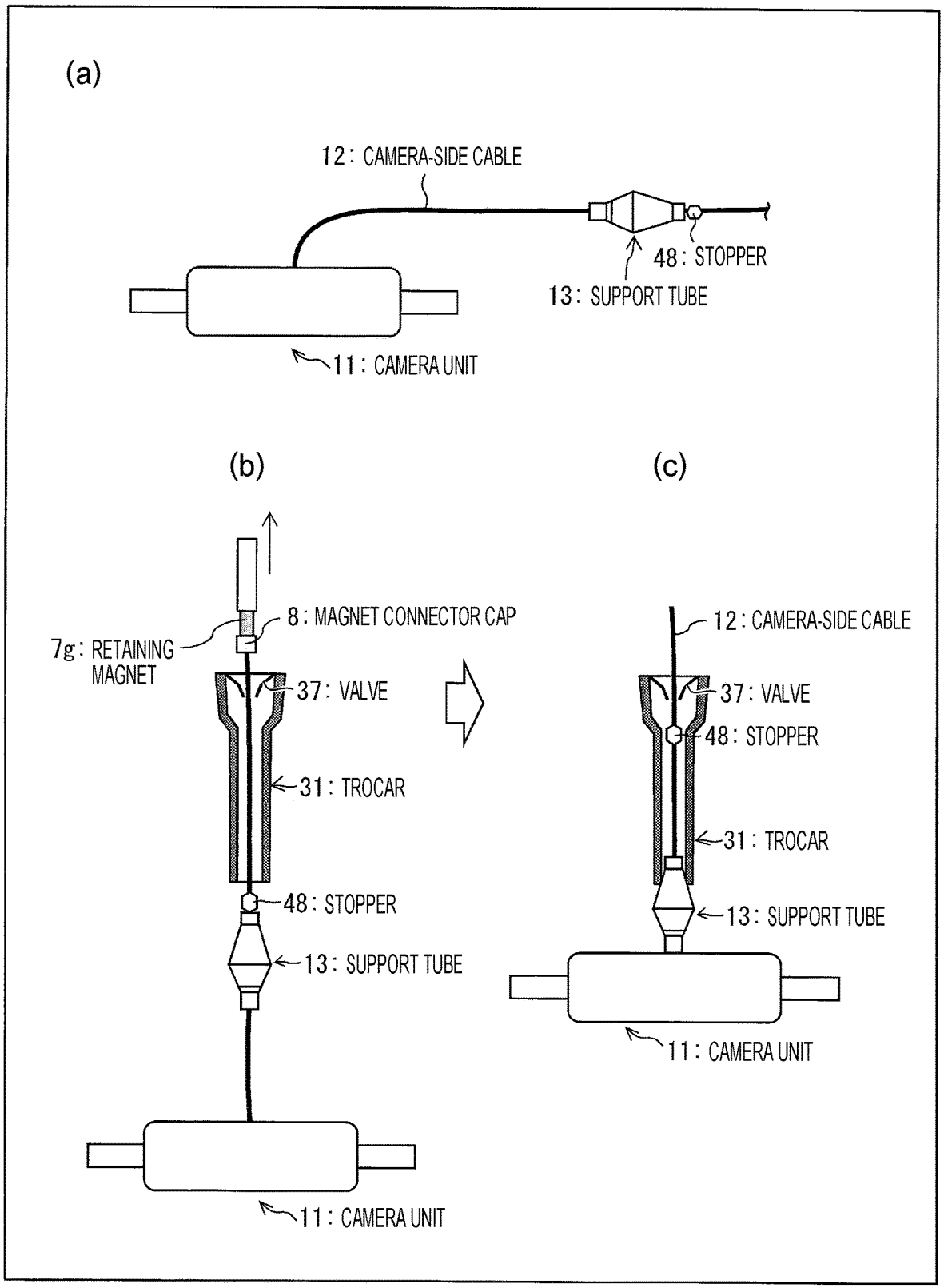
FIG. 31 is schematic diagrams (a) to (c) that illustrate installation examples of the support tube, a stopper, the camera unit, and the trocar in the sixth embodiment.
Figure 32:
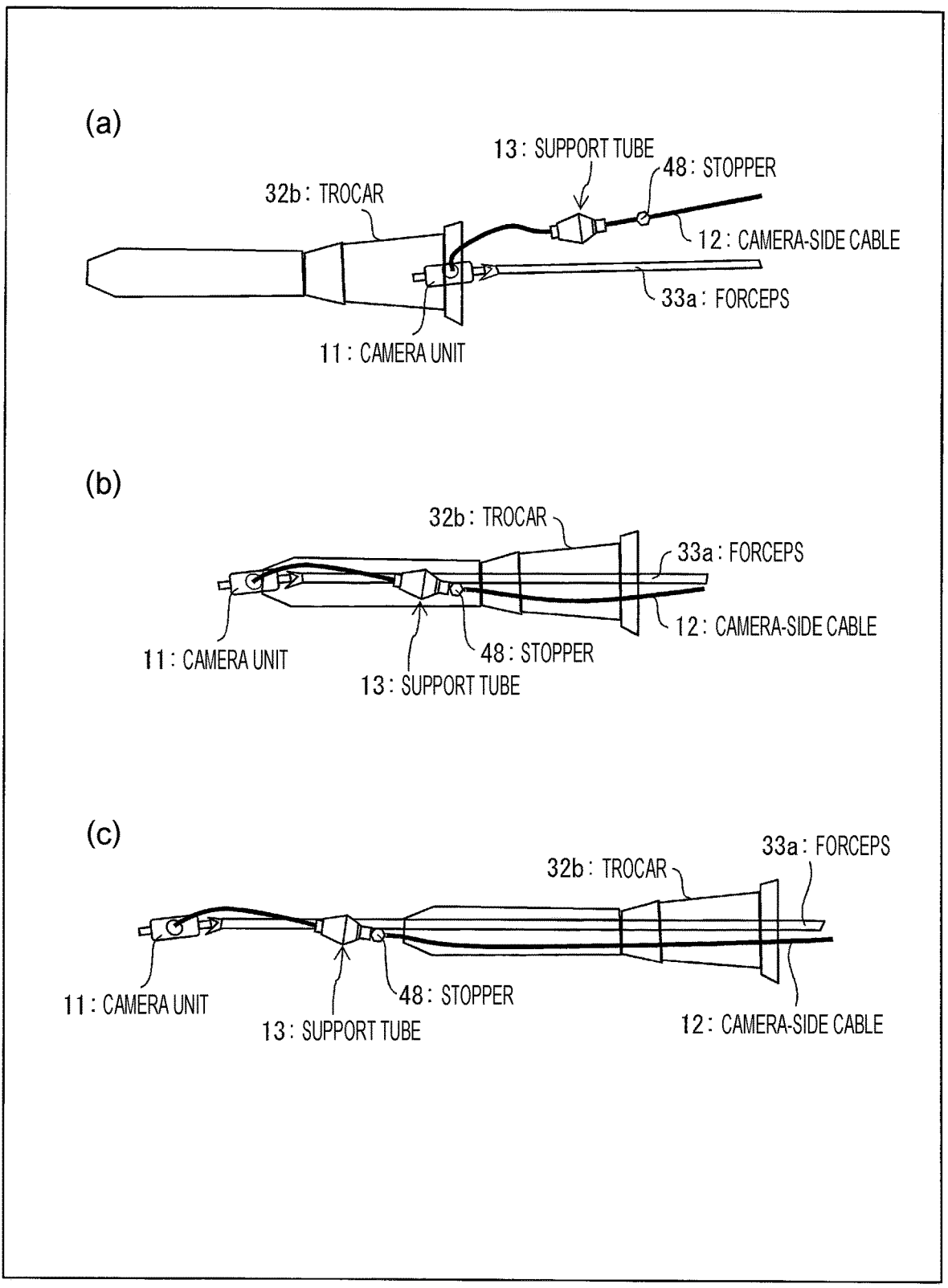
FIG. 32 is schematic diagrams (a) to (c) that illustrate states in installing the camera unit (in introducing the camera unit) in the sixth embodiment.

Thus, as in (a) in FIG. 31, the stopper 48 that stops movement of the support tube 13 toward the connector 15a side is desirably provided between the camera unit 11 and the camera-side cable connector 15a. Accordingly, as in (b) and (c) in FIG. 31, because the support tube 13 enters the opening of the trocar 31 after the magnet connector cap 8 passes through the inside of the trocar 31 (after the operator pinches the magnet connector cap 8), the installation of the camera unit 11 may be performed smoothly.

Here, in a case where the support tube 13 of the second to fourth embodiments is used, the stopper 48 desirably has a shape that may pass through the inside of the insertion hole D of the attachment 13b. For example, the outer diameter of the stopper 48 is set smaller than the minimum hole diameter of the insertion hole D of the attachment 13b. Accordingly, the manufacture of the support tube 13 may be simplified.

Further, as illustrated in (c) in FIG. 31, the stopper 48 is positioned such that the stopper 48 does not reach a valve 37 of the trocar 31 when the installation is completed, and the camera unit 11 may thereby be installed more smoothly.

Note that using the stopper 48 limits the movement range of the support tube 13. However, as illustrated in (a) to (c) in FIG. 32, it has been confirmed that the camera unit 11, the camera-side cable 12, the support tube 13, and the stopper 48 may be introduced to the inside of the body through the trocar 31.

Seventh Embodiment

Figure 33:
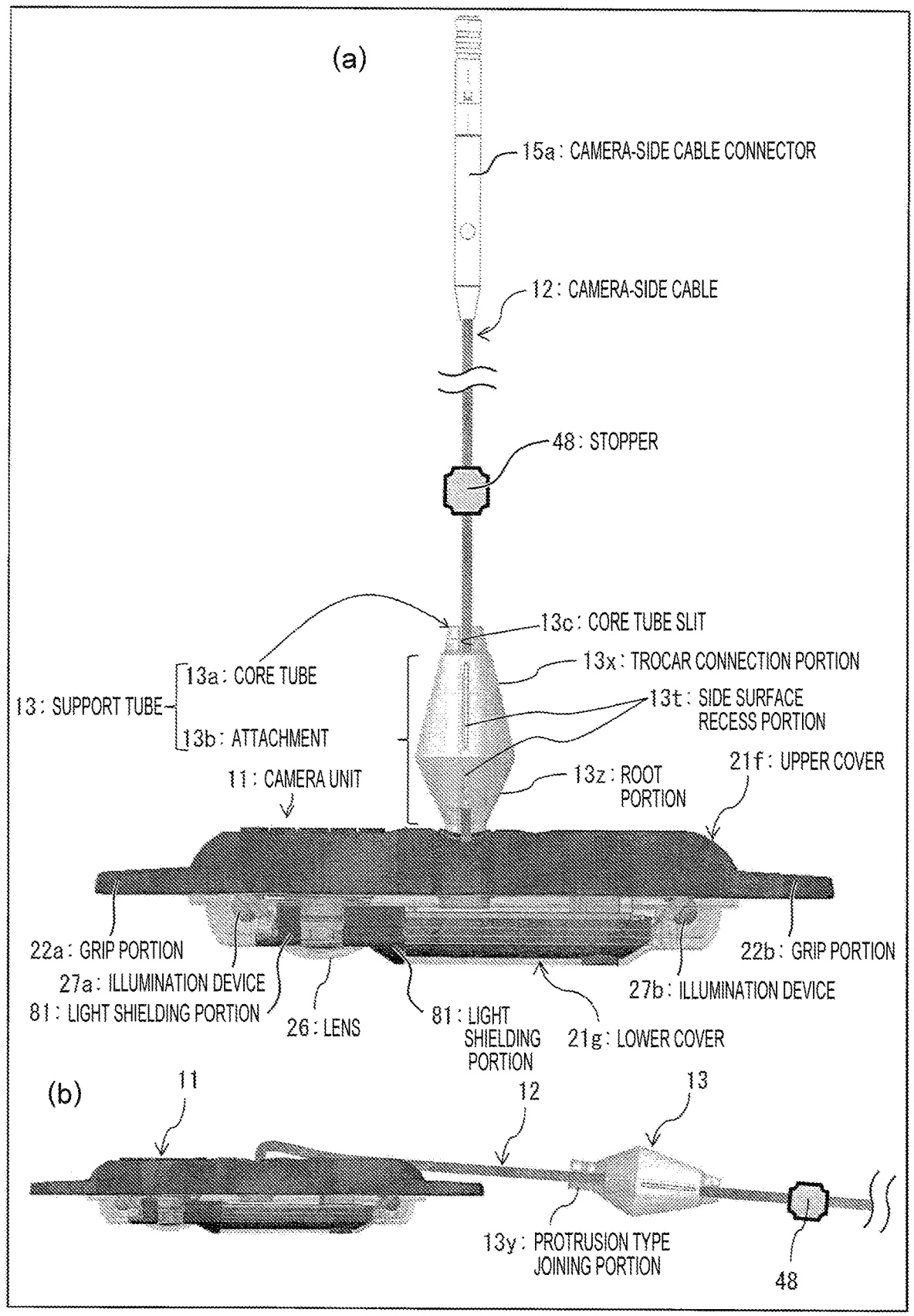
FIG. 33 is front diagrams (a) and (b) that illustrate installation examples of the camera unit, the support tube, the stopper, and the camera-side cable in a seventh embodiment.
Figure 34:
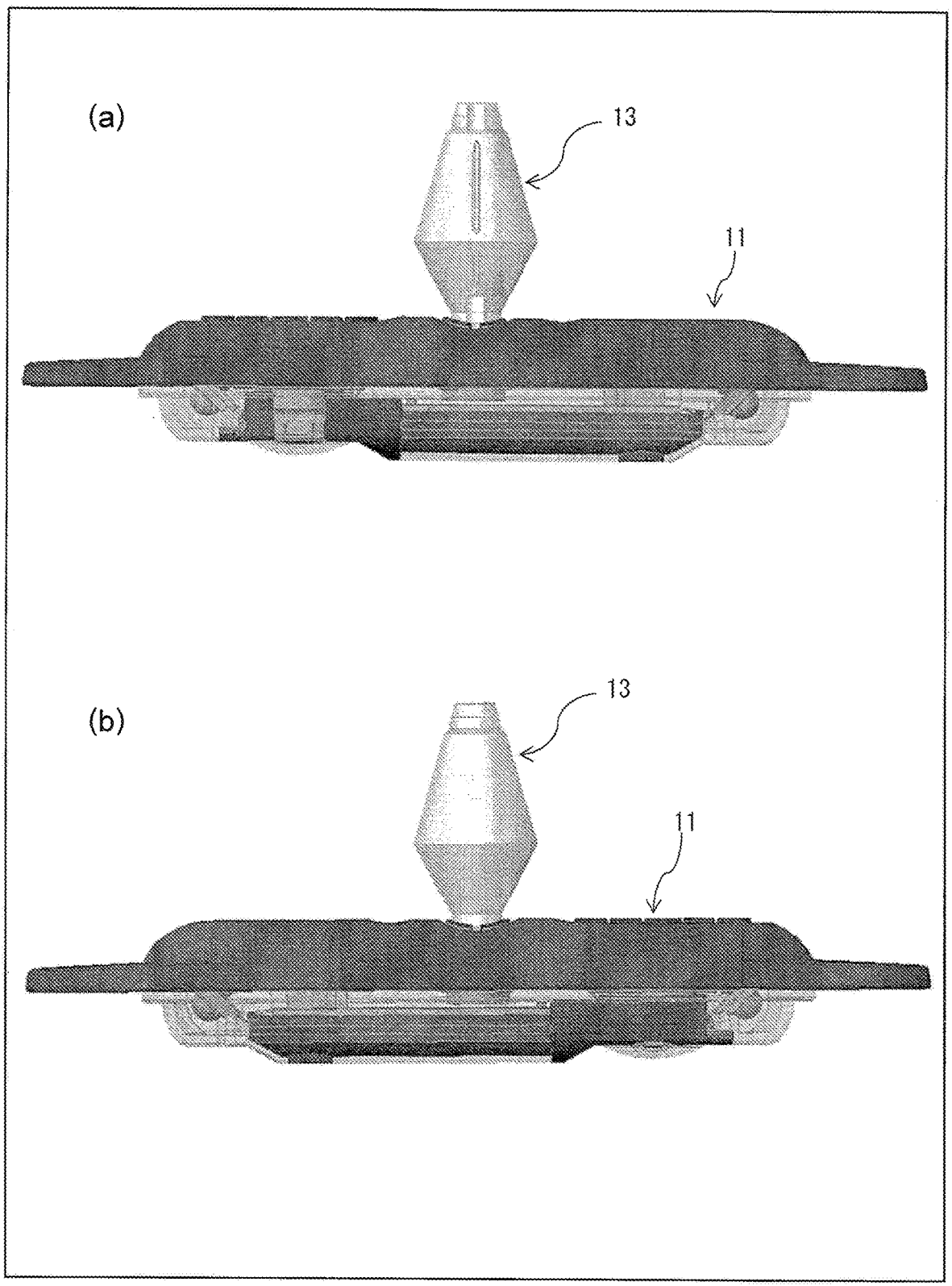
FIG. 34 is a front diagram (a) and a back diagram (b) that illustrate installation examples of the camera unit and the support tube in the seventh embodiment.
Figure 35:
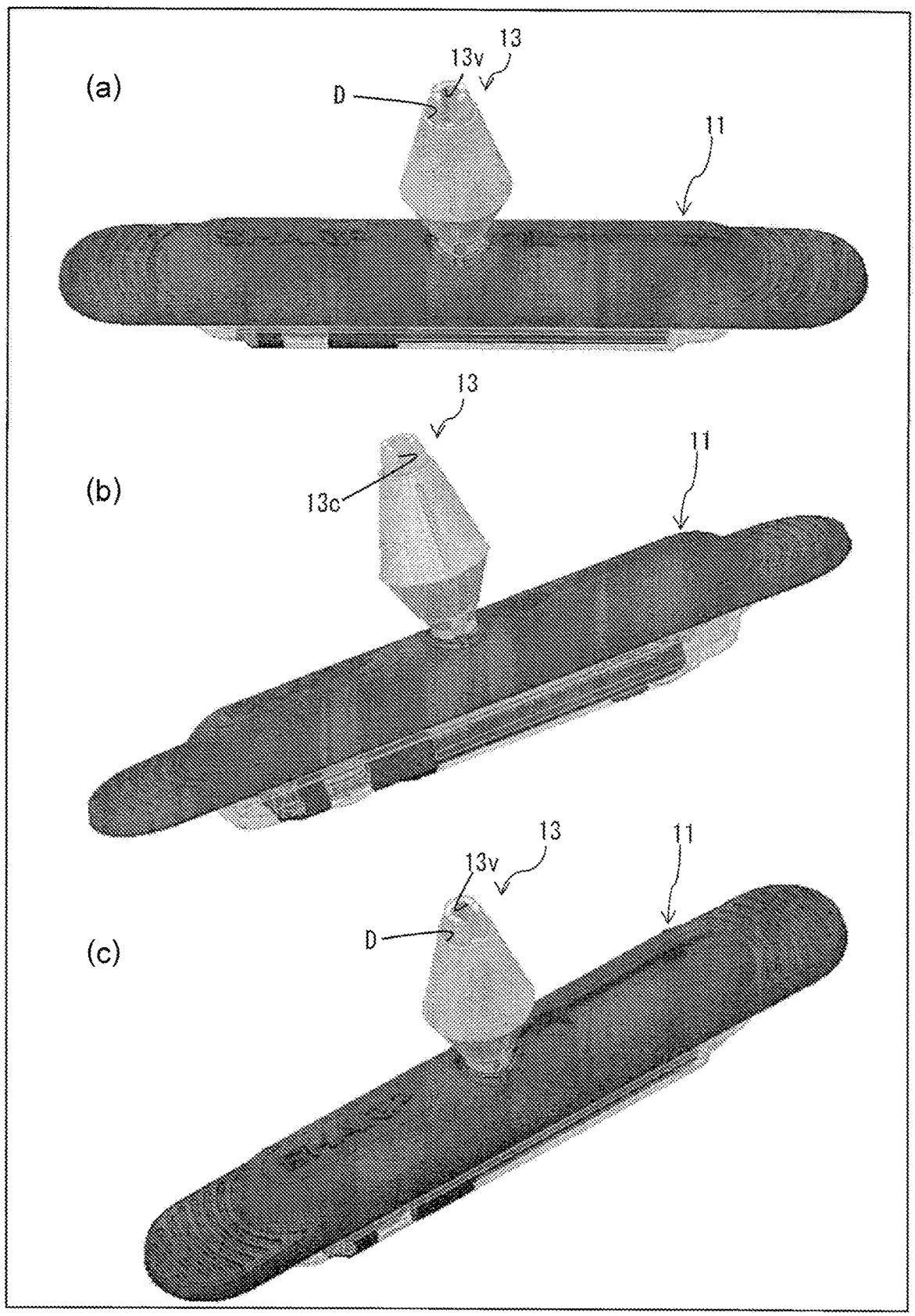
FIG. 35 is perspective diagrams (a) to (c), as seen from an upper side, which illustrate installation examples of the camera unit and the support tube in the seventh embodiment.
Figure 36:
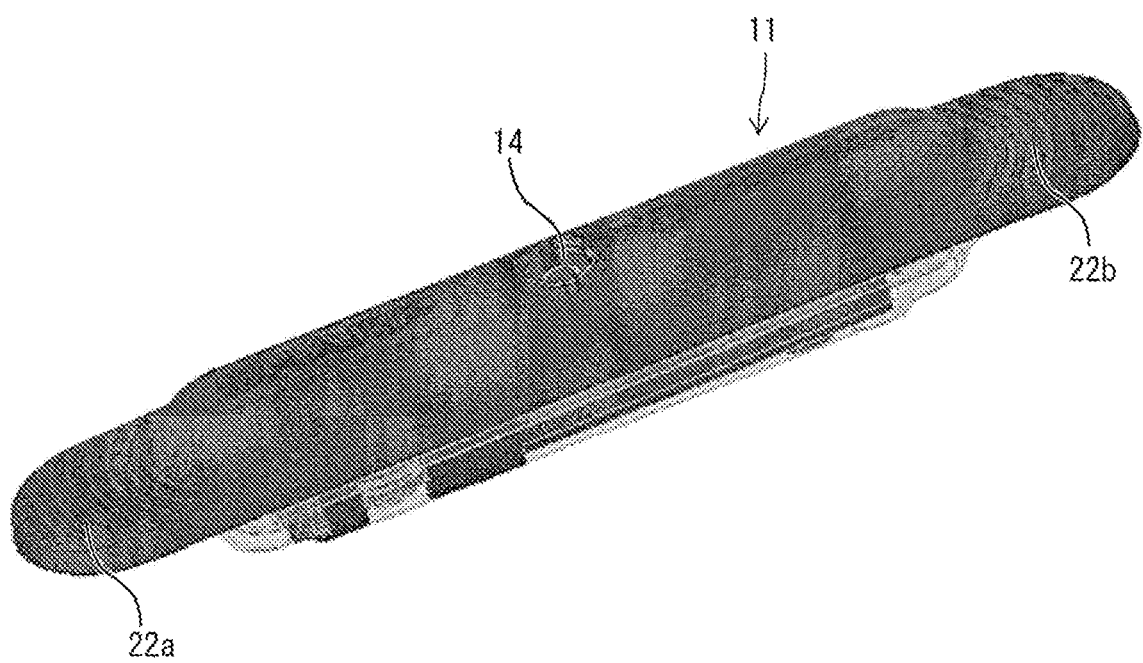
FIG. 36 is a perspective diagram of the camera unit in the seventh embodiment as seen from an upper side.
Figure 37:
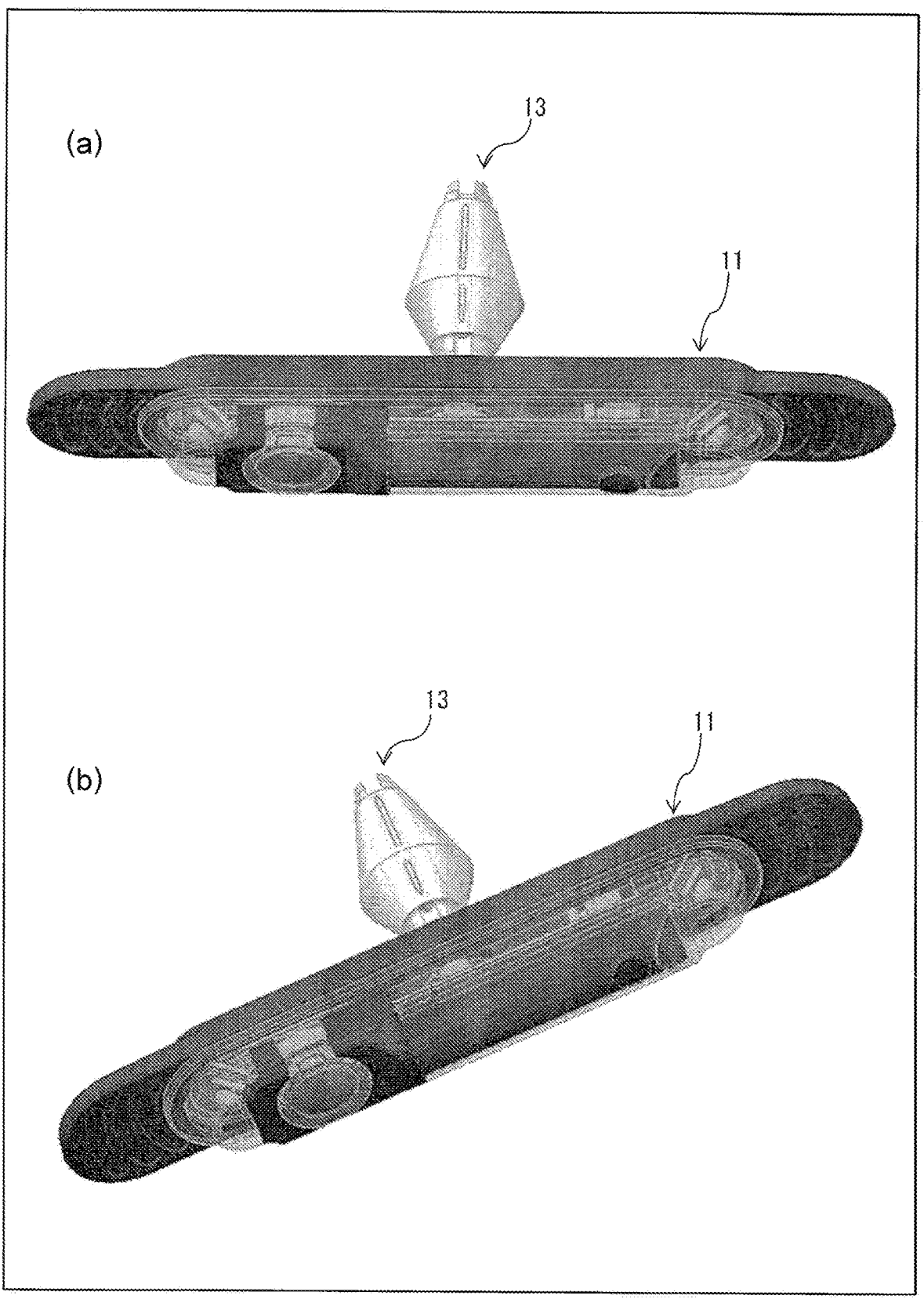
FIG. 37 is perspective diagrams (a) and (b), as seen from a lower side, which illustrate installation examples of the camera unit and the support tube in the seventh embodiment.
Figure 38:
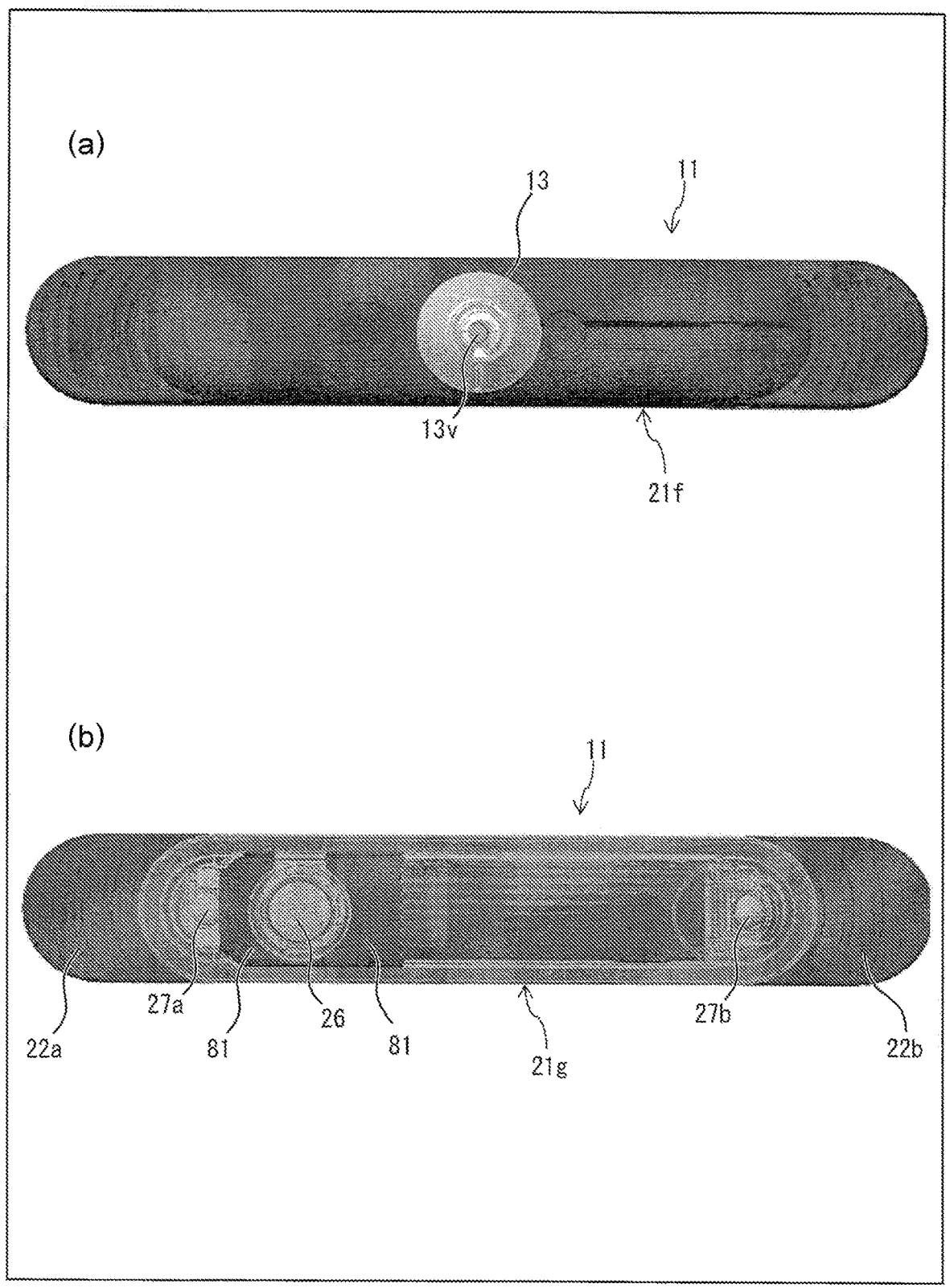
FIG. 38 is a plan diagram (a) and a bottom diagram (b) that illustrate installation examples of the camera unit and the support tube in the seventh embodiment.
Figure 39:
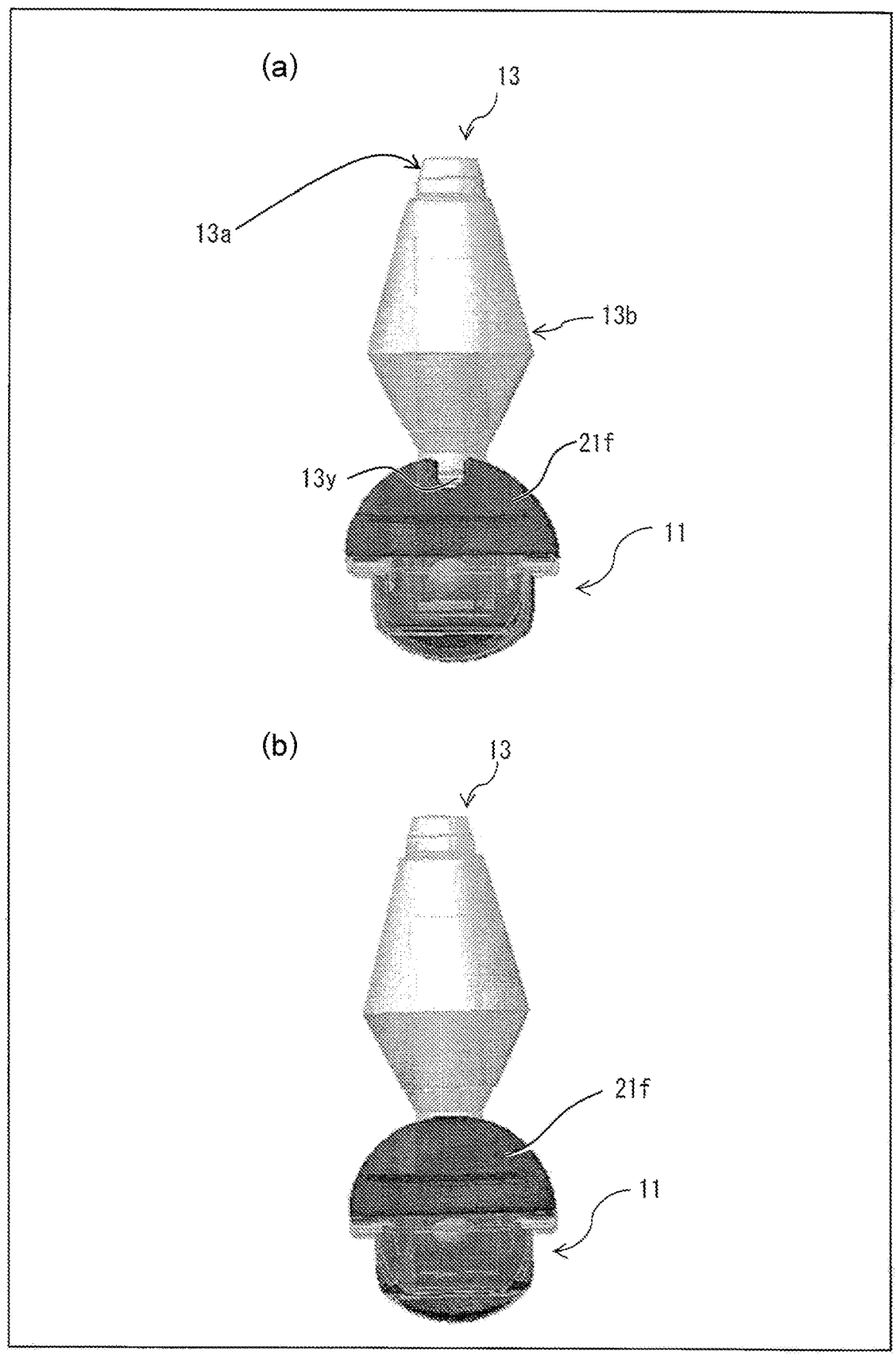
FIG. 39 is a right side diagram (a) and a left side diagram (b) that illustrate installation examples of the camera unit and the support tube in the seventh embodiment.

FIG. 33 is front diagrams (a) and (b) that illustrate installation examples of the camera unit, the support tube, the stopper, and the camera-side cable in a seventh embodiment. FIG. 34 is a front diagram (a) and a back diagram (b) that illustrate installation examples of the camera unit and the support tube in the seventh embodiment. FIG. 35 is perspective diagrams (a) to (c), as seen from an upper side, which illustrate installation examples of the camera unit and the support tube in the seventh embodiment. FIG. 36 is a perspective diagram of the camera unit in the seventh embodiment as seen from an upper side. FIG. 37 is perspective diagrams (a) and (b), as seen from a lower side, which illustrate installation examples of the camera unit and the support tube in the seventh embodiment. FIG. 38 is a plan diagram (a) and a bottom diagram (b) that illustrate installation examples of the camera unit and the support tube in the seventh embodiment. FIG. 39 is a right side diagram (a) and a left side diagram (b) that illustrate installation examples of the camera unit and the support tube in the seventh embodiment.

As illustrated in FIG. 33 to FIG. 39, the support tube 13 is configured with the core tube 13a that has the cable hole 13v (circular opening) and the attachment 13b that is attached to the outside surface of the core tube 13a. The core tube slit 13c that longitudinally crosses the core tube 13a from one opening to the other opening of the core tube 13a is formed in the core tube 13a. The hole diameter (the inner diameter of the support tube 13) of the cable hole 13v is smaller than the outer diameter of the camera-side cable connector.

As illustrated in FIG. 33 and FIG. 34, the attachment 13b is in a spindle shape that has the insertion hole D and is formed with the trocar connection portion 13x in a truncated conical shape that becomes thinner in the direction to separate from the camera unit 11 and the root portion 13z in a truncated conical shape that becomes thinner in the direction to approach the camera unit 11. Note that the taper angle of the root portion 13z is larger than the taper angle of the trocar connection portion 13x.

Further, the support tube 13 is configured by fitting the core tube 13a in the insertion hole D of the attachment 13b and thereby mounting the attachment 13b on the core tube 13a. Note that side surface recess portions 13t that overlap with the core tube slit 13c are provided to respective portions of the trocar connection portion 13x and the root portion 13z on a side surface of the attachment 13b.

Although not illustrated, a locking claw is provided on the inside of the attachment 13b, and a locking hole is provided in the position that is on the opposite side to the core tube slit 13c in the core tube 13a. Further, a guide claw of the attachment 13b is caused to match the position of the core tube slit 13c, and the locking hole is thereby fitted on the locking claw. As marks that indicate the guide claw, the side surface recess portions 13t are provided.

Here, the attachment 13b is configured such that the camera-side cable connector 15a may be placed through the inside of the insertion hole D. Specifically, the minimum hole diameter of the insertion hole D of the attachment 13b is set larger than the outer diameter of the camera-side cable connector 15a. However, embodiments are not limited to this construction. Even in a case where the minimum hole diameter of the insertion hole D of the attachment 13b is smaller than the outer diameter of the camera-side cable connector 15a, it is sufficient that the camera-side cable connector 15a may be placed through the inside of the insertion hole D by changing the orientation of the camera-side cable connector 15a. Further, it is also sufficient that the camera-side cable connector 15a may be placed through the inside of the insertion hole D by deforming the attachment 13b (changing the shape of the insertion hole D).

Further, the camera-side cable 12 has the stopper 48 that stops movement of the support tube 13 toward the connector 15a side between the connection end with the camera unit 11 and the camera-side cable connector 15a. The stopper 48 is configured to be capable of passing through the inside of the insertion hole D of the attachment 13b but not capable of passing through the inside of the core tube 13a. For example, the outer diameter of the stopper 48 is set smaller than the minimum hole diameter of the insertion hole D of the attachment 13b and larger than the minimum hole diameter of the cable hole 13v of the core tube 13a.

Further, the camera-side cable 12 that has the camera-side cable connector 15a and the stopper 48 is placed through the inside of the support tube 13 from the core tube slit 13c, the camera-side cable connector 15a and the stopper 48 are further placed through the inside of the insertion hole D (see FIG. 34) of the attachment 13b, the attachment 13b is mounted on the outside surface of the core tube 13a, and both of those are adhered together.

Note that as illustrated in (b) in FIG. 33 and FIG. 39, in the core tube 13a, the lower portion (the end portion on the camera unit 11 side) on which the attachment 13b is not mounted serves as the protrusion type joining portion 13y.

Note that on a side surface of the attachment 13b, an opening, a full slit (a longitudinally crossing slit that is from one end and reaches the other end), or a partial slit (a slit that does not reach the other end) may be provided.

As illustrated in FIGS. 33 and 34, the camera unit 11 is formed into a ship shape that is easily placed through the tubular tool and is provided with an image sensor, a circuit substrate, a control circuit, two illumination devices 27a and 27b, and so forth between the upper cover 21f and a lower cover 21g.

The upper cover 21f has a thin-long shape, two end portions (tip end portions) in the longitudinal direction form grip portions 22a and 22b, and the recess type joining portion 14 is formed in a central portion (see FIG. 36). The grip portions 22a and 22b are in a flat-plate shape, in which plural finger-print-like recesses are formed for preventing slip. Further, as illustrated in FIG. 39, the upper cover 21f curves so as to be protruded toward the support tube 13 side.

The lower cover 21g has light-transmitting characteristics. In a bottom view (see FIG. 38), the illumination device 27a is provided in the vicinity of the grip portion 22a, the illumination device 27b is provided in the vicinity of the grip portion 22b, and the lens 26 is provided between the two illumination devices 27a and 27b. Further, the lower cover 21g is provided with a light shielding portion 81 so as to surround the lens 26.

CONCLUSION

As described in the foregoing, an in-vivo monitoring camera system according to a first aspect of the present invention includes an image capturing portion that is capable of being introduced into a body, a support tube that has a connection portion with a tubular tool which is capable of being introduced into the body on one end side and has a joining portion to the image capturing portion on another end side, a cable that is connected with the image capturing portion and passes through the support tube, and a control system that is electrically connected with the cable and includes at least a display device.

In the above configuration, in the body, the image capturing portion may be joined to the support tube, the support tube may be connected with the tubular tool whose portion is introduced into the body, and the cable connected with the image capturing portion may thereby be drawn out to the outside of the body through the support tube and the tubular tool. Consequently, the supporting force for the image capturing portion is enhanced, connection failure of the cable is less likely to occur, and reliability is improved. Further, an operator may change the orientation of the image capturing portion in the body by operating the tubular tool, and easiness of use is thereby improved.

As for the in-vivo monitoring camera system according to a second aspect of the present invention, in the first aspect, the connection portion is configured to be in a tapered shape.

In the above configuration, connection steps between the support tube and the connection portion may easily be performed.

As for the in-vivo monitoring camera system according to a third aspect of the present invention, in the second aspect, an outer diameter of an end portion on a thinner side of the connection portion is configured to be smaller than an inner diameter of an end portion of the tubular tool on an inside of the body, and an outer diameter of an end portion on a thicker side of the connection portion is configured to be larger than the inner diameter of the end portion of the tubular tool on the inside of the body.

As for the in-vivo monitoring camera system according to a fourth aspect of the present invention, in any one of the first to third aspects, the cable is configured to have a connector on an opposite side to a connection end with the image capturing portion, and an inner diameter of the support tube is configured to be smaller than an outer diameter of the connector.

In the above configuration, because the support tube is not pulled off from the cable, the introduction into the body may smoothly be performed.

As for the in-vivo monitoring camera system according to a fifth aspect of the present invention, in the third aspect, the end portion on the thinner side of the connection portion is configured to be arranged in the tubular tool in the body, and the end portion on the thicker side of the connection portion is configured to be arranged outside the tubular tool in the body.

In the above configuration, the connection force between the tubular tool and the support tube may be enhanced.

As for the in-vivo monitoring camera system according to a sixth aspect of the present invention, in the second aspect, the connection portion is configured to have a conical or truncated conical shape, a taper angle of the connection portion is configured to be a value that corresponds to a shape of an opening of the tubular tool on the inside of the body.

In the above configuration, regardless of the orientation or rotational angle of the tubular tool, the image capturing portion may appropriately be installed.

As for the in-vivo monitoring camera system according to a seventh aspect of the present invention, in any one of the first to sixth aspects, the support tube is configured to have a root portion between the connection portion and the joining portion, and the root portion is configured to have a tapered shape that becomes thinner toward a joining portion side.

In the above configuration, separation steps between the image capturing portion and the support tube may smoothly be performed.

As for the in-vivo monitoring camera system according to an eighth aspect of the present invention, in the seventh aspect, the root portion is configured to have a conical or truncated conical shape, and a taper angle of the root portion is configured to be a value that corresponds to the shape of the opening of the tubular tool, which is used to guide the image capturing portion to the outside of the body, on the inside of the body.

In the above configuration, separation steps between the image capturing portion and the support tube may more smoothly be performed.

As for the in-vivo monitoring camera system according to a ninth aspect of the present invention, in any one of the first to eighth aspects, a length of the support tube may be configured to be a value that corresponds to a shape of an opening of the tubular tool on a side for introduction into the body and a structure of the image capturing portion.

As for the in-vivo monitoring camera system according to a tenth aspect of the present invention, in any one of the first to ninth aspects, a configuration material or a composition of the support tube is configured to include a material that is detectable by X-rays.

In the above configuration, the position of the support tube in the body may be detected by using X-rays.

As for the in-vivo monitoring camera system according to an eleventh aspect of the present invention, in any one of the first to tenth aspects, either one or both of the image capturing portion and the cable are configured to include the material that is detectable by X-rays.

In the above configuration, the position of each component in the body may be detected by using X-rays.

As for the in-vivo monitoring camera system according to a twelfth aspect of the present invention, in the fourth aspect, the connector is configured to include a material that is detectable by X-rays.

In the above configuration, the position of the connector in the body may be detected by using X-rays.

As for the in-vivo monitoring camera system according a thirteenth aspect of the present invention, in any one of the first to twelfth aspects, at least a portion of a surface of the support tube is configured to be in a color that corresponds to visible light with a wavelength of 420 to 570 nm.

In the above configuration, viewing of the support tube in the body becomes easy.

As for the in-vivo monitoring camera system according to a fourteenth aspect of the present invention, in any one of the first to thirteenth aspects, a slit is configured to be formed in the support tube.

In the above configuration, the cable may be placed through the support tube from a side surface, and manufacture becomes easy. Further, the heat dissipation of the support tube may be enhanced.

As for the in-vivo monitoring camera system according to a fifteenth aspect of the present invention, in any one of the first to fourteenth aspects, an inside surface of the support tube is configured to contact with the cable.

In the above configuration, the support tube may be retained by the cable by a moderate force.

As for the in-vivo monitoring camera system according to a sixteenth aspect of the present invention, in the fifteenth aspect, a gap which gas enters is configured to be provided between the inside surface and the cable.

In the above configuration, the support tube may be prevented from unnecessarily moving and inhibiting installation of the camera unit. Further, in a case where sterilization by gas is performed, sterilization gas enters the contact surface between the support tube and the cable, and the cable and the support tube may thoroughly be sterilized.

As for the in-vivo monitoring camera system according to a seventeenth aspect of the present invention, in any one of the first to sixteenth aspects, the support tube is configured to include a core tube and an attachment that has an insertion hole through which the core tube is placed and that is mounted on an outside surface of the core tube.

In the above configuration, support tubes suitable for various tubular tools may be configured.

As for the in-vivo monitoring camera system according to an eighteenth aspect, in the seventeenth aspect, the joining portion is configured to be provided on one end side of the core tube, and the connection portion is configured to be provided to the attachment.

As for the in-vivo monitoring camera system according to a nineteenth aspect of the present invention, in the seventeenth aspect, the attachment is configured to be in a spindle shape.

As for the in-vivo monitoring camera system according to a twentieth aspect of the present invention, in the seventeenth aspect, the cable is configured to have a connector on the opposite side to the connection end with the image capturing portion, and the attachment is configured such that the connector is capable of being placed through an inside of the insertion hole.

In the above configuration, manufacturing steps may be simplified.

As for the in-vivo monitoring camera system according to a twenty-first aspect of the present invention, in the seventeenth aspect, all configuration components of the support tube that include the core tube and the attachment are configured to include a material that is detectable by X-rays.

In the above configuration, the positions of the configuration components of the support tube in the body may be detected by using X-rays. Further, the ratios of the material included in the respective configuration components may be adjusted to respective appropriate amounts in accordance with the shapes and sizes.

As for the in-vivo monitoring camera system according to a twenty-second aspect of the present invention, in the seventeenth aspect, a material with thermal conductivity is configured to be used for the core tube.

In the above configuration, the heat dissipation of the support tube may be enhanced.

As for the in-vivo monitoring camera system according to a twenty-third aspect of the present invention, in the seventeenth aspect, an insulating material is configured to be used for the attachment.

In the above configuration, the safety in the body may be enhanced.

As for the in-vivo monitoring camera system according to a twenty-fourth aspect of the present invention, in the seventeenth aspect, a slit is configured to be formed in the core tube.

In the above configuration, the cable may be placed through the support tube from a side surface, and manufacture becomes easy. Further, the heat dissipation of the support tube may be enhanced.

As for the in-vivo monitoring camera system according to a twenty-fifth aspect of the present invention, in the seventeenth aspect, a fitting force between the core tube and the attachment is configured to be greater than a joining force between the image capturing portion and the support tube.

In the above configuration, the possibility that the core tube is split from the attachment in the body may be lessened.

As for the in-vivo monitoring camera system according to a twenty-sixth aspect of the present invention, in any one of the first to twenty-fifth aspects, the cable is configured to have a connector that is provided on the opposite side to the connection end with the image capturing portion and a stopper that stops movement of the support tube toward a connector side.

As for the in-vivo monitoring camera system according to a twenty-seventh aspect of the present invention, in the seventeenth aspect, the cable is configured to have a connector that is provided on an opposite side to a connection end with the image capturing portion and a stopper that stops movement of the support tube toward a connector side, and the stopper is configured to be capable of passing through an inside of the insertion hole but not capable of passing through an inside of the core tube.

As for the in-vivo monitoring camera system according to a twenty-eighth aspect of the present invention, in the sixth aspect, the taper angle of the connection portion is configured to be 5° or more to 30° or less.

As for the in-vivo monitoring camera system according to a twenty-ninth aspect of the present invention, in the eighth aspect, the taper angle of the root portion is configured to be 15° or more to 45° or less.

As for the in-vivo monitoring camera system according to a thirtieth aspect of the present invention, in the ninth aspect, the length of the support tube is configured to be 10 mm or more to 50 mm or less.

In this point, it is possible that a length of less than 10 mm causes difficulty in connection with the tubular tool or joining to the image capturing portion. It is possible that a length that exceeds 50 mm causes difficulty in handling in the body cavity or narrows the viewing area because the position of the image capturing portion is separated from the body wall.

As for the in-vivo monitoring camera system according to a thirty-first aspect of the present invention, in the seventeenth aspect, at least one of a recess portion, a groove portion, an opening, and a slit is configured to be formed in a side surface of the attachment.

In the above configuration, the manufacturing steps may be made easy, the heat dissipation of the support tube may be enhanced, and sterilization of the cable and the support tube may be made certain.

A support tube (support instrument) according to a thirty-second aspect of the present invention is a support tube that is used for an in-vivo monitoring camera system in which a cable connected with an image capturing portion introduced into a body is drawn out to an outside of the body through a tubular tool whose portion is introduced into the body and which is electrically connected with a control system on the outside of the body and that has a connection portion with the tubular tool on one end side and has a joining portion to the image capturing portion on the other end side.

In the above configuration, in the body, the support tube may be joined to the image capturing portion by the joining portion, the support tube may be connected with the tubular tool by the connection portion, and the cable connected with the image capturing portion may thereby be drawn out to the outside of the body through the support tube and the tubular tool. Consequently, the supporting force for the image capturing portion is enhanced, connection failure of the cable is less likely to occur, and reliability is improved. Further, an operator may change the orientation of the image capturing portion in the body by operating the tubular tool, and easiness of use is thereby improved.

The present invention is not limited to the above embodiments. Modes that are the above embodiments appropriately changed or obtained by combining those based on common general technical knowledge are also included in embodiments of the present invention.

INDUSTRIAL APPLICABILITY

This in-vivo monitoring camera system is preferably used for endoscopic surgery or the like.

REFERENCE SIGNS LIST 1 in-vivo monitoring camera system
11 camera unit (image capturing portion)
12 camera-side cable (cable)
13, 130, 131 support tube
13x trocar connection portion
13y protrusion type joining portion
13a core tube
13b attachment
13c core tube slit
14 recess type joining portion
15a camera-side cable connector
15b apparatus-side cable connector
16 apparatus-side cable
31 trocar (tubular tool)
48 stopper

The invention claimed is:

1. An in-vivo monitoring camera system comprising:
an image capturing portion that is capable of being introduced into a body;
a support tube that has a connection portion with a tubular tool which is capable of being introduced into the body on one end side and has a joining portion to the image capturing portion on another end side;
a cable that is connected with the image capturing portion and passes through the support tube; and
a control system that is electrically connected with the cable, wherein
an outer surface of the connection portion is connected with the tubular tool, the outer surface of the connection portion having a tapered shape,
the support tube has a root portion between the connection portion and the joining portion, and
the root portion is in a tapered shape that becomes thinner in a direction to approach the joining portion.

2. An in-vivo monitoring camera system comprising:
an image capturing portion that is capable of being introduced into a body;
a support tube that has a connection portion with a tubular tool which is capable of being introduced into the body on one end side and has a joining portion to the image capturing portion on another end side;
a cable that is connected with the image capturing portion and passes through the support tube; and
a control system that is electrically connected with the cable, wherein
an outer surface of the connection portion is connected with the tubular tool, the outer surface of the connection portion having a tapered shape, and
the support tube includes a core tube and an attachment that has an insertion hole through which the core tube is placed and that is mounted on an outside surface of the core tube.

3. The in-vivo monitoring camera system according to claim 2, wherein the joining portion is provided on one end side of the core tube, and the connection portion is provided to the attachment.

4. The in-vivo monitoring camera system according to claim 2, wherein the attachment is in a spindle shape.

5. The in-vivo monitoring camera system according to claim 2, wherein the cable has a connector on an opposite side to a connection end with the image capturing portion, and the attachment is configured such that the connector is capable of being placed through an inside of the insertion hole.

6. The in-vivo monitoring camera system according to claim 2, wherein a material with thermal conductivity is used for the core tube.

7. The in-vivo monitoring camera system according to claim 2, wherein an insulating material is used for the attachment.

8. The in-vivo monitoring camera system according to claim 2, wherein a slit is formed in the core tube.

9. The in-vivo monitoring camera system according to claim 2, wherein a fitting force between the core tube and the attachment is greater than a joining force between the image capturing portion and the support tube.

* * * * *